United States Patent
Stinchcomb et al.

(10) Patent No.: US 9,695,143 B2
(45) Date of Patent: *Jul. 4, 2017

(54) PRODRUGS OF TETRAHYDROCANNABINOL, COMPOSITIONS COMPRISING PRODRUGS OF TETRAHYDROCANNABINOL AND METHODS OF USING THE SAME

(71) Applicant: Zynerba Pharmaceuticals, Inc., New York, NY (US)

(72) Inventors: Audra Lynn Stinchcomb, Ruxton, MD (US); Miroslaw Jerzy Golinski, Lexington, KY (US); Dana Carmel Hammell, Georgetown, KY (US); Jeffrey Lynn Howard, Lexington, KY (US)

(73) Assignee: Zynerba Pharmaceuticals, Inc., Devon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/620,016

(22) Filed: Feb. 11, 2015

(65) Prior Publication Data

US 2015/0218121 A1 Aug. 6, 2015

Related U.S. Application Data

(62) Division of application No. 13/555,741, filed on Jul. 23, 2012, now Pat. No. 8,980,942, which is a division
(Continued)

(51) Int. Cl.
*A61K 31/35* (2006.01)
*A61K 31/665* (2006.01)
(Continued)

(52) U.S. Cl.
CPC .......... *C07D 311/74* (2013.01); *A61K 31/352* (2013.01); *C07D 311/80* (2013.01); *C07D 405/12* (2013.01); *C07F 9/65522* (2013.01)

(58) Field of Classification Search
CPC .. C07D 311/74; C07D 311/80; C07D 31/352; C07D 405/12; C07F 9/65522
(Continued)

(56) References Cited

U.S. PATENT DOCUMENTS 3,941,782 A 3/1976 Harris et al.
4,327,028 A 4/1982 Kaplan
(Continued)

FOREIGN PATENT DOCUMENTS

CA 967971 A 5/1975
FR 2.081.512 12/1971
(Continued)

OTHER PUBLICATIONS

Knaus et al, The separation, identification, and quantitation of cannabinoids and their t-butyldimethylsilyl, trimethylsilylacetate, and diethylphosphate derivatives using high-pressure liquid chromatography, gas-liquid chromatography, and mass spectrometry, Journal of Chromatographic Science, 1976, 14(11).p. 525-530 [ a abstract (2 pages).*

(Continued)

*Primary Examiner* — T. Victor Oh
(74) *Attorney, Agent, or Firm* — McCarter & English, LLP; Danielle L. Herritt

(57) ABSTRACT

Described herein are $\Delta^9$-THC prodrugs, methods of making $\Delta^9$-THC prodrugs, formulations comprising $\Delta^9$-THC prodrugs and methods of using $\Delta^9$-THC. One embodiment described herein relates to the transdermal administration of a $\Delta^9$-THC prodrug for treating and preventing diseases and/or disorders.

10 Claims, 6 Drawing Sheets

Related U.S. Application Data of application No. 12/326,036, filed on Dec. 1, 2008, now Pat. No. 8,227,627.

(60) Provisional application No. 60/991,555, filed on Nov. 30, 2007, provisional application No. 61/037,568, filed on Mar. 18, 2008.

(51) Int. Cl.
| | |
|---|---|
| *C07D 311/80* | (2006.01) |
| *C07D 311/74* | (2006.01) |
| *A61K 31/352* | (2006.01) |
| *C07D 405/12* | (2006.01) |
| *C07F 9/655* | (2006.01) |

(58) Field of Classification Search
USPC .................................. 549/390; 514/454, 100
See application file for complete search history.

(56) References Cited

U.S. PATENT DOCUMENTS

| | | | |
|---|---|---|---|
| 4,933,363 | A | 6/1990 | ElSohly |
| 5,684,161 | A | 11/1997 | Imoto |
| 6,380,175 | B1 * | 4/2002 | Hussain ............... A61K 9/0043 |
| | | | 514/100 |
| 8,227,627 | B2 | 7/2012 | Stinchcomb et al. |
| 8,980,942 | B2 * | 3/2015 | Stinchcomb ......... A61K 31/352 |
| | | | 514/454 |
| 2006/0264647 | A1 | 11/2006 | Field et al. |
| 2008/0275237 | A1 | 11/2008 | Arslantas et al. |

FOREIGN PATENT DOCUMENTS

| | | |
|---|---|---|
| FR | 2081512 A | 12/1971 |
| GB | 1 313 977 | 4/1973 |
| JP | 5551604 B2 | 7/2014 |
| WO | WO 94/27533 A1 | 12/1994 |
| WO | WO 00/45813 A1 | 8/2000 |
| WO | WO 02/096899 A1 | 12/2002 |
| WO | WO-2006/007734 A1 | 1/2006 |
| WO | WO 2006/029089 A2 | 3/2006 |
| WO | WO 2007/041167 A2 | 4/2007 |
| WO | WO 2008/134668 A2 | 11/2008 |

OTHER PUBLICATIONS

A.J. Hampson et al., Cannabidiol and (−)Δ9-tetrahydrocannabinol are Neuroprotective Antioxidants, 95 Proceedings Nat'l Acad. Sciences 8268-73 (1998).

Ahmet Dogrul et al., Topical Cannabinoid Antinociception: Synergy With Spinal Sites, 105 Pain 11-16 (2003).

Alison Drysdale and Bettina Platt, Cannabinoids: Mechanisms and Therapeutic Applications in the CNS, 10 Current Medicinal Chemistry 2719-32 (2003).

Andrea Hohmann and Richard Suplita, Endocannabinoid Mechanisms of Pain Modulation, 8:4 Amer. Assoc or Pharmaceutical Scientists Article 79, E693-708 (2006).

Angela Alsasua del Valle, Implication of Cannabinoids in Neurological Diseases, 26:4-6 Cellular & Molecular Neurobiology 579-91 (2006).

Angela Huskey, Cannabinoids in Cancer Pain Management. 20:3 J Pain & Palliative Care Pharmacotherapy 43-46 (2006).

B.A. Zitko et al., "Water-Soluble Derivatives of Delta-1-Tetrahydrocannabinol" 177 Science 442-44 (1972).

Barbara Costa, On the Pharmacological Properties of Delta 9-Tetrahydrocannabinol (THC), 4 Chemistry & Biodiversity 1664-1677 (2007).

Büyüktimkin, et al., "Synthesis and Enhancing Effect of Dodecyl 2-(N,N-Dimethylamino)propionate on the Transepidermal Delivery of Indomethacin, Clonidine, and Hydrocortisone," Pharmaceutical Research, vol. 10(11), pp. 1632-1637 (1993).

Carol Hamelink et al., Comparison of Cannabidiol, Antioxidants, and Diuretics in Reversing Binge Ethanol-Induced Neurotoxicity, 314:2 J. Pharmacology & Experimental Therapeutics 780-88 (2005).

Choi, et al, "Formulation and Evaluation of Ketorolac Transdermal Systems," Drug Delivery, vol. 14, pp. 69-74 (2007).

Christian Felder et al., Cannabinoid Biology: The Search for New Therapeutic Targets, 6:3 Molecular Interventions 149-61 (2006).

Christoph Michalski et al., Cannabinoids Ameliorate Pain and Reduce Disease Pathology in Cerulein-Induced Acute Pancreatitis, 132 Gastroenterology 1968-78 (2007).

D.R. Compton et al., "Cannabinoid Structure-Activity Relationships: Correlation of Receptor Binding and in Vivo Activities" 265:1 J Pharmacology and Experimental Therapeutics 218-26 (1993).

David Baker et al.. Cannabinoids Control Spasticity and Tremor in a Multiple Sclerosis Model, 404 Nature 84-87 (2000).

Didier M. Lambert, et al., The Endocannabinoid System: Drug Targets, Lead Compounds, and Potential Therapeutic Applications, 48:16 J. Medicinal Chemistry, 5059-87 (2005).

Elisabeth Gordon and Orrin Devinsky, Alcohol and Marijuana: Effects on Epilepsy and Use by Patients with Epilepsy, 42:10 Epilepsia 1266-72 (2001).

Elizabeth M. Williamson and Fred J Evans, Cannabinoids in Clinical Practice, 60:6 Drugs 1303-14 (2000).

Erica J. Carrier et al., Inhibition of an Equilibrative Nucleoside Transporter by Cannabidiol: A Mechanism of Cannabinoid Immunosuppression, 103:20 PNAS 7895-900 (2006).

Ethan Russo and Godfrey Guy, A Tale of Two Cannabinoids: The Therapeutic Rationale for Combining Tetrahydrocannabinol and Cannabidiol, 66 Medical Hypothesis 234-246 (2006).

Franjo Grotenhermen, Cannabinoids for Therapeutic Use: Designing Systems to Increase Efficacy and Reliability, 2:4 Healthcare Technology Review 229-40 (2004).

Franjo Grotenhermen, Clinical Pharmacokinetics of Cannabinoids, 3:1 J. Cannabis Therapeutics 3-51 (2003).

Franjo Grotenhermen, Pharmacokinetics and Pharmacodynamics of Cannabinoids, 42:4 Clinical Pharmacokinetics 327-360 (2003).

G. Mucioli and D. Lambert, Current Knowledge on the Antagonists and Inverse Agonists of Cannabinoid Receptors, 12 Current Medicinal Chemistry 1361-94 (2005).

Gennaro, Alfonso, Remington: The Science and Practice of Pharmacy, 20th ed., pp. 842-843 (2000).

Giancarlo Colombo et al., Endocannabinoid System and Alcohol Addiction: Pharmacological Studies, 81 Pharmacology Biochemistry & Behavior 369-80 (2005).

Guillermo Velasco et al., Cannabinoids and Gliomas, 36 Mol. Neurobiology 60-67 (2007).

Gwak, et al.,"Effect of vehicles and penetration enhancers on the in vitro percutaneous absorption of tenoxicam through hairless mouse skin," International Journal of Pharmaceutics, vol. 236, pp. 57-64 (2002).

Harrison, et al., "The Relative Effect of Azone® and Transcutal® on Permeant Diffusivity and Solubility in Human Stratum Corneum," Pharmaceutical Research, vol. 13(4), pp. 542-546 (1996).

Helton, et al.,"Pharmacokinetic profiles in rats after Intravenous, oral, or dermal administration of dapsone," Drug Metabolism and Disposition, vol. 28(8), pp. 925-929 (2000).

Ileana Tomida et al., Effect of Sublingual Application of Cannabinoids on Intraocular Pressure: A Pilot Study, 15 J. Glaucoma 349-353 (2006).

International Search Report for PCT/US2008/085201, mailed on May 13, 2009.

J. Ludovic Croxford, Therapeutic Potential of Cannabinoids in CNS Disease, 17:3 CNS Drugs 179-202 (2003).

Jorge Manzanares et al., Interactions Between Cannabinoid and Opioid Receptor Systems in the Mediation of Ethanol Effects, 40:1 Alcohol & Alcoholism 25-34 (2005).

Jos H.M. Lange and Chris G. Kruse, Recent Advances in CB1 Cannabinoid Receptor Antagonists, 7:4 Current Opinion in Drug Discovery & Dev. 498-506 (2004).

(56) References Cited

OTHER PUBLICATIONS

Juha Juntunen et al., In-vitro Corneal Permeation of Cannabinoids and Their Water-Soluble Phosphate Ester Prodrugs, 57 J. Pharmacy & Pharmacology 1153-57 (2005).
Julia Juntunen et al., In-Vitro Corneal Permeation of Cannabinoids and Their Water-Soluble Phosphate Ester Prodrugs, 57 J. Pharmacy & Pharmacology 1153-57 (2005).
Lois Kehl et al., A Cannabinoid Agonist Differentially Attenuates Deep Tissue Hyperalgesia in Animal Models of Cancer and Inflammatory Muscle Pain, 103 Pain 175-86 (2003).
M. A Elsohly et al., Rectal bioavailability of delta-9-tetrahydrocannabinol from various esters, 40(3) Pharmacology, Biochemistry and Behavior, 497-502 (1991).
M. Guzman et al., A pilot clinical study of delta-9-tetrahydrocannabinol in patients with recurrent glioblastoma multiforme, 95 British J of Cancer 197-203 (2006).
M. Munjal et al., Chemical stabilization of a Delta 9-tetrahydrocannabinol prodrug in polymeric matrix systems produced by a hot-melt method: Role of microenvironment pH, 7:3 Amer. Assoc. Pharm. Sci. PharmSciTech Article 71 E1-E12 (2006).
M. Munjal, et al., Polymeric systems for amorphous Delta(9)-tetrahydrocannabinol produced by a hot-melt method. Part II: Effect of oxidation mechanisms and chemical interactions on stability, 95:11 Journal of Pharmaceutical Sciences, 2473-2485 (2006).
M.A. ElSohly et al., "Rectal Bioavailability of Delta-9-Tetrahydrocannabinol From Various Esters" 40 Pharmacology Biochemistry & Behavior 497-502 (1991).
Meliha Karsak, Attenuation of Allergic Contact Dermatitis Through the Endocannabinoid System, 316 Science 1494-97(2007).
Mellar Davis, et al., The Emerging Role of Cannabinoid Neuromodulators in Symptom Management 15 Support Care Cancer 63-71 (2007).
Mohamed Ben Amar, Cannabinoids in Medicine: A Review of Their Therapeutic Potential, 105 J. Ethnopharmacology 1-25 (2006).
Møllgaard, et al., "Permeation of estradiol through the skin—effect of vehicles," International Journal of Pharmaceutics, vol. 15, pp. 185-197 (1983).
N. Brown, D. Harvey, In Vitro Metabolism of Cannabichromene in Seven Common Laboratory Animals, 18:6 Drug Metabolism & Disposition 1065-70 (1990).
N. Clayton et al., CB1 and CB2 Cannabinoid Receptors are Implicated in Inflammatory Pain, 96 Pain 253-60 (2002).
Natalya Kogan, Cannabinoids and Cancer, 5 Mini-Reviews in Medicinal Chemistry 941-42 (2005).
P. Consroe et al., "Use of a Potential Rabbit Model for Structure-Behavioral Activity Studies of Cannabinoids" 25 J Medicinal Chemistry 596-99 (1982).
Pal Pacher et al., The Endocannabinoid System as an Emerging Target or Pharmacotherapy, 58:3 Pharmacological Reviews 389-462 (2006).
Prasad V.N. Challapalli, Audra Stinchcomb, In Vitro Experiment Optimization for Measuring Tetrahydrocannabinol Skin Permeation, 241 Int'l J. Pharmaceutics 329-39 (2002).
Puglia, el al., "Evaluation of in vitro percutaneous absorption of lorazepam and clonazepam from hydro-alcoholic gel Ibrinulations," International Journal of Pharmaceutics, vol. 228, pp. 79-87 (2001).
Rafael Maldonado et al., Involvement of the Endocannabinoid System in Drug Addiction, 29:4 Trends in Neurosciences 225-32 (2006).
Raphale Mechoulan and Lumir Hanus, Cannabidiol: An Overview of Some Chemical and Pharmacological Aspects, Part I: Chemical Aspects, 121 Chemistry & Physics of Lipids 35-43 (2002).
Remigius Agu et al., Permeation of WIN 55,212-2, a Potent Cannabinoid Receptor Agonist, Across Human Trachea-Broncial Tissue In Vitro and Rat Nasal Epithelium In Vivo, 58 J. Pharmacy & Pharmacology 1459-65 (2006).
Robert J. McKallip et al., Cannabidiol-Induced Apoptosis in Human Leukemia Cells: A Novel Role of Cannabidiol in Regulation of p22phox and Nox4 Expression, 70:3 Molecular Pharmacology 897-908 (2006).
Roger G. Pertwee, Cannabidiol as a Potential Medicine, Milestones in Drug Therapy, 47-65 (2005).
Roger G. Pertwee, The Therapeutic Potential of Drugs That Target Cannabinoid Receptors or Modulate the Tissue Levels or Actions of Endocannabinoids, 7(3) Amer. Assoc. Pharm. Sciences Article 64, E625-54 (2005).
Roman Rukwied et al., Cannabinoid Agonists Attenuate Capsaicin-Induced Responses in Human Skin, 102 Pain 283-88 (2003).
Sanjeet Narang, Efficacy of Dronabinol as an Adjuvant Treatment for Chronic Pain Patients on Opioid Therapy, 9:4 J. of Pain 254-264 (2008).
Satyanarayana Valiveti and Audra Stinchcomb, Liquid Chromatographic—Mass Spectrometric Quantitation of $\Delta 9$-tetrahydrocannabinol and Two Metabolites in Pharmacokinetic Study Plasma Samples, 803 J. Chromatography 243-48 (2004).
Satyanarayana Valiveti et al., In Vitro/In Vivo Correlation Studies for Transdermal $\Delta 8$-THC Development, 93:5 J. Pharmaceutical Scis. 1154-64 (2004).
Satyanarayana Valiveti et al., Intranasal Absorption of $\Delta 9$-tetrahydrocannabinol and WIN55,212-2 Mesylate in Rats, 65 European J. Pharmaceutics & Biopharmaceutics 247-52 (2007).
Satyanarayana Valiveti et al., Transdermal Permeation of WIN 55,212-2 and CP 55,940 in Human Skin In Vitro, 278 Int'l J Pharmaceutics 173-180 (2004).
Satyanarayana Valiveti, et al., Transdermal Delivery of Synthetic Cannabinoid WIN 55,212-2 in Vitro/in Vivo Correlation, 21:7 Pharmaceutical Research 1137-45 (2004).
Sintov, et al., "Cutaneous biotransformation of N-(4-bromobenzoyl)-S,S-dimethyliminosulfurane and its product, 4-bromobenzamide, leading to percutaneous penetration enhancement of drugs: Initial evidence using hydrocortisone," Journal of Controlled Release, vol. 133, pp. 44-51 (2009).
Stinchcomb et al., Human Skin Permeation of $\Delta 8$-tetrahydrocannabinol, Cannabidiol and Cannabinol, 56 J Pharmacy & Pharmacology 291-97 (2004).
Susann Tehilibon, Raphael Mechoulam, Synthesis of a Primary Metabolite of Cannabidiol, 2:21 Organic Letters 3301-03(2000).
T. Philip Malan, Jr., et al., CB2 Cannabinoid Receptor Agonists: Pain Relief Without Physcoactive Effects?, 3 Current Opinion in Pharmacology 62-67 (2003).
Tammy Burns and Joseph Ineck, Cannabinoid Analgesia as a Potential New Therapeutic Option in the Treatment of Chronic Pain, 40 Annals of Pharmacotherapy 251-60 (2006).
Thomas Klein, Cannabinoid-Based Drugs as Anti-Inflammatory Therapeutics, 5 Nature Reviews 400-11 (2005).
Tiziana Bisogno et al., The Endocannabinoid Signaling System: Biochemical Aspects, 81 Pharmacology, Biochemistry, Behavior 224-38 (2005).
V. Martinez et al., Dendritic core-shell macromolecules soluble in supercritical carbon dioxide, 39:12 Macromolecules 3978-3979 (2006).
Vincenzo Di Marzo and Luciano De Petrocellis, Plant, Synthetic, and Endogenous Cannabinoids in Medicine, 57 Annual Reviews of Medicine 553-74 (2006).
Vincenzo Di Mario et al., The Endocannabinoid System and its Therapeutic Exploitation, 3 Nature Reviews 771-84 (2004).
Walters, Kenneth, "Penetration Enhancers and Their Use in Transdermal Therapeutic Systems," Transdermal Drug Delivery Developmental Issues and Research Initiatives, Marcel Dekker, Inc., pp. 197-246 (1989).
Wen Jiang et al., Cannabinoids Promote Embryonic and Adult Hippocampus Neurogenesis and Produce Anxiolytic- and Antidepressant-Like Effects, 115:11 J of Clinical Investigation 3104-16 (2005).
Written Opinion of the International Searching Authority for PCT/US2008/085201, mailed on May 13, 2009.
Y. Marchalant et al, Anti-Inflammatory Property of the Cannabinoid Agonist Win-55212-2 in a Rodent Model of Chronic Brain Inflammation, 144 Neuroscience 1516-22 (2007).
European Patent Office partial search report on application 15172043.0 dated Oct. 7, 2015; 8 pages.

(56) References Cited

OTHER PUBLICATIONS

Gaoni Y., et al. The Isolation and Structure of Delta1-Tetrahydrocannabinol and Other Neutral Cannabinoids from Hashish, J. Am. Chem. Soc. 93:1, 217 (1971).

Knaus, E.E., et al.; The Separation, Identification, and Quantitation of Cannabinoids and Their t-Butyldimethylsilyl, Trimethylsilylacetate, and Diethylphosphate Derivates Using High-Pressure Liquid Chromatography, Gas-Liquid Chromatography, and Mass Spectrometry; Nov. 1976; pp. 525-530; Journal of Chromatographic Science, vol. 14.

\* cited by examiner

FIGURE 10

| Compound | Log P* |
|---|---|
| $\Delta^9$-tetrahydrocannabinol | 7.68 ± 0.35 |
| ALL00117 | 6.81 ± 0.60 |
| ALL00118 | 7.73 ± 0.42 |
| ALL00119 | 6.51 ± 0.61 |
| ALL00120 | 7.07 ± 0.41 |
| ALL00121 | 6.66 ± 0.47 |
| ALL00122 | 6.73 ± 0.69 |
| ALL00123 | 7.55 ± 0.39 |
| ALL00124 | 7.40 ± 0.36 |
| ALL00125 | 7.46 ± 0.41 |
| ALL00126 | 6.32 ± 0.44 |
| ALL00127 | 7.52 ± 0.41 |
| ALL00129 | 7.28 ± 0.60 |
| ALL00130 | 7.00 ± 0.41 |
| ALL00133 | 7.17 ± 0.39 |
| ALL00134 | 6.64 ± 0.43 |
| ALL00138 | 6.32 ± 0.44 |
| ALL00144 | 6.64 ± 0.43 |
| ALL00153 | 7.90 ± 0.40 |
| ALL00154 | 6.95 ± 0.41 |

PRODRUGS OF TETRAHYDROCANNABINOL, COMPOSITIONS COMPRISING PRODRUGS OF TETRAHYDROCANNABINOL AND METHODS OF USING THE SAME

CROSS REFERENCE TO RELATED APPLICATION

This application is a divisional of U.S. application Ser. No. 13/555,741, filed Jul. 23, 2012, allowed; which is a divisional of U.S. application Ser. No. 12/326,036, filed Dec. 1, 2008, now U.S. Pat. No. 8,227,627; and claims the benefit of U.S. Provisional Application Ser. Nos. 60/991,555, filed Nov. 30, 2007, and 61/037,568, filed Mar. 18, 2008, which are hereby incorporated by reference.

FIELD

Described herein are pharmaceutically active agents suitable for pharmaceutical use such as transdermal delivery to a mammal, compositions for transdermal delivery of pharmaceutically active agents and the use of such compositions in treating diseases and disorders.

BACKGROUND

Pain is the most frequently reported symptom and it is a common clinical problem which confronts the clinician. Millions of people in the USA suffer from severe pain that, according to numerous recent reports, is chronically undertreated or inappropriately managed. Similarly, millions of people also suffer from severe nausea and/or frequent emesis. Moreover, all too frequently, many patients suffering from chronic, under-treated or unretractable pain, also suffer from lack of appetite, nausea and/or frequent emesis, such that a patient is unable to receive effective therapeutic doses of oral pain medications, thereby exacerbating their pain.

The clinical usefulness of the cannabinoids, including $\Delta^9$-tetrahydrocannabinol ($\Delta^9$-THC), to provide analgesia, help alleviate nausea and emesis, as well as stimulate appetite has been well-recognized.

A "wasting syndrome" generally describes a clinical syndrome in which an individual has lost more than 10% of his or her body weight in the absence of active infections or any other identifiable cause of weight loss. The weight loss exemplified in a wasting syndrome can result from malabsorption, diarrhea, reduced food intake or altered metabolism. While wasting syndromes can present secondarily to many illnesses and conditions, it frequently develops as a co-morbid condition, secondary to chemotherapy and human immunodeficiency virus infection (a.k.a HIV-wasting). Cannabinoids, such as $\Delta^9$-THC, are effective in treating and alleviating wasting syndromes, including, but not limited to HIV-wasting and chemotherapy induced wasting. Indeed, $\Delta^9$-THC is currently available in an oral dosage, sold under the trade name Marinol®, to treat this indication.

Anorexia is a depressed sensation of appetite. In severe cases, an individual with anorexia can experience a clinically significant loss in body weight. Anorexia can appear as a secondary symptom to many disorders including severe depression, cancer, Crohn's disease, ulcerative colitis, dementia, superior mesenteric artery syndrome and chronic renal failure. Anorexia can also result from the use of certain drugs, particularly stimulants and narcotics such as cocaine and heroin. Anorexia nervosa, is a specific type of anorexia, which is a psychiatric disorder, describing an eating disorder, characterized by low body weight and body image distortion, with an obsessive fear of gaining weight. Administration of $\Delta^9$-THC can increase the appetite of individuals experiencing anorexia that has resulted in clinically significant loss in weight, including individuals suffering from anorexia nervosa, as well individuals with anorexia secondary to either another diagnosis or drug use.

A notable percentage of the U.S. population satisfy the diagnostic criteria for alcohol use disorders ("AUDs"). The consumption of excessive amounts of alcohol results in a complex array of pharmacological effects that directly impact the ability to treat the condition. These effects directly impact the brain and include progressive neurodegenration, impaired executive function and dependence leading to withdrawal-induced negative effects. It is known that the cannabinoids, including $\Delta^9$-THC and $\Delta^9$-THC prodrugs have neuroprotective, anxiolytic and anti-convulsant effects, which may be effective in preventing additional brain damage in persons with AUDs, while simultaneously decreasing the frequency of relapses.

Dystonia is a neurological movement disorder, with many known causes, and characterized by involuntary, continual muscular contractions causing twisting and repetitive movements or abnormal postures. Cannabinoids have been shown to reduce the symptoms of muscular contractions characterizing this disorder.

The etiological pathology of many diseases relates to the inflammatory processes caused by an individual's immune system. The inflammation may result from (1) an otherwise appropriate immunoresponse to an outside trauma, such as brain swelling secondary to a closed head injury; (2) an overactive immunoresponse such as with an allergic reaction or dermatitis; or (3) an inappropriate auto-immunoresponse such as what causes certain forms of multiple sclerosis, inflammatory bowel disorders and arthritis. Regardless of the underlying cause of the inflammation, it is therapeutically desirable under these circumstances to regulate to the immune system and lessen the inflammatory response. Cannabinoids have been shown to regulate various steps in the immune response and have shown some therapeutic benefit in treatment of certain inflammatory diseases such as dermatitis and psoriasis.

Rheumatoid arthritis affects approximately 0.5-1% of the United States population, and autoimmune diseases in general affect more than 20 million Americans. The pain associated with rheumatoid arthritis can often be disabling. Cannabinoids, such as $\Delta^9$-THC, have been found to be useful as adjunct treatment for rheumatoid arthritis and joint pain secondary to other autoimmune diseases, such as inflammatory bowel disease, multiple sclerosis and systemic lupus erythematosus.

Chronic abusers of cannabis can develop dependence and experience withdrawal symptoms when they attempt to discontinue use of the drug. Collectively cannabis dependence and withdrawal are referred to herein as cannabis use disorders. It is known in the skill of the art that cannabinoids, including $\Delta^9$-THC, are useful in the treating cannabis use disorders.

In addition to the above-discussed therapeutics benefits, cannabinoids such as $\Delta^9$-THC, and $\Delta^9$-THC prodrugs, offer a variety of pharmacological benefits, including, but not limited to, anti-inflammatory, anti-convulsant, anti-psychotic, anti-oxidant, neuroprotective, substitution therapy for marijuana abuse and immunomodulatory effects.

Given the therapeutic benefit, it would be advantageous to develop a composition in which $\Delta^9$-THC is delivered systemically to achieve a therapeutically effective dose. Unfortunately, as with the other cannabinoids, $\Delta^9$-THC undergoes substantial first-pass metabolism when absorbed from the human gut after oral administration. Further, the oral bioavailability of any $\Delta^9$-THC-containing product is further diminished when a patient suffers from nausea or emesis, as they avoid either taking their oral medication or the oral dosage form does not remain in their gastro-intestinal tract for a sufficient time to achieve a therapeutic dose. Additionally, due to its highly hydrophobic nature, $\Delta^9$-THC is poorly absorbed through membranes such as the skin of a mammal, such as a human. Therefore, the success of transdermally administering therapeutically effective quantities of $\Delta^9$-THC to a mammal in need of such treatment within a reasonable time frame and over a suitable surface area has been substantially limited.

Therefore, in view of the foregoing, it would be desirable to deliver therapeutically effective amounts of $\Delta^9$-THC to a mammal in need thereof for the treatment of one or more medical conditions, such as pain, nausea or appetite stimulation, by a route of administration that does not depend upon absorption from the gastrointestinal tract of the mammal and not subject to first-pass metabolism upon absorption from the gastrointestinal tract. One such route of administration for the systemic delivery of $\Delta^9$-THC is transdermal.

Unfortunately, due to its highly hydrophobic nature, $\Delta^9$-THC is poorly absorbed through membranes such as the skin of a mammal, such as a human. Therefore, the success of transdermally administering therapeutically effective quantities of $\Delta^9$-THC to a mammal in need of such treatment within a reasonable time frame and over a suitable surface area has been substantially limited.

The epidermis and dermis of many mammals, such as humans and guinea pigs, contains enzymes which are capable of metabolizing active pharmaceutical agents which pass through the stratum corneum. The metabolic process occurring in the skin of mammals, such as humans, can be utilized to deliver pharmaceutically effective quantities of $\Delta^9$-THC to a mammal in need thereof. Described herein are prodrugs of $\Delta^9$-THC that can be transdermally administered to a mammal, such as a human, so that the metabolic product resulting from metabolism in the skin is $\Delta^9$-THC which is systemically available for the treatment of a medical condition such as pain, nausea or appetite stimulation. Also described herein are compositions comprising $\Delta^9$-THC prodrugs suitable for transdermal delivery to a mammal in need thereof and methods of using $\Delta^9$-THC prodrugs.

Therefore, a significant advancement in the art would occur if a prodrug of $\Delta^9$-THC capable of transdermal delivery, compositions suitable for transdermal delivery comprising prodrugs of $\Delta^9$-THC and methods of using prodrugs of $\Delta^9$-THC could be developed whereby the resulting metabolic product was $\Delta^9$-THC which is systemically available to a mammal in a therapeutically effective amount.

In addition, pharmaceutical compositions can be systemically administered by other means, including: oral, buccal, sublingual, injection, rectal, vaginal and intranasal. The metabolic process occurring in mammals, such as humans, can also be utilized to deliver pharmaceutically effective quantities of $\Delta^9$-THC to the systemic circulation of a mammal in need thereof. Described herein are prodrugs of $\Delta^9$-THC that can be administered to a mammal, such as a human, so that the metabolic product resulting from metabolism in the skin is $\Delta^9$-THC which is available for the treatment of a medical condition such as pain, nausea or appetite stimulation. Also described herein are compositions comprising $\Delta^9$-THC prodrugs suitable for delivery to a mammal in need thereof and methods of using $\Delta^9$-THC prodrugs.

Therefore, a significant advancement in the art would occur if one could develop a prodrug of $\Delta^9$-THC capable of oral, buccal, sublingual, injectable, topical, follicular, nasal, ocular, rectal or vaginal delivery; compositions suitable for oral, buccal, sublingual, injectable, topical, follicular, nasal, ocular, rectal, vaginal delivery comprising prodrugs of $\Delta^9$-THC; and methods of using prodrugs of $\Delta^9$-THC whereby the resulting metabolic product was $\Delta^9$-THC which is systemically available to a mammal in a therapeutically effective amount.

In addition to the benefits of systemically administered $\Delta^9$-THC discussed above, cannabinoids, including $\Delta^9$-THC, have been found to have localized benefits from topical administration. For example, topically administered cannabinoids have been found to be useful to alleviate pain and other conditions originating near the surface of the skin, including but not limited to pain associated with post-herpetic neuralgia, shingles, burns, actinic keratosis, oral cavity sores and ulcers, post-episiotomy pain, psoriasis, pruritis, contact dermatitis, eczema, bullous dermatitis herpetiformis, exfoliative dermatitis, mycosis fungoides, pemphigus, severe erythema multiforme (e.g., Stevens-Johnson syndrome), seborrheic dermatitis and psoriatic arthritis. In addition, topically administered cannabinoids have been found to be useful to alleviate pain and other conditions associated with deeper tissues, such as peripheral neuropathic pain, including but not limited to the peripheral neuropathic pain associated with diabetic neuropathy, ankylosing spondylitis, Reiter's syndrome, gout, chondrocalcinosis, joint pain secondary to dysmenorrhea, fibromyalgia, musculoskeletal pain, neuropathic-postoperative complications, polymyositis, acute nonspecific tenosynovitis, bursitis, epicondylitis, post-traumatic osteoarthritis, synovitis, and juvenile rheumatoid arthritis. When cannabinoids are administered topically to treat pain and other conditions associated with deeper tissues, including peripheral neuropathic pain, it maybe useful to co-administer cannabinoids systemically.

In order to achieve these local benefits, it is advantageous for $\Delta^9$-THC or a prodrug thereof to penetrate the stratum corneum but not be absorbed systemically. In such a case, the $\Delta^9$-THC would concentrate in the skin and/or pilosebaceous unit, thus maximizing its local effect. Not only does the localized effect increase the potential therapeutic benefit, it lessens the frequency and severity of side-effects associated with cannabinoid administration because the amount of active compound circulating in the patient is minimized. The $\Delta^9$-THC can be incorporated into a prodrug with an active moiety that would improve the appearance and/or hydration of the skin.

Therefore, a significant advancement in the art would occur with the development of a $\Delta^9$-THC prodrug capable of topical delivery, such that it penetrates the outer layer of the skin but is not absorbed into circulation; compositions suitable for topical delivery comprising prodrugs of $\Delta^9$-THC and methods of using prodrugs of $\Delta^9$-THC whereby the resulting metabolic product was $\Delta^9$-THC which is available at the site of administration in a mammal in a therapeutically effective amount but is not absorbed systemically.

SUMMARY

Described herein are prodrugs of $\Delta^9$-THC, methods of making prodrugs of $\Delta^9$-THC, compositions comprising prodrugs of $\Delta^9$-THC and methods of using prodrugs of $\Delta^9$-THC.

Other embodiments, objects, features and advantages will be set forth in the detailed description of the embodiments that follows, and in part will be apparent from the description, or may be learned by practice, of the claimed invention. These objects and advantages will be realized and attained by the processes and compositions particularly pointed out in the written description and claims hereof. The foregoing Summary has been made with the understanding that it is to be considered as a brief and general synopsis of some of the embodiments disclosed herein, is provided solely for the benefit and convenience of the reader, and is not intended to limit in any manner the scope, or range of equivalents, to which the appended claims are lawfully entitled.

BRIEF DESCRIPTION OF THE DRAWINGS

FIG. 10 is a table of $\Delta^9$-Tetrahydrocannabinol and $\Delta^9$-tetrahydrocannabinol prodrugs Log P values. The Log P values represent the water/octanol partition coefficient and are calculated ChemSketch version 10.02 (Advanced Chemistry Development; Toronto, Ontario, Canada).

DESCRIPTION

Figure 1:
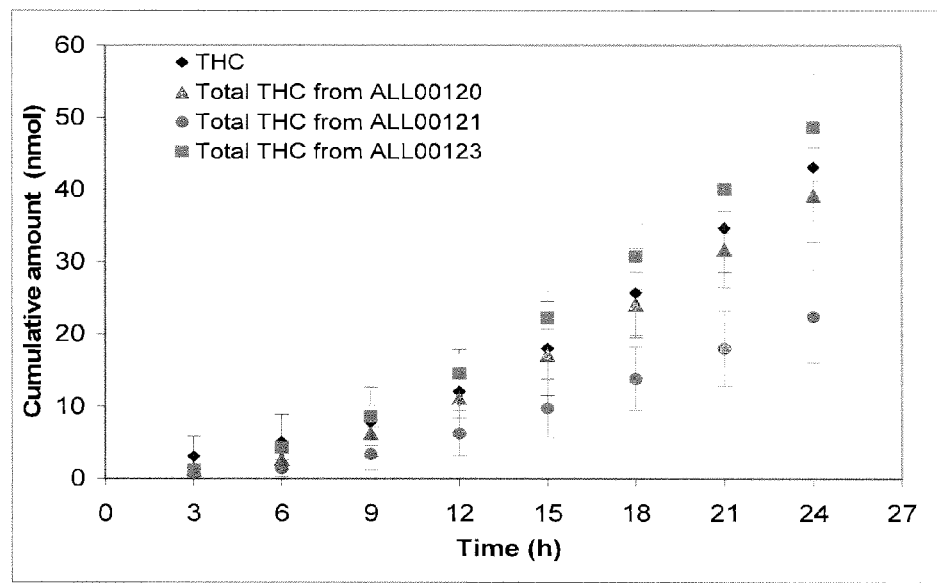
FIG. 1 is a plot of the representative permeation profile of $\Delta^9$-tetrahydrocannabinol (n=2), ALL00120 (n=3), ALL00121 (n=2) and ALL00123 (n=3) with 2.36:1.18:1 PG(propylene glycol):ethanol:$H_2O$ donor solution, wherein "n" is the number of samples tested.
Figure 2:
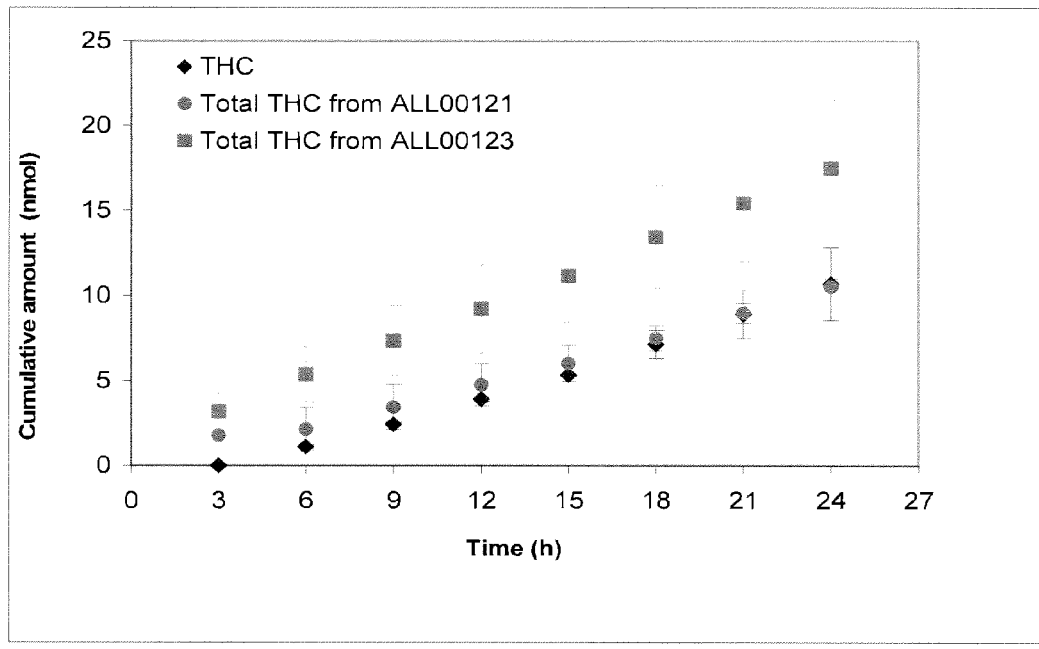
FIG. 2 is a plot of the representative permeation profile of $\Delta^9$-tetrahydrocannabinol (n=2), ALL00121 (n=2) and ALL00123 (n=3) with gel formulation, wherein "n" is the number of samples tested.
Figure 3:
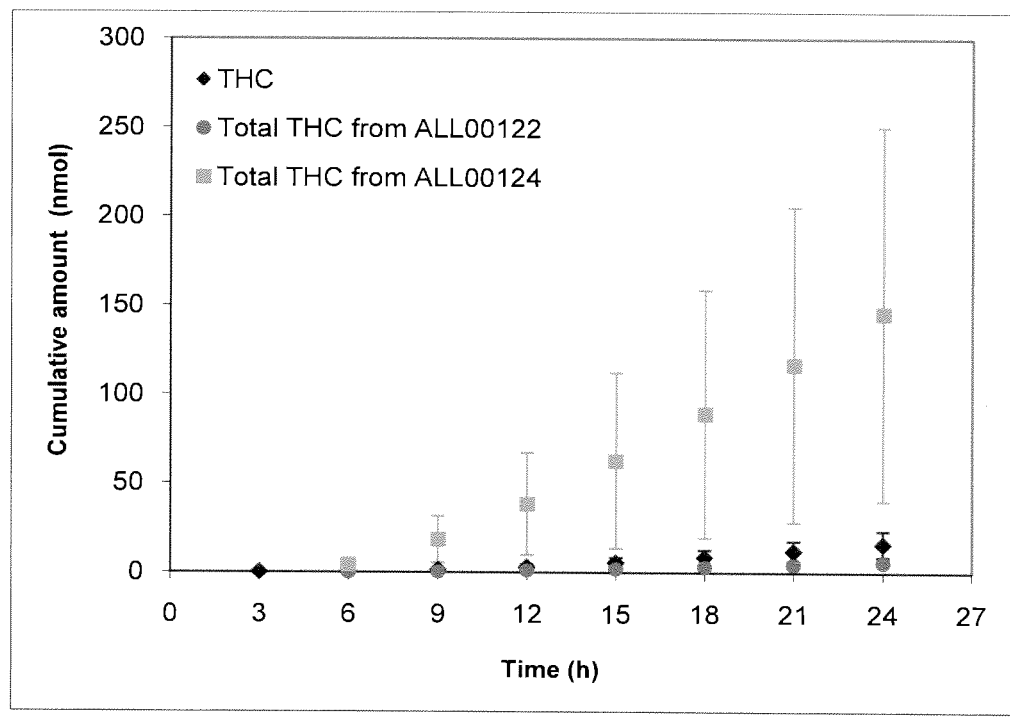
FIG. 3 is a plot of the representative permeation profile of $\Delta^9$-tetrahydrocannabinol (n=2), ALL00122 (n=2), and ALL00124 (n=2) with 2.36:1.18:1 pH=5.5 PG(propylene glycol):ethanol:$H_2O$ donor solution, wherein "n" is the number of samples tested.
Figure 4:
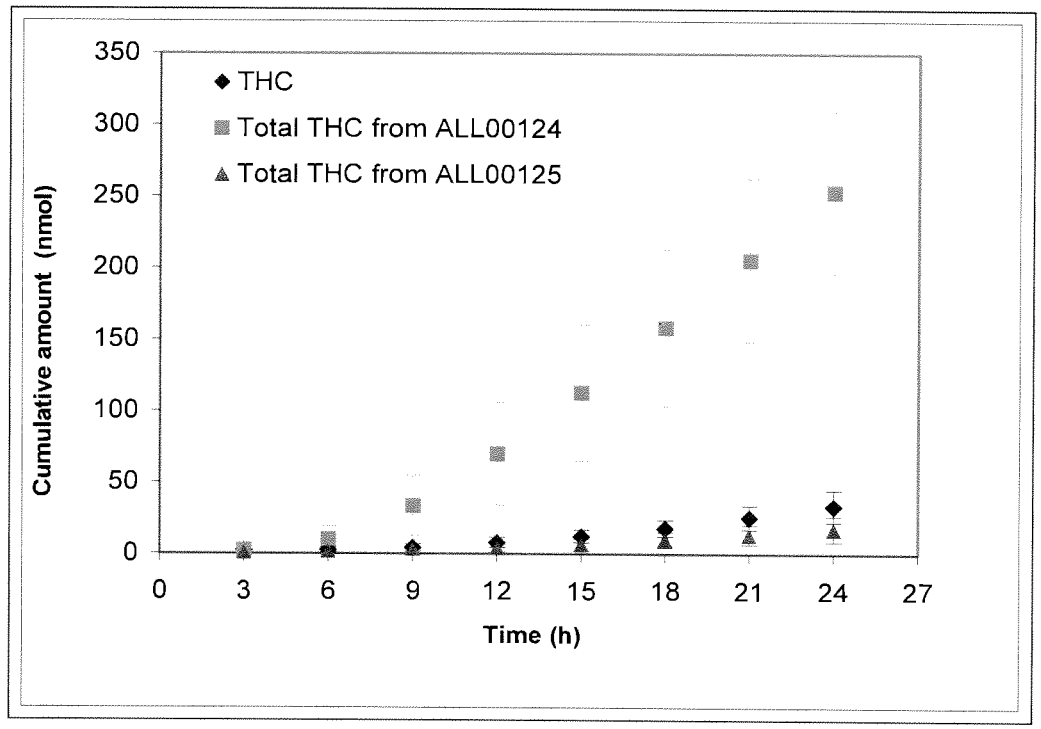
FIG. 4 is a plot of the representative permeation profile of $\Delta^9$-tetrahydrocannabinol (n=3), ALL00124 (n=2), and ALL00125 (n=3) with 2.36:1.18:1 pH=5.5 PG(propylene glycol):ethanol:$H_2O$ donor solution, wherein "n" is the number of samples tested.
Figure 5:
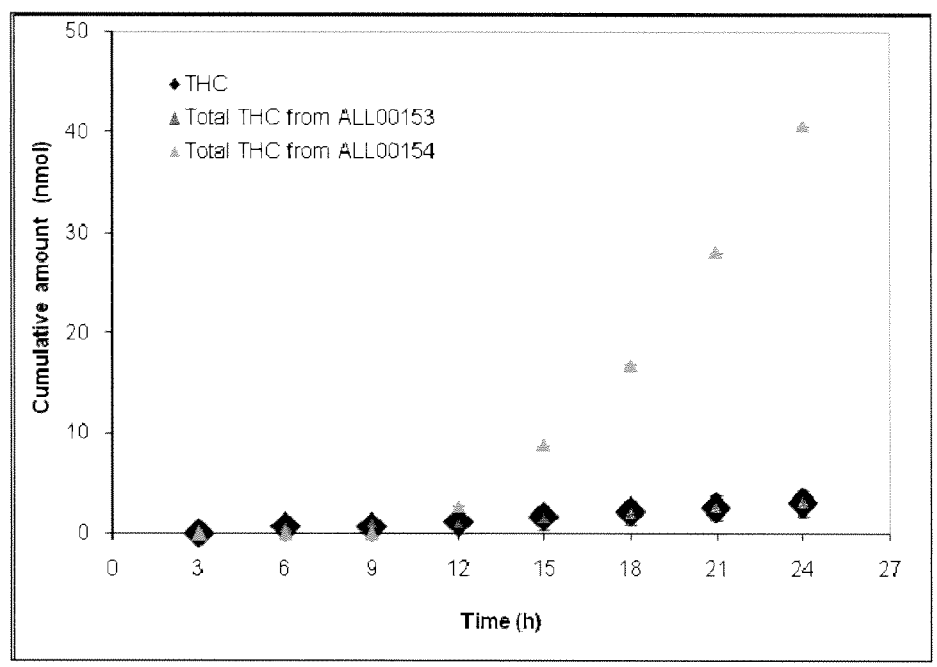
FIG. 5 is a plot of the representative permeation profile of $\Delta^9$-tetrahydrocannabinol (n=3), ALL00153 (n=3), and ALL00154 (n=1) with gel formulation, wherein "n" is the number of samples tested.
Figure 6:
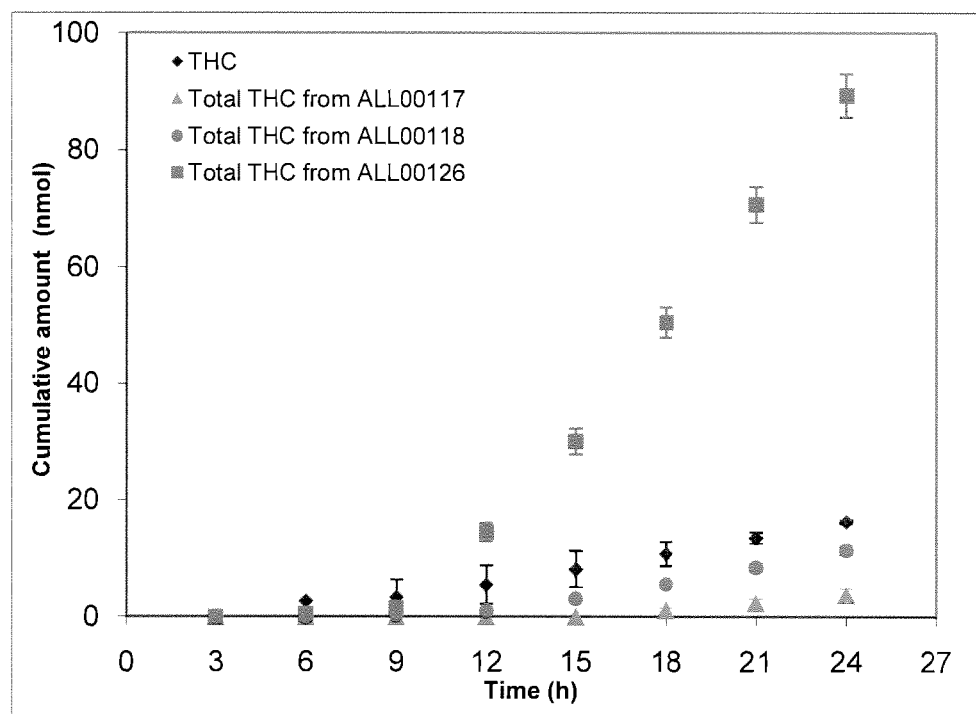
FIG. 6 is a plot of the representative permeation profile of $\Delta^9$-tetrahydrocannabinol (n=2), ALL00117 (n=3), ALL00118 (n=3) and ALL00126 (n=2) with 90:8:2 PG(propylene glycol):H2O:IPM donor solution, wherein "n" is the number of samples tested.
Figure 7:
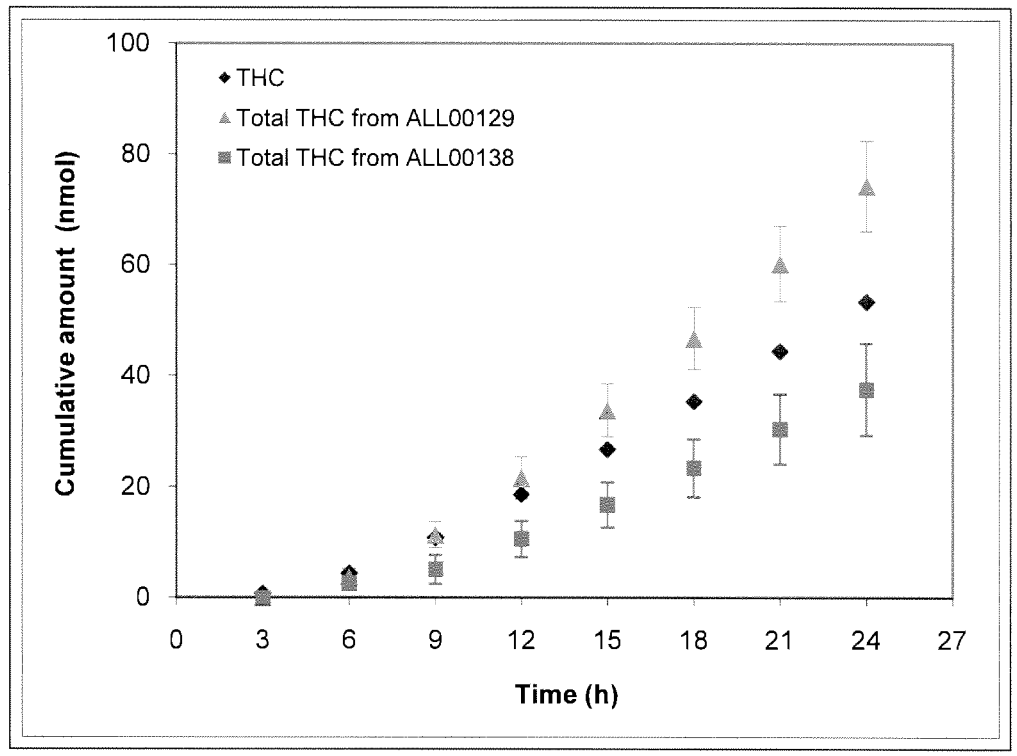
FIG. 7 is a plot of the representative permeation profile of $\Delta^9$-tetrahydrocannabinol (n=1), ALL00129 (n=3), and ALL00138 (n=2) with 90:8:2 PG(propylene glycol):H2O:IPM donor solution, wherein "n" is the number of samples tested.
Figure 8:
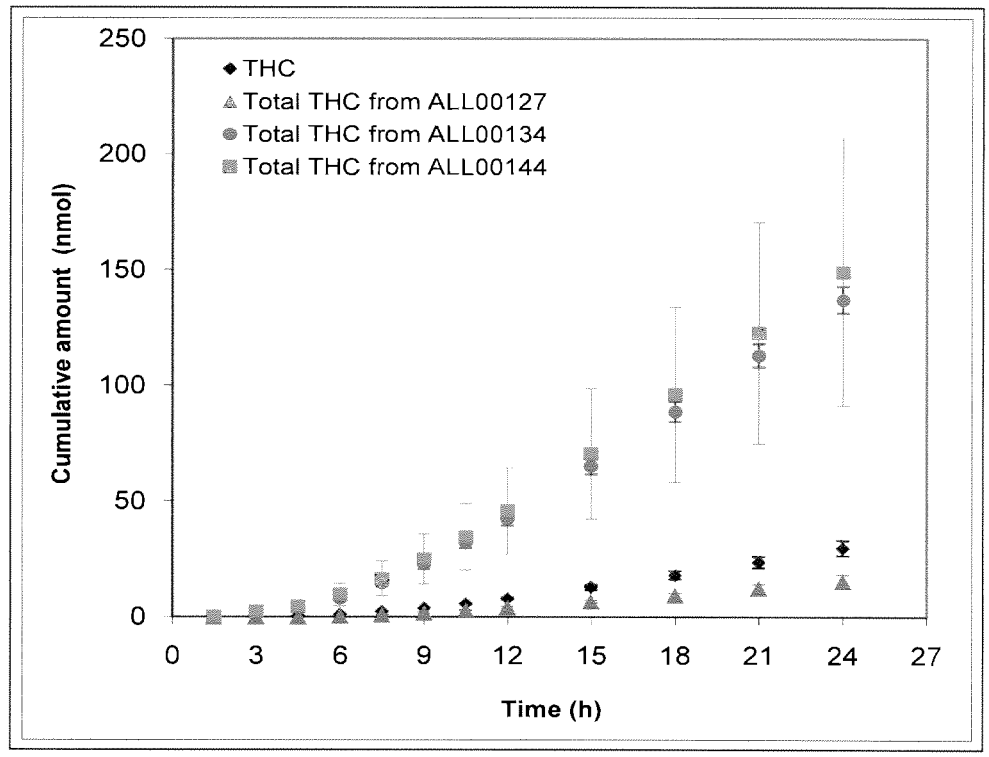
FIG. 8 is a plot of the representative permeation profile of $\Delta^9$-tetrahydrocannabinol (n=2), ALL00127 (n=3), ALL00134 (n=3), and ALL00144 (n=2) with 90:8:2 PG(propylene glycol):H2O:IPM donor solution, wherein "n" is the number of samples tested.
Figure 9:
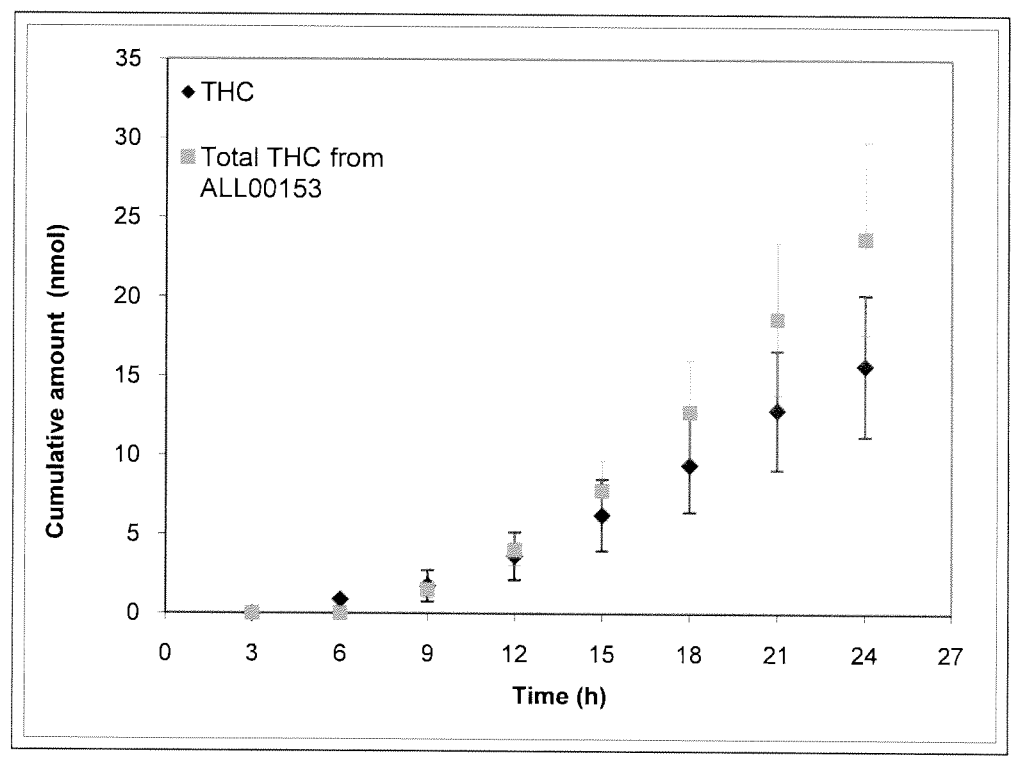
FIG. 9 is a plot of the representative permeation profile of $\Delta^9$-tetrahydrocannabinol (n=2) and ALL00153 (n=3) in 90:8:2 PG(propylene glycol):$H_2O$:IPM donor solution, wherein "n" is the number of samples tested.

While the present invention is capable of being embodied in various forms, the description below of several embodiments is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way. Embodiments illustrated under any heading may be combined with embodiments illustrated under any other heading.

Compounds described herein include pharmaceutically acceptable prodrugs of $\Delta^9$-THC. One embodiment described herein includes pharmaceutically acceptable prodrugs of $\Delta^9$-THC which are suitable for transdermal administration and are metabolized to $\Delta^9$-THC. A further embodiment includes pharmaceutically acceptable prodrugs of $\Delta^9$-THC which are suitable for any route of administration. The pharmaceutically acceptable prodrugs of $\Delta^9$-THC may be in any suitable form for administration to a mammal such as in the form of a free base, free acid, salt, ester, hydrate, anhydrate, amide, enantiomer, isomer, tautomer, polymorph, derivative, or the like, provided that the free base, salt, ester, hydrate, anhydrate, amide, enantiomer, isomer, tautomer, or any other pharmacologically suitable derivative is therapeutically active or undergoes conversion within or outside of the body to a therapeutically active form of $\Delta^9$-THC.

Compositions described herein comprise at least one pharmaceutically acceptable prodrug of $\Delta^9$-THC. The pharmaceutically acceptable prodrugs of $\Delta^9$-THC may be in any suitable form for administration to a mammal such as in the form of a free base, free acid, salt, ester, hydrate, anhydrate, amide, enantiomer, isomer, tautomer, polymorph, derivative, or the like, provided that the free base, salt, ester, hydrate, anhydrate, amide, enantiomer, isomer, tautomer, or any other pharmacologically suitable derivative is therapeutically active or undergoes conversion within or outside of the body to a therapeutically active form of $\Delta^9$-THC.

Compositions described herein include those which are suitable for transdermal, oral, buccal, sublingual, injectable, follicular, topical, nasal, ocular, rectal or vaginal administration of prodrugs of $\Delta^9$-THC. The compositions described herein optionally include a vehicle or carrier for the transdermal administration of a prodrug of $\Delta^9$-THC as well as optionally including solvents, thickening agents, penetration enhancers, wetting agents, lubricants, emollients, substances added to mask or counteract a disagreeable odor, fragrances, and substances added to improve appearance or texture of the composition.

The term prodrug as used herein refers to a compound that undergoes a chemical conversion, through a metabolic process or otherwise within the body of the mammal receiving the compound, into its active form that has medical effects.

In one embodiment, illustrative $\Delta^9$-THC prodrugs include those compounds of Formula (I):

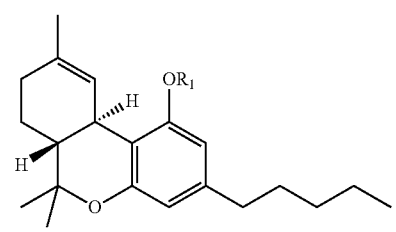

FORMULA I wherein

R$_1$ is comprised of a bio-labile linker (e.g. ester, oxygenated ester, oxaester, pegylated ester, hydroxylated ester, branched hydroxylated ester, succinic acid monoester, oxalic acid mixed pegylated ester, amino ester, cyclic amino ester, acylated amino ester, carbonate, oxygenated carbonate, oxacarbonate, pegylated carbonate, hydroxylated carbonate, branched hydroxylated carbonate, aminoalkyl carbonate, cyclic aminoalkyl carbonate, acylated aminoalkyl carbonate, hydroxycarbonylalkyl carbonate, carbamate, alkyl carbamate, aminoalkyl carbamate, acylated aminoalkyl carbamate, cyclic aminoalkyl carbamate, oxacarbamate, pegylated carbamate, hydroxylated carbamate, branched hydroxylated carbamate, hydroxycarbonylalkyl carbamate, phosphate, diphosphate, triphosphate or other suitable bio-labile linking structure) and further comprising moieties which can be selected in order to control the rate and extent of absorption and metabolism, such as transdermal absorption and metabolism. Several options for R$_1$ are disclosed herein. Also included herein is the free acid, free base, salt, ester, hydrated forms, anhydrous, amide, enantiomer, isomer, tautomer, polymorph, or derivative thereof of compounds of Formula I.

Additional embodiments contemplated by the present disclosure include, but are not limited to, those described in WO2007044215, WO2007035945, US2007066657, WO2007026215, WO2007020502, WO2007017264, WO2007009720, US2007004772, US2006287324, US2006287323, US2006287342, US2006287341, US2006089378, US2006079556, US2005143441, U.S. Pat. No. 7,109,216, US2004235854, US2005267161, US2005054659, US2007099990, US2006122229, US2006122230, US2004077650, U.S. Pat. No. 6,974,810, US2004248944, U.S. Pat. No. 6,977,266 and US2006052411 and U.S. patent application Ser. No. 10/032,163.

"Pharmaceutically acceptable salts," or "salts," include the salt of a Δ$^9$-THC prodrug suitable for administration to a mammal and includes those prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic, methanesulfonic, ethanesulfonic, benzenesulfonic, pantothenic, toluenesulfonic, 2-hydroxyethanesulfonic, sulfanilic, cyclohexylaminosulfonic, algenic, beta.-hydroxybutyric, galactaric and galacturonic acids. The following list of pharmaceutically acceptable salts is not meant to be exhaustive but merely illustrative as person of ordinary skill in the art would appreciate that other pharmaceutically acceptable salts of Δ$^9$-THC and prodrugs of Δ$^9$-THC may be prepared.

In one embodiment, acid addition salts are prepared from the free base forms using conventional methodology involving reaction of the free base with a suitable acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. The following list of organic and inorganic acids is not meant to be exhaustive but merely illustrative as person of ordinary skill in the art would appreciate that other acids may be used to create pharmaceutically acceptable salts of Δ$^9$-THC and prodrugs of Δ$^9$-THC. In other embodiments, an acid addition salt is reconverted to the free base by treatment with a suitable base. In still other embodiments, the basic salts are alkali metal salts, e.g., sodium salt.

In one embodiment, R$_1$ is an ester. The preparation of Δ$^9$-THC esters involves functionalizing the hydroxyl group that is present within the molecular structure of Δ$^9$-THC. In another embodiment, the ester of R$_1$ is oxygenated. In another embodiment, R$_1$ is an oxygenated ester which is an oxaester. In another embodiment, R$_1$ is an oxaester which is pegylated. In further embodiments, R$_1$ is a pegylated oxaester that can have 1 ethylene glycol repeat unit, 2 ethylene glycol repeat units, 3 ethylene glycol repeat units, 4 ethylene glycol repeat units, 5 ethylene glycol repeat units, 6 ethylene glycol repeat units, 7 ethylene glycol repeat units, 8 ethylene glycol repeat units, 9 ethylene glycol repeat units, 10 ethylene glycol repeat units, 11 ethylene glycol repeat units, 12 ethylene glycol repeat units, 13 ethylene glycol repeat units, 14 ethylene glycol repeat units and 15 ethylene glycol repeat units. In a further embodiment, R$_1$ is an ester which is hydroxylated. In a further embodiment, R$_1$ is a branched hydroxylated ester. In a further embodiment, R$_1$ is ester which is an alkyl ester. In additional embodiments, R$_1$ is an alkyl ester having 1 alkyl carbon, 2 alkyl carbons, 3 alkyl carbons, 4 alkyl carbons, 5 alkyl carbons, 6 alkyl carbons, 7 alkyl carbons, 8 alkyl carbons, 9 alkyl carbons, 10 alkyl carbons, 11 alkyl carbons, 12 alkyl carbons, 13 alkyl carbons, 14 alkyl carbons and 15 alkyl carbons.

In other embodiments, R$_1$ is an ester which is an amino ester having 1 amino group, 2 amino groups, 3 amino groups, 4 amino groups and 5 amino groups. In another embodiment, R$_1$ is an amino ester which is aminoalkyl ester. In another embodiment, R$_1$ is an amino ester which is cyclic amino ester. In a further embodiment, R$_1$ is an aminoalkyl ester having 1 amino group, 2 amino groups, 3 amino groups, 4 amino groups and 5 amino groups and having 1 alkyl carbon, 2 alkyl carbons, 3 alkyl carbons, 4 alkyl carbons, 5 alkyl carbons, 6 alkyl carbons, 7 alkyl carbons, 8 alkyl carbons, 9 alkyl carbons, 10 alkyl carbons, 11 alkyl carbons, 12 alkyl carbons, 13 alkyl carbons, 14 alkyl carbons and 15 alkyl carbons. In another embodiment, R$_1$ is an amino ester which is an acylated amino ester. In a further embodiment, R$_1$ is a succinic acid monoester. In a further embodiment, R$_1$ is an oxalic acid mixed pegylated ester.

In one embodiment, R$_1$ is a carbamate. The preparation of Δ$^9$-THC carbamates involves functionalizing the hydroxyl group that is present within the molecular structure of Δ$^9$-THC. In a further embodiment, R$_1$ is a carbamate which is an alkyl carbamate. In additional embodiments, R$_1$ is an alkyl carbamate having 1 alkyl carbon, 2 alkyl carbons, 3 alkyl carbons, 4 alkyl carbons, 5 alkyl carbons, 6 alkyl carbons, 7 alkyl carbons, 8 alkyl carbons, 9 alkyl carbons, 10 alkyl carbons, 11 alkyl carbons, 12 alkyl carbons, 13 alkyl carbons, 14 alkyl carbons and 15 alkyl carbons. In other embodiments, R$_1$ is a carbamate which is an amino carbamates having 1 amino group, 2 amino groups, 3 amino groups, 4 amino groups and 5 amino groups. In another embodiment, $R_1$ is an amino carbamate which is an alkylamino carbamate. In a further embodiment, $R_1$ is an alkylamino carbamate having 1 amino group, 2 amino groups, 3 amino groups, 4 amino groups and 5 amino groups and independently having 1 alkyl carbon, 2 alkyl carbons, 3 alkyl carbons, 4 alkyl carbons, 5 alkyl carbons, 6 alkyl carbons, 7 alkyl carbons, 8 alkyl carbons, 9 alkyl carbons, 10 alkyl carbons, 11 alkyl carbons, 12 alkyl carbons, 13 alkyl carbons, 14 alkyl carbons and 15 alkyl carbons. In an additional embodiment, $R_1$ is a cyclic aminoalkyl carbamate. In another embodiment, $R_1$ is a carbamate that is oxygenated. In another embodiment, $R_1$ is an oxygenated carbamate which is an oxacarbamate. In another embodiment, $R_1$ is an oxacarbamate that is pegylated. In further embodiments, $R_1$ is a pegylated oxacarbamate that can have 1 ethylene glycol repeat unit, 2 ethylene glycol repeat units, 3 ethylene glycol repeat units, 4 ethylene glycol repeat units, 5 ethylene glycol repeat units, 6 ethylene glycol repeat units, 7 ethylene glycol repeat units, 8 ethylene glycol repeat units, 9 ethylene glycol repeat units, 10 ethylene glycol repeat units, 11 ethylene glycol repeat units, 12 ethylene glycol repeat units, 13 ethylene glycol repeat units, 14 ethylene glycol repeat units and 15 ethylene glycol repeat units. In a further embodiment, $R_1$ is a carbamates which is hydroxylated. In a further embodiment, $R_1$ is a branched hydroxylated carbamate. In another embodiment, $R_1$ is a hydroxycarbonyl carbamate.

In one embodiment, $R_1$ is a carbonate. The preparation of $\Delta^9$-THC carbonates involves functionalizing the hydroxyl group that is present within the molecular structure of $\Delta^9$-THC. In another embodiment, the carbonate of $R_1$ is oxygenated. In another embodiment, $R_1$ is an oxygenated carbonate which is an oxacarbonate. In another embodiment, $R_1$ is an oxacarbonate which is pegylated. In further embodiments, $R_1$ is a pegylated oxacarbonate that can have 1 ethylene glycol repeat unit, 2 ethylene glycol repeat units, 3 ethylene glycol repeat units, 4 ethylene glycol repeat units, 5 ethylene glycol repeat units, 6 ethylene glycol repeat units, 7 ethylene glycol repeat units, 8 ethylene glycol repeat units, 9 ethylene glycol repeat units, 10 ethylene glycol repeat units, 11 ethylene glycol repeat units, 12 ethylene glycol repeat units, 13 ethylene glycol repeat units, 14 ethylene glycol repeat units and 15 ethylene glycol repeat units. In a further embodiment, $R_1$ is a carbonate which is hydroxylated. In a further embodiment, $R_1$ is a carbonate which is hydroxylated. In a further embodiment, $R_1$ is a branched hydroxylated carbonate. In another embodiment, $R_1$ is a hydroxycarbonyl carbonate. In other embodiments, $R_1$ is a carbonate which is an amino carbonates having 1 amino group, 2 amino groups, 3 amino groups, 4 amino groups and 5 amino groups. In another embodiment, $R_1$ is an amino carbonates which are alkylamino carbonates. In a further embodiment, $R_1$ is an aminoalkyl carbonate having 1 amino group, 2 amino groups, 3 amino groups, 4 amino groups and 5 amino groups and independently having 1 alkyl carbon, 2 alkyl carbons, 3 alkyl carbons, 4 alkyl carbons, 5 alkyl carbons, 6 alkyl carbons, 7 alkyl carbons, 8 alkyl carbons, 9 alkyl carbons, 10 alkyl carbons, 11 alkyl carbons, 12 alkyl carbons, 13 alkyl carbons, 14 alkyl carbons and 15 alkyl carbons.

In one embodiment, $R_1$ is a phosphate. The preparation of $\Delta^9$-THC phosphates involves functionalizing the hydroxyl group that is present within the molecular structure of $\Delta^9$-THC. In this case, the $\Delta^9$-THC phosphate was isolated in the form of ammonium salt. However, those skilled in the art can convert $\Delta^9$-THC phosphate to a salt of a pharmaceutically acceptable amine. In addition, those skilled in the art can prepare salts in a different phosphate:amine ratio. As illustrated in the structure below, the $\Delta^9$-THC phosphate would have a structure of:

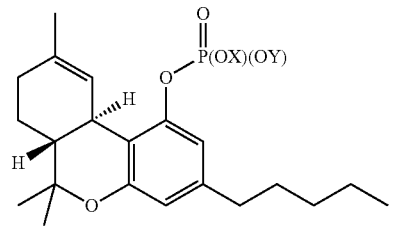

FORMULA II wherein X and Y, can be same or different, and are selected from a group consisting of: hydrogen, salt-forming cations including alkali metals (e.g., sodium and potassium), alkaline earth metals (e.g., calcium and magnesium); and cations of pharmaceutically acceptable organic bases (e.g., quaternated or protonated amines, including alkylamines, hydroxyalkylamines, monoamines, diamines and naturally occurring amines). Examples of such pharmaceutically acceptable organic bases include choline, betaine, caffeine, N, N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, hydrabamine, isopropylamine, methylglucamine, morpholine, piperidine, polyamine resins, procaine, purines, theobromine, triethylamine, trimethylamine, tripropylamine, tromethamine, tetramethylammonium hydroxide, benzyltrimethylammonium hydroxide, tris(hydroxymethyl)aminomethane (TRIS), N-(2-hydroxyethyl)pyrrolidine, piperazine, glucosamine, arginine, lysine and histidine. In a further embodiment, X and Y are different substituent groups. In another embodiment, X and Y are the same substituent group. In a further embodiment, X and Y can both be part of the same functional group, such as piperazine.

In a further embodiment, the phosphate is selected from a group consisting of a diphosphate and triphosphate. In another embodiment, the compound is the salt form of the di or tri phosphate.

Additional embodiments of Formula I include:

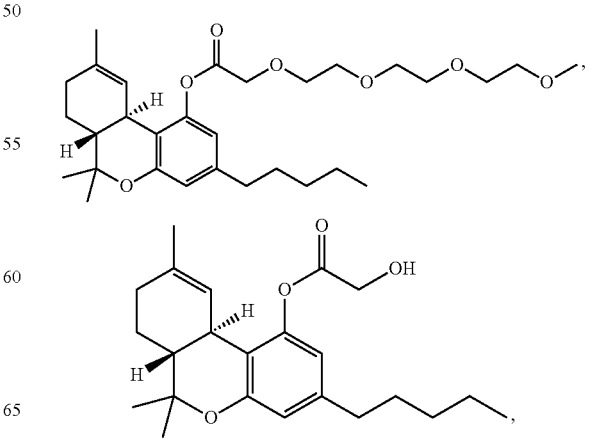

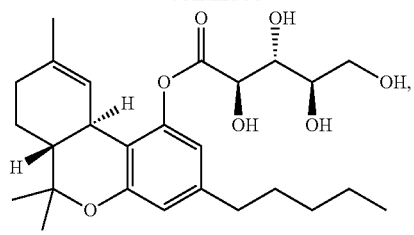
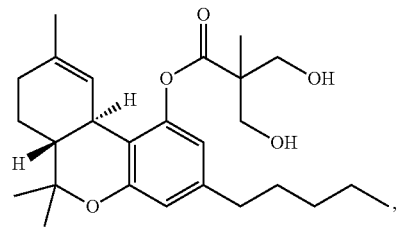
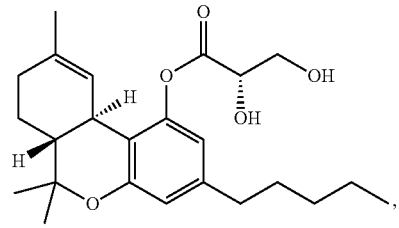
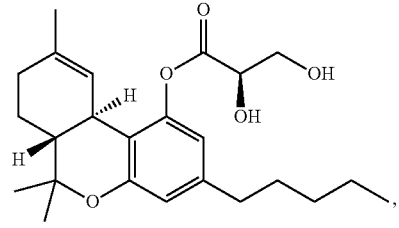
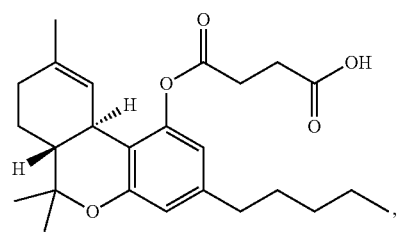
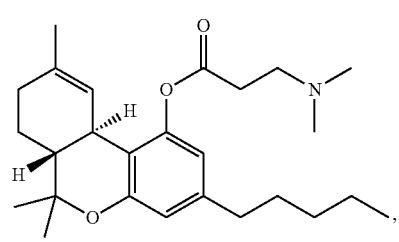
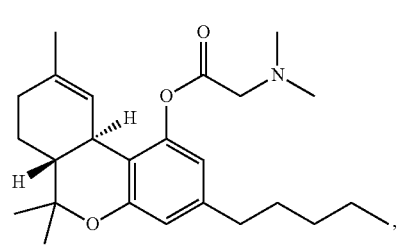
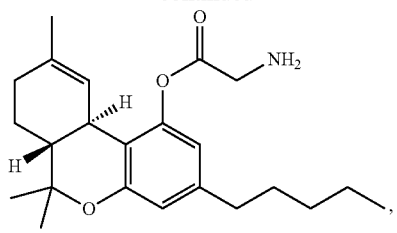
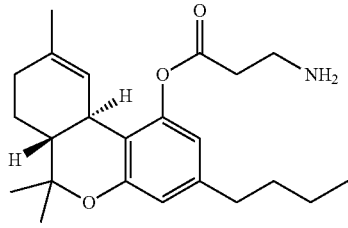
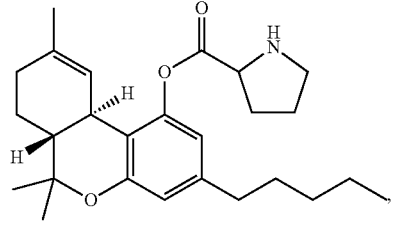
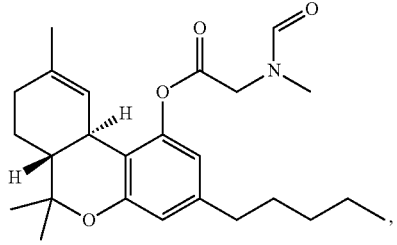
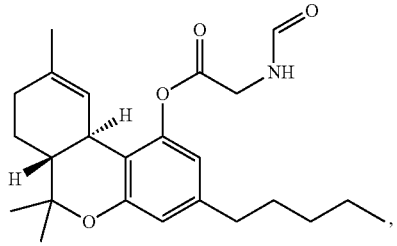
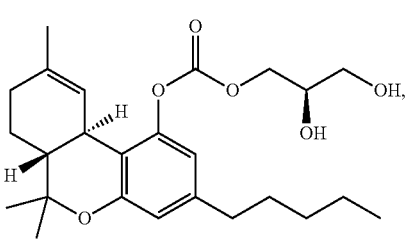
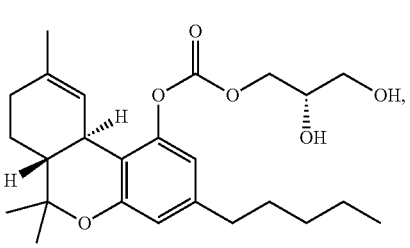

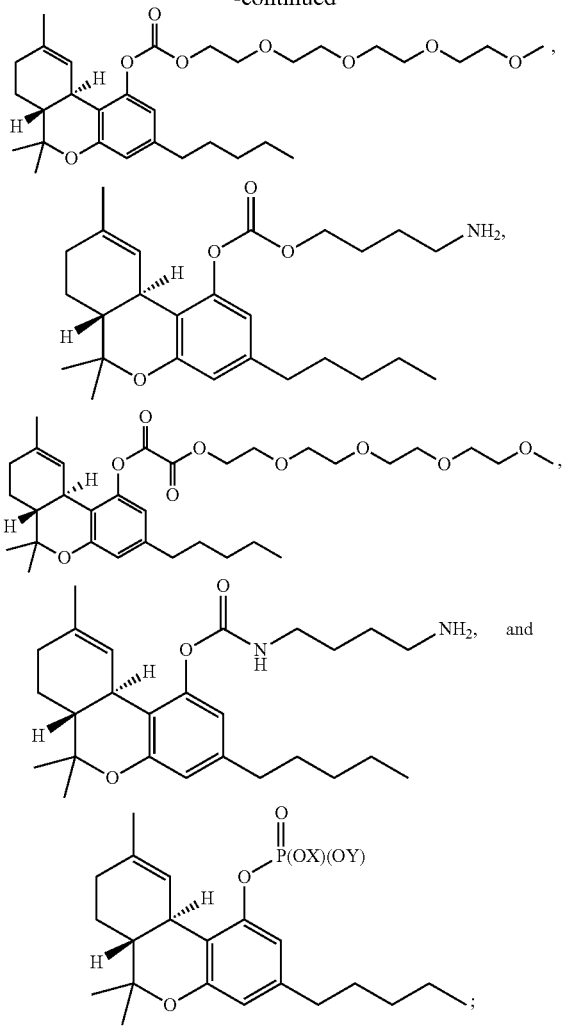

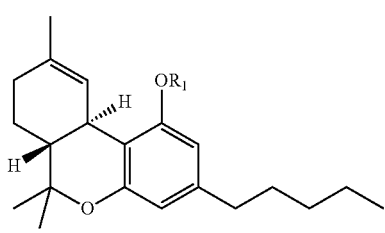

wherein X and Y is selected from a group consisting of: hydrogen, salt-forming cations including alkali metals, alkaline earth metals, and cations of pharmaceutically acceptable organic bases.

Further embodiments described herein are pharmaceutical compositions comprising:
(a) a Δ⁹-THC prodrug selected from the group consisting of:

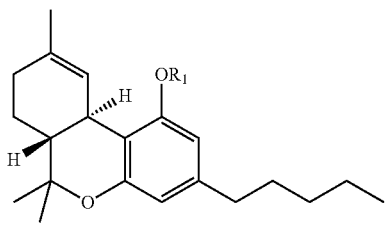

wherein $R_1$ is selected from ester, oxygenated ester, oxaester, pegylated ester, hydroxylated ester, branched hydroxylated ester, succinic acid monoester, oxalic acid mixed pegylated ester, amino ester, cyclic amino ester, acylated amino ester, carbonate, oxygenated carbonate, oxacarbonate, pegylated carbonate, hydroxylated carbonate, branched hydroxylated carbonate, aminoalkyl carbonate, cyclic aminoalkyl carbonate, acylated aminoalkyl carbonate, hydroxycarbonylalkyl carbonate, carbamate, alkyl carbamate, aminoalkyl carbamate, acylated aminoalkyl carbamate, cyclic aminoalkyl carbamate, oxacarbamate, pegylated carbamate, hydroxylated carbamate, branched hydroxylated carbamate, hydroxycarbonylalkyl carbamate, dihydrogen phosphate, alkali metal phosphate salt, alkaline earth metal phosphate salt, and phosphate salt of organic base; and
(b) a pharmaceutical excipient.

A method of administering a compound to a mammal comprising the steps of:
(a) combining a compound selected from the group consisting of:

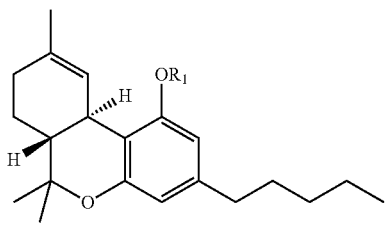

wherein $R_1$ is selected from ester, oxygenated ester, oxaester, pegylated ester, hydroxylated ester, branched hydroxylated ester, succinic acid monoester, oxalic acid mixed pegylated ester, amino ester, cyclic amino ester, acylated amino ester, carbonate, oxygenated carbonate, oxacarbonate, pegylated carbonate, hydroxylated carbonate, branched hydroxylated carbonate, aminoalkyl carbonate, cyclic aminoalkyl carbonate, acylated aminoalkyl carbonate, hydroxycarbonylalkyl carbonate, carbamate, alkyl carbamate, aminoalkyl carbamate, acylated aminoalkyl carbamate, cyclic aminoalkyl carbamate, oxacarbamate, pegylated carbamate, hydroxylated carbamate, branched hydroxylated carbamate, hydroxycarbonylalkyl carbamate, dihydrogen phosphate, alkali metal phosphate salt, alkaline earth metal phosphate salt, and phosphate salt of organic base; and
with a pharmaceutical excipient to form a pharmaceutical composition;
(b) creating a dosage form suitable for administration to a mammal from the pharmaceutical composition; and
(c) administering the dosage form to a mammal.

Additional embodiments include methods of transdermally delivering a Δ⁹-THC prodrug to a mammal comprising the steps of:
(a) selecting a Δ⁹-THC prodrug from the group consisting of:

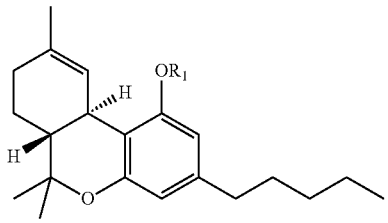

wherein $R_1$ is selected from ester, oxygenated ester, oxaester, pegylated ester, hydroxylated ester, branched hydroxylated ester, succinic acid monoester, oxalic acid mixed pegylated ester, amino ester, cyclic amino ester, acylated amino ester, carbonate, oxygenated carbonate, oxacarbonate, pegylated carbonate, hydroxylated carbonate, branched hydroxylated carbonate, aminoalkyl carbonate, cyclic aminoalkyl carbonate, acylated aminoalkyl carbonate, hydroxycarbonylalkyl carbonate, carbamate, alkyl carbamate, aminoalkyl carbamate, acylated aminoalkyl carbamate, cyclic aminoalkyl carbamate, oxacarbamate, pegylated carbamate, hydroxylated carbamate, branched hydroxylated carbamate, hydroxycarbonylalkyl carbamate, dihydrogen phosphate, alkali metal phosphate salt, alkaline earth metal phosphate salt, and phosphate salt of organic base; and (b) combining the selected $\Delta^9$-THC prodrug with a pharmaceutically acceptable excipient to form a pharmaceutical composition; and (c) contacting the pharmaceutical composition with the skin of a mammal.

A further embodiment described herein is a method of treating a medical condition in a mammal comprising the steps of administering a $\Delta^9$-THC prodrug selected from the group consisting of:

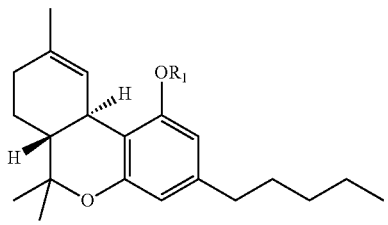

wherein $R_1$ is selected from ester, oxygenated ester, oxaester, pegylated ester, hydroxylated ester, branched hydroxylated ester, succinic acid monoester, oxalic acid mixed pegylated ester, amino ester, cyclic amino ester, acylated amino ester, carbonate, oxygenated carbonate, oxacarbonate, pegylated carbonate, hydroxylated carbonate, branched hydroxylated carbonate, aminoalkyl carbonate, cyclic aminoalkyl carbonate, acylated aminoalkyl carbonate, hydroxycarbonylalkyl carbonate, carbamate, alkyl carbamate, aminoalkyl carbamate, acylated aminoalkyl carbamate, cyclic aminoalkyl carbamate, oxacarbamate, pegylated carbamate, hydroxylated carbamate, branched hydroxylated carbamate, hydroxycarbonylalkyl carbamate, dihydrogen phosphate, alkali metal phosphate salt, alkaline earth metal phosphate salt, and phosphate salt of organic base; and
wherein the medical condition is selected from wherein the medical condition is selected from the group consisting of: anorexia, nausea, emesis, pain, wasting syndrome, HIV-wasting, chemotherapy induced nausea and vomiting, alcohol use disorders, anti-tumor, amyotrophic lateral sclerosis, glioblastoma multiforme, glioma, increased intraocular pressure, glaucoma, cannabis use disorders, Tourette's syndrome, dystonia, multiple sclerosis, inflammatory bowel disorders, arthritis, dermatitis, Rheumatoid arthritis, systemic lupus erythematosus, anti-inflammatory, anti-convulsant, anti-psychotic, anti-oxidant, neuroprotective, anti-cancer, immunomodulatory effects, peripheral neuropathic pain, neuropathic pain associated with post-herpetic neuralgia. diabetic neuropathy, shingles, burns, actinic keratosis, oral cavity sores and ulcers, post-episiotomy pain, psoriasis, pruritis, contact dermatitis, eczema, bullous dermatitis herpetiformis, exfoliative dermatitis, mycosis fungoides, pemphigus, severe erythema multiforme (e.g., Stevens-Johnson syndrome), seborrheic dermatitis, ankylosing spondylitis, psoriatic arthritis, Reiter's syndrome, gout, chondrocalcinosis, joint pain secondary to dysmenorrhea, fibromyalgia, musculoskeletal pain,neuropathic-postoperative complications, polymyositis, acute nonspecific tenosynovitis, bursitis, epicondylitis, post-traumatic osteoarthritis, synovitis, and juvenile rheumatoid arthritis.

In one embodiment, the resulting $\Delta^9$-THC prodrug of Formula I is more hydrophilic than $\Delta^9$-THC and therefore more water soluble. The $\log_{10}$ values of the water/octanol partition coefficient (log P) for $\Delta^9$-THC and various prodrugs of $\Delta^9$-THC are shown in FIG. 10. A further embodiment is a prodrug of $\Delta^9$-THC having a log P value less than that of $\Delta^9$-THC. A further embodiment is a prodrug of $\Delta^9$-THC having a log P value greater than that of $\Delta^9$-THC. A further embodiment is a prodrug of $\Delta^9$-THC having a log P value which is approximately equal to that of $\Delta^9$-THC.

Pharmaceutical Excipients

The pharmaceutical compositions described herein can, if desired, include one or more pharmaceutically acceptable excipients. The term "excipient" herein means any substance, not itself a therapeutic agent, used as a carrier or vehicle for delivery of a therapeutic agent to a subject or added to a pharmaceutical composition, for example, to improve its handling or storage properties or to permit or facilitate formation of a dose unit of the composition. Excipients include, by way of illustration and not limitation, solvents, thickening agents, penetration enhancers, wetting agents, lubricants, emollients, substances added to mask or counteract a disagreeable odor, fragrances, and substances added to improve appearance or texture of the composition. Any such excipients can be used in any dosage forms of according to the present disclosure. The foregoing list of excipients is not meant to be exhaustive but merely illustrative as a person of ordinary skill in the art would recognize that additional excipients could be used to achieve the desired goals for delivery of the $\Delta^9$-THC prodrug.

Compositions of the disclosure containing excipients can be prepared by any technique known to a person of ordinary skill in the art of pharmacy, pharmaceutics, drug delivery, pharmacokinetics, medicine or other related discipline that comprises admixing an excipient with a drug or therapeutic agent.

In one embodiment, the $\Delta^9$-THC prodrugs described herein can be combined with a penetration enhancer. Non-limiting examples of penetration enhancing agents include C8-C22 fatty acids such as isostearic acid, octanoic acid, and oleic acid; C8-C22 fatty alcohols such as oleyl alcohol and lauryl alcohol; lower alkyl esters of C8-C22 fatty acids such as ethyl oleate, isopropyl myristate, butyl stearate, and methyl laurate; di(lower)alkyl esters of C6-C22 diacids such as diisopropyl adipate; monoglycerides of C8-C22 fatty acids such as glyceryl monolaurate; tetrahydrofurfuryl alcohol polyethylene glycol ether; polyethylene glycol, propylene glycol; 2-(2-ethoxyethoxy)ethanol; diethylene glycol monomethyl ether; alkylaryl ethers of polyethylene oxide; polyethylene oxide monomethyl ethers; polyethylene oxide dimethyl ethers; dimethyl sulfoxide; glycerol; ethyl acetate; acetoacetic ester; N-alkylpyrrolidone; and terpenes. Additional penetration enhancers suitable for use can also be found in U.S. patent application Ser. No. 10/032,163, published as US 2002-0111377 A1, on Aug. 15, 2002.

In one embodiment, the $\Delta^9$-THC prodrugs described herein can be combined with thickening agents (aka gelling agents). The thickening agent used herein may include anionic polymers such as polyacrylic acid (CARBOPOL® by Noveon, Inc., Cleveland, Ohio), carboxypolymethylene, carboxymethylcellulose and the like, including derivatives of Carbopol® polymers, such as Carbopol® Ultrez 10, Carbopol® 940, Carbopol® 941, Carbopol® 954, Carbopol® 980, Carbopol® 981, Carbopol® ETD 2001, Carbopol® EZ-2 and Carbopol® EZ-3, and other polymers such as Pemulen® polymeric emulsifiers, and Noveon® polycarbophils. Additional thickening agents, enhancers and adjuvants may generally be found in Remington's The Science and Practice of Pharmacy as well as the Handbook f Pharmaceutical Excipients, Arthur H. Kibbe ed. 2000. Thickening agents or gelling agents are present in an amount sufficient to provide the desired rheological properties of the composition. Illustratively, one or more pharmaceutically acceptable thickening agent or gelling agent are present in a total amount by weight of about 0.1%, about 0.25%, about 0.5%, about 0.75%, about 1%, about 1.25%, about 1.5%, about 1.75%, about 2.0%, about 2.25%, about 2.5%, about 2.75%, about 3.0%, about 3.25%, about 3.5%, about 3.75%, about 4.0%, about 4.25%, about 4.5%, about 4.75%, about 5.0%, about 5.25%, about 5.5%, about 5.75%, about 6.0%, about 6.25%, about 6.5%, about 6.75%, about 7.0%, about 7.25%, about 7.5%, about 7.75%, about 8.0%, about 8.25%, about 8.5%, about 8.75%, about 9.0%, about 9.25%, about 9.5%, about 9.75%, about 10%, about 10.5%, about 11%, about 11.5%, about 12%, about 12.5%, about 13%, about 13.5%, about 14%, about 14.5% or about 15%.

In one embodiment a neutralizing agent is optionally present to assist in forming a gel. Suitable neutralizing agents include sodium hydroxide (e.g., as an aqueous mixture), potassium hydroxide (e.g., as an aqueous mixture), ammonium hydroxide (e.g., as an aqueous mixture), triethanolamine, tromethamine (2-amino 2-hydroxymethyl-1,3 propanediol), aminomethyl propanol (AMP), tetrahydroxypropyl ethylene diamine, diisopropanolamine, Ethomeen C-25 (Armac Industrial Division), Di-2 (ethylhexyl) amine (BASF-Wyandotte Corp., Intermediate Chemicals Division), triamylamine, Jeffamine D-1000 (Jefferson Chemical Co.), b-Dimethylaminopropionitrite (American Cyanamid Co.), Armeen CD (Armac Industrial Division), Alamine 7D (Henkel Corporation), dodecylamine and morpholine. The neutralizing agent is present in an amount sufficient to form a gel which is suitable for contact with the skin of a mammal.

In one embodiment, the formulation is a gel, an ointment, a cream or a patch and comprises a $\Delta^9$-THC prodrug, optionally a penetration enhancing agent, a thickening agent, a lower alcohol, such as ethanol or isopropanol; and water. In another embodiment, the formulation is a gel, an ointment, a cream or a patch, further comprised of sodium hydroxide or triethanolamine or potassium hydroxide, or a combination thereof, in an amount sufficient, as is known in the art, to assist the gelling agent in forming a gel.

In one embodiment, a solution of sodium hydroxide is used, such as, e.g., 0.1 N sodium hydroxide solution, 0.2 N sodium hydroxide solution, 0.5 N sodium hydroxide solution, 1.0 N sodium hydroxide solution, 1.5 N sodium hydroxide solution, 2.0 N sodium hydroxide solution, or any other suitable solution for providing an amount sufficient of the sodium hydroxide to the composition. In one embodiment, the composition comprises about 1% to about 10% 0.1 N sodium hydroxide.

Additional embodiments include the following compositions:

Gel Formulation Used with Patches (18 mg/mL $\Delta^9$-THC or $\Delta^9$-THC Prodrug)

| | |
|---|---|
| 75.2% | propylene glycol, USP |
| 18.8% | sterile water for injection, USP |
| 6.0% | diethylene glycol monoethyl ether (Transcutol HP), EP/USP/NF |
| 5.0% | hydroxyethylcellulose (Natrosol ®), NF based on weight of other three components |

Gel Formulation Used for Rubbing into Skin

| | |
|---|---|
| 72.5-67.5% | absolute ethanol, USP/NF |
| 20.38-15.38% | sterile water for injection, USP |
| 4.72% | 0.1N NaOH (NF) in sterile water for injection, USP |
| 1-10% | $\Delta^9$-THC or $\Delta^9$-THC prodrug |
| 0.9% | Carbopol 980 ®, NF |
| 0.5% | isopropyl myristate, USP/NF |

Gel Formulation

| | |
|---|---|
| 78.1% | absolute ethanol, USP/NF |
| 15.3% | sterile water for injection, USP |
| 1.5% | triethanolamine, NF |
| 3.5% | $\Delta^9$-THC or $\Delta^9$-THC prodrug |
| 1.0% | Carbopol 980 ®, NF |
| 0.6% | isopropyl myristate, USP/NF |

Gel Formulation

| | |
|---|---|
| 91.75-82.75% | absolute ethanol, USP/NF |
| 5.0% | propylene glycol, USP |
| 1-10% | $\Delta^9$-THC or $\Delta^9$-THC prodrug |
| 1.25% | polyoxyethylene (15) cocoalkylamines (Ethomeen ® C/25) |
| 0.5% | Carbopol 980 ®, NF |
| 0.5% | isopropyl myristate, USP/NF |

Compositions described herein optionally comprise one or more pharmaceutically acceptable wetting agents as excipients. Non-limiting examples of surfactants that can be used as wetting agents in compositions of the disclosure include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and octoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefossé), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefossé), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, constitute in total about 0.25% to about 15%, about 0.4% to about 10%, or about 0.5% to about 5%, of the total weight of the composition. Illustratively, one or more pharmaceutically acceptable wetting agents are present in a total amount by weight of about 0.25%, about 0.5%, about 0.75%, about 1%, about 1.25%, about 1.5%, about 1.75%, about 2.0%, about 2.25%, about 2.5%, about 2.75%, about 3.0%, about 3.25%, about 3.5%, about 3.75%, about 4.0%, about 4.25%, about 4.5%, about 4.75%, about 5.0%, about 5.25%, about 5.5%, about 5.75%, about 6.0%, about 6.25%, about 6.5%, about 6.75%, about 7.0%, about 7.25%, about 7.5%, about 7.75%, about 8.0%, about 8.25%, about 8.5%, about 8.75%, about 9.0%, about 9.25%, about 9.5%, about 9.75% or about 10%.

Compositions described herein optionally comprise one or more pharmaceutically acceptable lubricants (including anti-adherents and/or glidants) as excipients. Suitable lubricants include, either individually or in combination, glyceryl behapate (e.g., Compritol™ 888); stearic acid and salts thereof, including magnesium (magnesium stearate), calcium and sodium stearates; hydrogenated vegetable oils (e.g., Sterotex™); colloidal silica; talc; waxes; boric acid; sodium benzoate; sodium acetate; sodium fumarate; sodium chloride; DL-leucine; PEG (e.g., Carbowax™ 4000 and Carbowax™ 6000); sodium oleate; sodium lauryl sulfate; and magnesium lauryl sulfate. Such lubricants, if present, constitute in total about 0.1% to about 10%, about 0.2% to about 8%, or about 0.25% to about 5%, of the total weight of the composition. Illustratively, one or more pharmaceutically acceptable lubricants are present in a total amount by weight of about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, about 5.2%, about 5.3%, about 5.4%, about 5.5%, about 5.6%, about 5.7%, about 5.8%, about 5.9%, about 6.0%, about 6.1%, about 6.2%, about 6.3%, about 6.4%, about 6.5%, about 6.6%, about 6.7%, about 6.8%, about 6.9%, about 7.0%, about 7.1%, about 7.2%, about 7.3%, about 7.4%, about 7.5%, about 7.6%, about 7.7%, about 7.8%, about 7.9%, about 8.0%, about 8.1%, about 8.2%, about 8.3%, about 8.4%, about 8.5%, about 8.6%, about 8.7%, about 8.8%, about 8.9%, about 9.0%, about 9.1%, about 9.2%, about 9.3%, about 9.4%, about 9.5%, about 9.6%, about 9.7%, about 9.8%, about 9.9% or about 10.0%.

In another embodiment, the compositions described herein optionally comprise an emollient. Illustrative emollients include mineral oil, mixtures of mineral oil and lanolin alcohols, cetyl alcohol, cetostearyl alcohol, petrolatum, petrolatum and lanolin alcohols, cetyl esters wax, cholesterol, glycerin, glyceryl monostearate, isopropyl myristate, isopropyl palmitate, lecithin, allyl caproate, althea officinalis extract, arachidyl alcohol, argobase EUC, butylene glycol dicaprylate/dicaprate, acacia, allantoin, carrageenan, cetyl dimethicone, cyclomethicone, diethyl succinate, dihydroabietyl behenate, dioctyl adipate, ethyl laurate, ethyl palmitate, ethyl stearate, isoamyl laurate, octanoate, PEG-75 lanolin, sorbitan laurate, walnut oil, wheat germ oil super refined almond, super refined sesame, super refined soybean, octyl palmitate, caprylic/capric triglyceride and glyceryl cocoate. An emollient, if present, is present in the compositions described herein in an amount of about 1% to about 30%, about 3% to about 25%, or about 5% to about 15%, by weight. Illustratively, one or more emollients are present in a total amount of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%, by weight.

In one embodiment, a composition comprises an antimicrobial preservative. Illustrative anti-microbial preservatives include acids, including but not limited to benzoic acid, phenolic acid, sorbic acids, alcohols, benzethonium chloride, bronopol, butylparaben, cetrimide, chlorhexidine, chlorobutanol, chlorocresol, cresol, ethylparaben, imidurea, methylparaben, phenol, phenoxyethanol, phenylethyl alcohol, phenylmercuric acetate, phenylmercuric borate, phenylmercuric nitrate, potassium sorbate, propylparaben, sodium propionate, or thimerosal. The anti-microbial preservative, if present, is present in an amount of about 0.1% to about 5%, about 0.2% to about 3%, or about 0.3% to about 2%, by weight, for example about 0.2%, 0.4%, 0.6%, 0.8%, 1%, 1.2%, 1.4%, 1.6%, 1.8%, 2%, 2.2%, 2.4%, 2.6%. 2.8%, 3.0%, 3.2%, 3.4%, 3.6%, 3.8%, 4%, 4.2%, 4.4%, 4.6%, 4.8%, or 5%.

Compositions described herein optionally compromise one or more emulsifying agents. The term "emulsifying agent" refers to an agent capable of lowering surface tension between a non-polar and polar phase and includes compounds defined elsewhere as "self emulsifying" agents. Suitable emulsifying agents can come from any class of pharmaceutically acceptable emulsifying agents including carbohydrates, proteins, high molecular weight alcohols, wetting agents, waxes and finely divided solids. The optional emulsifying agent, if present, is present in a composition in a total amount of about 1% to about 15%, about 1% to about 12%, about 1% to about 10%, or about 1% to about 5% by weight of the composition. Illustratively, one or more emulsifying agents are present in a total amount by weight of about 1%, about 2%, about 3%, about 4%, about 5%, about 6%, about 7%, about 8%, about 9%, about 10%, about 11%, about 12%, about 13%, about 14%, or about 15%.

In another embodiment, the water immiscible solvent comprises propylene glycol, and is present in a composition in an amount of about 1% to about 99%, by weight of the composition, for example about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 99%.

Compositions described herein may optionally comprise one or more binding agents. Binding agents may be either dry or wet. Dry binding agents may include simple and complex carbohydrates (e.g., sucrose, glucose, fructose, maltose, lactose, maltodextrins, starch, modified starches, mannitol, sorbitol, maltitol, xylitol, and erthritol), cellulose, and cellulosic derivatives (e.g., microcrystalline cellulose, carboxymethyl cellulose, and hydroxyethyl cellulose). Wet binder agents may include polyvinyl pyrrolidone, methylcellulose, hydroxypropyl cellulose, hydroxypropyl methylcellulose, carboxymethylcellulose, xanthan gum, carrageenan gum, locust bean gum, alginates, and acacia. Depending on the desired result, a person of ordinary skill in the art of pharmacy, pharmaceutics, drug delivery, pharmacokinetics, medicine or other related discipline that comprises admixing an excipient with a drug or therapeutic agent to a composition would be able to select the appropriate binding agent and the relative concentration of the binding agent.

In another embodiment, the compositions described herein may contain disintegrants, such as sodium starch glycolate, crosspovidone, crosscarmellose, microcrystalline cellulose and starch. Depending on the desired result, a person of ordinary skill in the art of pharmacy, pharmaceutics, drug delivery, pharmacokinetics, medicine or other related discipline that comprises admixing an excipient with a drug or therapeutic agent to a composition would be able to select the appropriate disintegrant and the relative concentration of the disintegrant.

In a further embodiment, the compositions disclosed herein may contain lubricants, such as magnesium stearate, stearic acid and its pharmaceutically acceptable salts, talc, vegetable oils, and waxes. Depending on the desired result, a person of ordinary skill in the art of pharmacy, pharmaceutics, drug delivery, pharmacokinetics, medicine or other related discipline that comprises admixing an excipient with a drug or therapeutic agent to a composition would be able to select the appropriate lubricant and the relative concentration of the lubricant.

Compositions described herein may also optionally comprise one or more taste enhancers, such as sweeteners, including aspartame, acesulfame potassium, sucralose and saccharin or taste masking agents, such as flavorings. Depending on the desired result, a person of ordinary skill in the art of pharmacy, pharmaceutics, drug delivery, pharmacokinetics, medicine or other related discipline that comprises admixing an excipient with a drug or therapeutic agent to a composition would be able to select the appropriate taste enhancer or taste making agent and the relative concentration of the taste enhancer or taste masking agent.

Therapeutic Uses

In one embodiment, compositions disclosed herein comprise one or more $\Delta^9$-THC prodrugs in a total amount of between about 0.1% and about 95% by weight of the composition, for example about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90% or about 95%.

The term "therapeutically effective amount" or "therapeutically and/or prophylactically effective amount" as used herein refers to an amount of compound or agent that is sufficient to elicit the required or desired therapeutic and/or prophylactic response, as the particular treatment context may require.

It will be understood that a therapeutically and/or prophylactically effective amount of a drug for a subject is dependent inter alia on the body weight of the subject as well as other factors known to a person of ordinary skill in the art. A "subject" herein to which a therapeutic agent or composition thereof can be administered includes mammals such as a human subject of either sex and of any age, and also includes any nonhuman animal, particularly a domestic or companion animal, illustratively a cat, dog or a horse as well as laboratory animals such as guinea pigs.

The terms "treat", "treated", "treating" and "treatment" are to be broadly understood as referring to any response to, or anticipation of, a medical condition in a mammal, particularly a human, and includes but is not limited to:

(i) preventing the medical condition from occurring in a subject, which may or may not be predisposed to the condition, but has not yet been diagnosed with the condition and, accordingly, the treatment constitutes prophylactic treatment for the medical condition;

(ii) inhibiting the medical condition, i.e., arresting, slowing or delaying the onset, development or progression of the medical condition; or (iii) relieving the medical condition, i.e., causing regression of the medical condition.

In one embodiment, a therapeutically effective amount of a $\Delta^9$-THC prodrug is administered to treat a medical condition selected from the group consisting of: anorexia, nausea, emesis, pain, wasting syndrome, HIV-wasting, chemotherapy induced nausea and vomiting, alcohol use disorders, anti-tumor, amyotrophic lateral sclerosis, glioblastoma multiforme, glioma, increased intraocular pressure, glaucoma, cannabis use disorders, Tourette's syndrome, dystonia, multiple sclerosis, inflammatory bowel disorders, arthritis, dermatitis, Rheumatoid arthritis, systemic lupus erythematosus, anti-inflammatory, anti-convulsant, anti-psychotic, anti-oxidant, neuroprotective, anti-cancer, immunomodulatory effects, peripheral neuropathic pain, neuropathic pain associated with post-herpetic neuralgia, diabetic neuropathy, shingles, burns, actinic keratosis, oral cavity sores and ulcers, post-episiotomy pain, psoriasis, pruritis, contact dermatitis, eczema, bullous dermatitis herpetiformis, exfoliative dermatitis, mycosis fungoides, pemphigus, severe erythema multiforme (e.g., Stevens-Johnson syndrome), seborrheic dermatitis, ankylosing spondylitis, psoriatic arthritis, Reiter's syndrome, gout, chondrocalcinosis, joint pain secondary to dysmenorrhea, fibromyalgia, musculoskeletal pain, neuropathic-postoperative complications, polymyositis, acute nonspecific tenosynovitis, bursitis, epicondylitis, post-traumatic osteoarthritis, synovitis, and juvenile rheumatoid arthritis.

Pharmaceutical Dosage Forms

In one embodiment, a single dosage unit of any formulation comprises a therapeutically effective amount or a therapeutically and/or prophylactically effective amount of a $\Delta^9$-THC prodrug.

In one embodiment, compositions described herein are suitable for transdermal administration. In another embodiment, transdermally administrable compositions are adapted for administration in and/or around the abdomen, back, chest, legs, arms, scalp or other suitable skin surface and may include formulations in which the $\Delta^9$-THC prodrug is administered in patches, ointments, creams, suspensions, lotions, pastes, gels, sprays, foams or oils.

In another embodiment, compositions described herein which are transdermally administrable include formulations in which the $\Delta^9$-THC prodrug is placed in a glycol or gel formulation.

In one embodiment, compositions described herein are suitable for topical administration. In another embodiment, topical administrable compositions are adapted for administration in and/or around the abdomen, back, chest, legs, arms, scalp or other suitable skin surface and may include formulations in which the Δ⁹-THC prodrug is administered in patches, ointments, creams, suspensions, lotions, pastes, gels, sprays, foams or oils.

In another embodiment, the compositions described herein are suitable for oral administration. In another embodiment, compositions described herein that are orally administrable include formulations in which the Δ⁹-THC prodrug is administered in tablets, capsules, suspensions, syrups or liquids. In an additional embodiment, the composition maybe formulated as extended release or long acting tablet or capsule. In a further embodiment, the oral dosage form may be enteric coated using compositions and techniques known to a person of ordinary skill in the art.

In one embodiment, compositions described herein are suitable for buccal administration. In another embodiment, compositions described herein that are bucally administrable may include formulations in which the Δ⁹-THC prodrug is administered in lozenges, sprays, gels, pastes, dissolvable tablets or dissolvable strips.

In one embodiment, compositions described herein are suitable for sublingual administration. In another embodiment, compositions described herein that are sublingually administrable may include formulations in which the Δ⁹-THC prodrug is administered in lozenges, sprays, gels, pastes, dissolvable tablets or dissolvable strips.

In one embodiment, compositions described herein are suitable for injectable administration. In another embodiment, compositions described herein that are injectably administrable may include formulations in which the Δ⁹-THC prodrug is administered as an intravenous, intrathecal, subcutaneous or depot injection.

In one embodiment, compositions described herein are suitable for rectal administration. In another embodiment, compositions described herein that are rectally administrable may include formulations in which the Δ⁹-THC prodrug is placed in suppositories, ointments, creams, suspensions, solutions, lotions, pastes, gels, sprays, foams or oils.

In one embodiment, compositions described herein are suitable for vaginal administration. In another embodiment, compositions described herein that are vaginally administrable may include formulations in which the Δ⁹-THC prodrug is placed in suppositories, ointments, creams, suspensions, solutions, lotions, pastes, gels, sprays, foams or oils.

In one embodiment, compositions described herein are suitable for ocular administration. In another embodiment, compositions described herein that are ocularly administrable may include formulations in which the Δ⁹-THC prodrug is placed in ointments, suspensions, solutions, gels or sprays.

In one embodiment, compositions described herein are suitable for nasal administration. In another embodiment, compositions described herein that are nasally administrable may include formulations in which the Δ⁹-THC prodrug is placed in ointments, suspensions, solutions, lotions, pastes, gels, sprays or mists.

EXAMPLES

Example 1

Section I. Summary

The objective was to synthesize Δ⁹-tetrahydrocannabinol prodrugs and assess the permeation of Δ⁹-tetrahydrocannabinol and its prodrugs through human abdominal skin in vitro. Nine Δ⁹-tetrahydrocannabinol prodrugs were synthesized and tested. Synthesized prodrugs of Δ⁹-tetrahydrocannabinol were analyzed for chemical stability in a formulation comparable to donor solution for diffusion testing to screen potential candidates' chemical stability and to decide the capability of the prodrug to withstand the formulation during the course of a diffusion study. Synthesized prodrugs of Δ⁹-tetrahydrocannabinol were analyzed for plasma stability to monitor the rate of conversion to Δ⁹-tetrahydrocannabinol. Potential candidates would convert readily to Δ⁹-tetrahydrocannabinol in plasma whereas stable prodrugs would convert very little. The procedure was performed to screen out compounds with no bioconversion to the parent molecule. Flow through diffusion cells were used for the permeation studies. The receiver used for the permeation studies was either 25% aqueous ethanol or 40% aqueous PEG (polyethylene glycol) 400. Donor solution was comprised of 100% PG (propylene glycol), 1:1:1 PG:ethanol:H₂O, 2.36:1.18:1 PG:ethanol:H₂O, or a rubbed in gel formulation. The flux and lag time values of Δ⁹-tetrahydrocannabinol and Δ⁹-tetrahydrocannabinol prodrugs were obtained from the permeation profiles. Drug accumulation in the skin after a 24 h diffusion experiment was determined as μmol/g wet tissue weight.

Section II. Methodology 1.0 Purpose: Synthesize Δ⁹-tetrahydrocannabinol prodrugs and assess the human skin permeation of Δ⁹-tetrahydrocannabinol and Δ⁹-tetrahydrocannabinol prodrugs in vitro. The following compounds were synthesized and assessed:

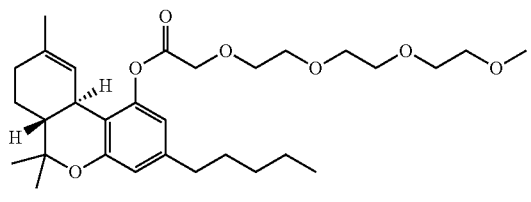

ALL00117
MW: 518.68
Formula: $C_{30}H_{46}O_7$

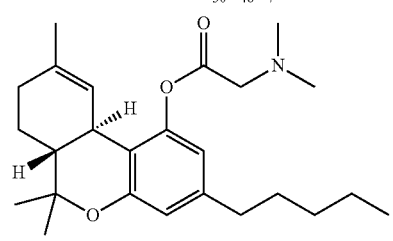

ALL00118
MW: 399.57
Formula: $C_{25}H_{37}NO_3$

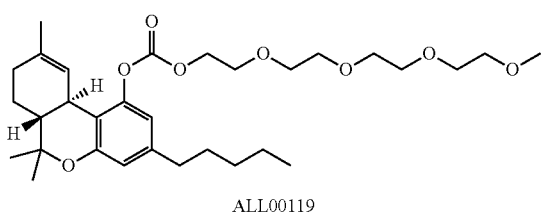

ALL00119
MW: 548.71
Formula: $C_{31}H_{48}O_8$

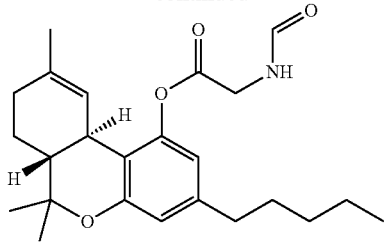

ALL00120
MW: 399.50
Formula: $C_{24}H_{33}NO_4$

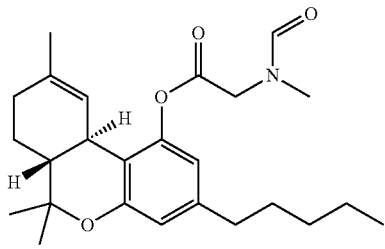

ALL00121
MW: 413.55
Formula: $C_{25}H_{35}NO_4$

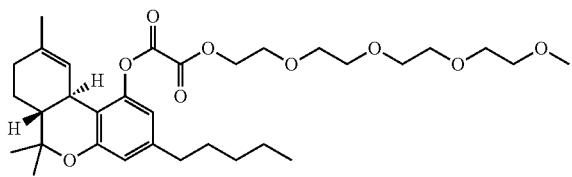

ALL00122
MW: 576.72
Formula: $C_{32}H_{48}O_9$

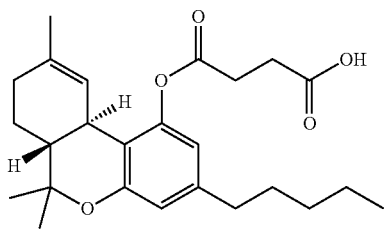

ALL00123
MW: 414.53
Formula: $C_{25}H_{34}O_5$

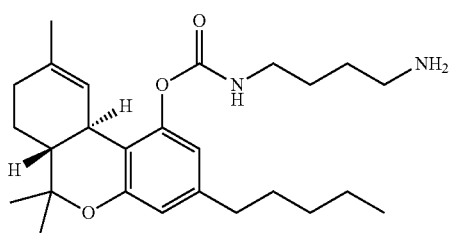

ALL00124
MW: 428.61
Formula: $C_{26}H_{40}N_2O_3$

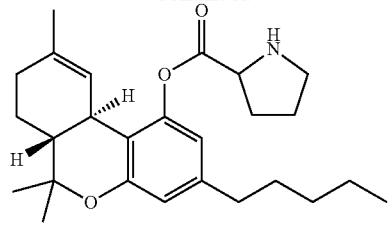

ALL00125
MW: 411.58
Formula: $C_{26}H_{37}NO_3$ 2.0 Skin Details

The skin samples used in the following experiments were obtained from abdominal reduction surgery and dermatomed to a thickness of approximately 200 μm. The skin samples used herein were frozen at −20° C. for less than six months.

3.0 Chemicals

Acetonitrile (HPLC grade), trifluoroacetic acid, triethylamine, gentamicin sulfate, isopropyl myristate (IPM), acetone, 4-dimethylaminopyridine, tetraethyleneglycol monomethyl ether, 1-octanethiol, and sodium hydroxide were purchased through Fisher Scientific (Fairlawn, N.J.). Methanol (HPLC grade), acetonitrile (HPLC grade), N,N'-dicyclohexylcarbodiimide, N,N-dimethylglycine, 1,8-diazabicyclo[5.4.0]undec-7-ene (DBU), mono-Fmoc-1,4-butanediamine hydrochloride, and polyethylene glycol 400 (PEG 400) were purchased through VWR (West Chester, Pa.). Propylene glycol (PG), triethylene glycol, triphosgene, $\Delta^9$-tetrahydrocannabinol, and absolute ethanol, thiphenol, succinic anhydride, N-formylglycine, N-(2-nitrophenylsulfenyl)-L-proline dicyclohexylammonium salt were purchased from Sigma-Aldrich (St. Louis, Mo.). Petroleum ether, ethyl acetate, hexane, chloroform, anhydrous sodium sulfate, methylene chloride, and dichloromethane were obtained from the University of Kentucky Chemical Stores (Lexington, Ky.). Argon and pre-purified nitrogen were purchased from Scott Gross Company (Lexington, Ky.). Carbopol® 980 was obtained from Noveon, Inc. (Cleveland, Ohio). Nanopure water was obtained from a Barnstead NANOpure® Diamond™ Ultrapure water filtration system (Dubuque, Iowa). The following compounds were synthesized according to literature procedures: 3,6,9,12-tetraoxatridecanoic acid (*Macromolecules*, 39 (12), 3978-3979, 2006.) and N-formylsarcosine (U.S. Pat. No. 5,684,161 (1997).

4.0 Synthesis of $\Delta^9$-Tetrahydrocannabinol ($\Delta^9$-THC) prodrugs 4.1 Synthesis of ALL00117 ($\Delta^9$-Tetrahydrocannabinol 3,6,9,12-tetraoxatridecanoyl ester)

THC (68.6 mg, 0.218 mmol) was dissolved in 5 mL of dichloromethane. Next, 3,6,9,12-tetraoxatridecanoic acid (63.0 mg, 0.283 mmol) in dichloromethane (1 mL) was added followed by 4-dimethylaminopyridine (4.5 mg, 0.0218 mmol) and N,N'-dicyclohexylcarbodiimide (76.5 mg, 0.371 mmol). The mixture was stirred at ambient temperature for 2 h. The mixture was diluted with hexane (6 mL), filtered, concentrated under a reduced pressure and chromatographed on silica gel with hexane-ethyl acetate (gradient 4:1, 2:1, 1:1, 0:1). Fractions containing the product were concentrated under a reduced pressure, dissolved in hexane with a few drops of ethyl acetate, filtered and concentrated again to afford ALL00117 (83 mg, 73%) as an oil.

For ALL00117, the $^1$H NMR (400 MHz, CDCl$_3$) was as follows: δ=6.57 (1H, d, J=1.8, H-4); 6.42(1H, d, J=1.8, H-2); 5.86-6.90 (1H, m, H-10); 4.42(2H, s, OCH$_2$CO$_2$); 3.88-3.76 (2H, m, PEG); 3.75-3.64(8H, m, PEG); 3.58-3.54(2H, m, PEG); 3.39(s, 3H, CH$_2$OCH$_3$); 3.11-3.03(1H, m, H-10a); 2.49(2H, t, J=8.3, ArCH$_2$); 2.09-2.17(2H, m); 1.85-1.94 (1H, m); 1.62-1.70(4H, m); 1.52-1.62(2H, m); 1.41(3H, s, 6β-Me); 1.24-1.41(5H, m); 1.09(3H, s, 6α-Me); 0.88 (3H, t, J=7.0, CH$_2$CH$_3$).

4.2 Synthesis of ALL00118 (Δ$^9$-Tetrahydrocannabinol N,N-dimethylglycyl ester)

The same procedure as for ALL00117 starting from N,N-dimethylglycine (60.3 mg, 0.585 mmol), THC (141 mg, 0.45 mmol), N,N'-dicyclohexylcarbodiimide (158 mg, 0.765 mmol), 4-dimethylaminopyridine (9.3 mg, 0.045 mmol) in dichloromethane (4.5 mL) afforded 143 mg (80%) of ALL00118 as an oil.

For ALL00118, the $^1$H NMR (400 MHz, CDCl$_3$) was as follows: δ=6.55(1H, d, J=1.8, H-4); 6.41(1H, d, J=1.8, H-2); 5.89-5.92 (1H, m, H-10); 3.43(2H, s, COCH$_2$); 3.04-3.12 (1H, m, H-10a); 2.49(2H, t, J=7.8, ArCH$_2$); 2.44(6H, s, N(CH$_3$)$_2$); 2.09-2.16(2H, m); 1.85-1.93 (1H, m); 1.62-1.70 (4H, m); 1.52-1.61(2H, m); 1.40(3H, s, 6β-Me); 1.23-1.40 (5H, m); 1.08(3H, s, 6α-Me); 0.88 (3H, t, J=7.0, CH$_2$CH$_3$).

4.3 Synthesis of ALL00119 (Δ$^9$-Tetrahydrocannabinol 3,6,9,12-tetraoxatridecyl carbonate)

Tetraethyleneglycol monomethyl ether (208 mg, 0.00065 mol) was dissolved in dichloromethane and the solution chilled in an ice bath. Triphosgene (56 mg, 0.00019 mol) was dissolved in dichloromethane and this solution slowly added to the tetraethyleneglycol monomethyl ether solution with stirring while maintained at 0° C. The mixture was kept under argon and stirred for three hours.

Tetrahydrocannabinol (170 mg, 0.00054 mol) was dissolved in 10 mL of dichloromethane. Triethylamine (82 mg, 0.00081 mol) was added drop-by-drop. The solution was covered with argon, sealed and stirred for three hours.

The two solutions were combined and allowed to come to ambient temperature. The mixture was kept under argon and allowed to stir overnight. The solvent was reduced to a small volume under nitrogen and hexane was added. The precipitate that formed was removed by filtration. The filtrate was taken to dryness under vacuum. The crude product was reconstituted in 1:1 hexane:methylene chloride.

A silica column was used to purify the crude material using 1:1 hexane: ethyl acetate as an eluent to afford 112 mg (38%) of ALL00119. The purified product appeared as a transparent, viscous oil with light amber color.

For ALL00119, the $^1$H NMR (400 MHz, CDCl$_3$) was as follows: δ=6.56(1H, d, J=1.8, H-4); 6.50(1H, d, J=1.8, H-2); 5.98-6.02 (1H, m, H-10); 4.36-4.42(2H, m, COOCH$_2$); 3.79(2H, t, J=4.7, CH$_2$OCH$_3$); 3.63-3.71(10H, m); 3.54-3.57 (2H, m); 3.38(3H, s, CH$_2$OCH$_3$); 3.13-3.21 (1H, m, H-10a); 2.49(2H, t, J=7.8, ArCH$_2$); 2.10-2.17(2H, m); 1.86-1.94 (1H, m); 1.63-1.71(4H, m); 1.52-1.62(2H, m); 1.41(3H, s, 6β-Me); 1.23-1.41(5H, m); 1.09(3H, s, 6α-Me); 0.88 (3H, t, J=7.0, CH$_2$CH$_3$).

4.4 Synthesis of ALL00120 (Δ$^9$-Tetrahydrocannabinol N-formylglycyl ester)

Tetrahydrocannabinol (134 mg, 0.00043 mol), N-formylglycine (56 mg, 0.00054 mol), DMAP (5.3 mg, 0.00004 mol) were combined in 10 mL dichloromethane. The solution was stirred for 20 minutes at ambient temperature. DCC (124 mg, 0.00060 mol) was added to the mixture. The mixture was allowed to stir overnight at ambient temperature.

The solution was reduced to a small volume under nitrogen and hexane was added. The precipitate that formed was removed by filtration. The filtrate was taken to dryness under vacuum. The crude product was reconstituted in 1:1 hexane: methylene chloride.

A silica column was used to purify the crude material using 1:1 hexane: ethyl acetate as an eluent. The purified product appeared as a transparent, viscous oil with light amber color (136.8 mg, 80%).

For ALL00120, the $^1$H NMR (400 MHz, CDCl$_3$) was as follows: δ=8.29-8.31 (1H, m, CHO); 6.58(1H, d, J=1.8, H-4); 6.43(1H, d, J=1.8, H-2); 6.15 (1H, s br, NH); 5.85-5.88 (1H, m, H-10); 4.37(2H, AB system split by two additional coupling constants J=0.7 and J=5.1, OCOCH$_2$N); 2.99-3.06 (1H, m, H-10a); 2.50(2H, t, J=7.8, ArCH$_2$); 2.11-2.18(2H, m); 1.86-1.94 (1H, m); 1.62-1.70(4H, m); 1.52-1.62(2H, m); 1.41(3H, s, 6β-Me); 1.23-1.40(5H, m); 1.08(3H, s, 6α-Me); 0.88 (3H, t, J=7.0, CH$_2$CH$_3$).

4.5 Synthesis of ALL00121 (Δ$^9$-Tetrahydrocannabinol N-formylsarcosyl ester)

The same procedure as for ALL00117 (reaction time 3 h), starting from N-formylsarcosine (73.2 mg, 0.625 mmol), THC (157 mg, 0.5 mmol), N,N'-dicyclohexylcarbodiimide (144.4 mg, 0.70 mmol) and 4-dimethylaminopyridine (10.3 mg, 0.05 mmol) in dichloromethane (7.5 mL) afforded 161 mg (78%) of ALL00121 as an oil.

For ALL00121, the $^1$H NMR (400 MHz, CDCl$_3$) was as follows: (the spectrum shows a mixture (~2:1) of two rotamers), δ=(major rotamer) 8.16 (1H, s, CHO); 6.56(1H, d, J=1.6, H-4); 6.44(1H, d, J=1.8, H-2); 5.87-5.91 (1H, m, H-10); 4.36(2H, AB system, OCOCH$_2$N); 3.11(3H, s, NCH$_3$); 2.99-3.10 (1H, m, H-10a); 2.49(2H, t, J=7.8, ArCH$_2$); 2.11-2.18(2H, m); 1.86-1.95 (1H, m); 1.62-1.71 (4H, m); 1.52-1.62(2H, m); 1.41(3H, s, 6β-Me); 1.23-1.40 (5H, m); 1.08(3H, s, 6α-Me); 0.88 (3H, t, J=7.0, CH$_2$CH$_3$).

4.6 Synthesis of ALL00122 (Δ$^9$-Tetrahydrocannabinol 3,6,9,12-tetraoxatridecyl oxalate)

Tetraethyleneglycol monomethyl ether (402 mg, 1.93 mmol) was added dropwise to oxalyl chloride (1.63 mL, 19.3 mmol) with stirring and cooling with ice-water. The mixture was allowed to warm to ambient temperature, stirred for 20 min and concentrated under a reduced pressure. Benzene (0.3 mL) was added and the mixture was concentrated again to afford 571 mg of a crude oxalic acid mono-3,6,9,12-tetraoxatridecyl ester chloride.

The crude oxalic acid mono-3,6,9,12-tetraoxatridecyl ester chloride (269 mg, 0.90 mmol) was added dropwise to a solution of THC (188.6 mg, 0.60 mmol) and 4-dimethylaminopyridine (223 mg, 1.08 mmol) in dry dichloromethane (3 mL) under an argon atmosphere with stirring and cooling with ice-water. The mixture was stirred at ambient temperature for 2 h and additional two portions of both 4-dimethylaminopyridine (44 mg) and the crude oxalic acid monoester chloride (54 mg) every 2 h with cooling. The mixture was stirred overnight, diluted with hexane, filtered and concentrated under a reduced pressure. The residue was chromatographed on silica gel with hexane—ethyl acetate (gradient 2:1, 1:1, 0:1) to afford 189 mg (39%) of ALL00122 as an oil.

For ALL00122, the $^1$H NMR (400 MHz, CDCl$_3$) was as follows: δ=6.60(1H, d, J=1.6, H-4); 6.49(1H, d, J=1.8, H-2); 5.99-6.03 (1H, m, H-10); 4.46-4.57(2H, m, COOCH$_2$); 3.84(2H, t, J=4.9, CH$_2$OCH$_3$); 3.62-3.72(10H, m); 3.52-3.56 (2H, m); 3.37(3H, s, CH$_2$OCH$_3$); 3.04-3.12 (1H, m, H-10a); 2.50(2H, t, J=7.8, ArCH$_2$); 2.09-2.16(2H, m); 1.85-1.93 (1H, m); 1.63-1.71(4H, m); 1.52-1.61(2H, m); 1.41(3H, s, 6β-Me); 1.23-1.41(5H, m); 1.09(3H, s, 6α-Me); 0.88 (3H, t, J=6.9, CH$_2$CH$_3$).

4.7 Synthesis of ALL00123 ($\Delta^9$-Tetrahydrocannabinol hemisuccinate)

A mixture of THC (204.4 mg, 0.65 mmol), succinic anhydride (91.1 mg, 0.91 mmol) and 4-dimethylaminopyridine (187.8 mg, 0.91 mmol) in dichloromethane (3.25 mL) was stirred at ambient temperature for 4 h. An additional amount of succinic anhydride (43 mg) and 4-dimethylaminopyridine (102 mg) was added and the stirring was continued overnight. Glacial acetic acid (351 mg, 5.85 mmol) was added with stirring and the reaction mixture was directly chromatographed on silica gel with hexane—ethyl acetate (gradient 2:1, 1:1, 0:1) to afford 133.8 mg (50%) of ALL00123 as an oil.

For ALL00123, the $^1$H NMR (400 MHz, CDCl$_3$) was as follows: δ=6.55(1H, d, J=1.8, H-4); 6.41(1H, d, J=1.8, H-2); 5.92-6.95 (1H, m, H-10); 3.01-3.08 (1H, m, H-10a); 2.84-2.97 (2H, m, CH$_2$CH$_2$CO2H); 2.77-2.83(2H, m, CH$_2$CH$_2$CO2H); 2.49(2H, t, J=7.8, ArCH$_2$); 2.10-2.17(2H, m); 1.85-1.93 (1H, m); 1.62-1.70(4H, m); 1.52-1.61(2H, m); 1.40(3H, s, 6β-Me); 1.25-1.40(5H, m); 1.08(3H, s, 6α-Me); 0.88 (3H, t, J=7.0, CH$_2$CH$_3$).

4.8 Synthesis of ALL00124 ($\Delta^9$-Tetrahydrocannabinol 4-aminobutyl carbamate)

To a stirred solution of mono-Fmoc-1,4-butanediamine hydrochloride (461 mg, 1.33 mmol) in saturated NaHCO$_3$ aqueous solution (33.3 mL) and dichloromethane (22.2 mL) was added triphosgene (592 mg, 2.0 mmol) in dichloromethane (5 mL) at ambient temperature. After stirring for 1 hr, the product was extracted with dichloromethane (40 mL), and the dichloromethane layer was dried over anhydrous Na$_2$SO$_4$, and concentrated. The residue was dissolved in ethyl acetate and the product was precipitated with addition of hexane. Fmoc-4-aminobutyl isocyanate was collected by filtration as a white solid (305 mg, 68%).

Triethylamine was added to a solution of THC (141.5 mg, 0.45 mmol) in dry DCM (0.4 mL). After stirring for 5 min at ambient temperature under an argon atmosphere, Fmoc-4-aminobutyl isocyanate solution in dry DCM (0.4 mL) was added and the stirring was continued overnight. The reaction mixture was filtered and the filtrate was chromatographed on silica gel with hexane—ethyl acetate (gradient 10:1, 5:1, 4:1, 2:1) to afford 216 mg (74%) of THC Fmoc-4-aminobutyl carbamate.

To a stirred solution of THC Fmoc-4-aminobutyl carbamate (202 mg, 0.31 mmol) in THF (3 mL) was added 1-octanethiol (227 mg, 1.55 mml), followed by DBU (6.28 mg, 0.062 mmol). After stirring at ambient temperature for 105 min the reaction mixture was diluted with hexane (3 mL) and directly chromatographed on silica gel with dichloromethane—methanol (gradient 1:0, 20:1, 10:1, 5:1, 3:1, 2:1,1:1) to afford 120 mg (90%) of ALL00124 as an oil. The compound should be stored at −20° C. immediately after concentration in order to avoid the decomposition to THC.

For ALL00124, the $^1$H NMR (400 MHz, CDCl$_3$) was as follows: δ=6.52(1H, d, J=1.6, H-4); 6.47(1H, d, J=1.6, H-2); 5.96-6.01 (1H, m, H-10); 5.44(1H, br t, J=5.6, OCONH); 3.24-3.34(2H, m); 3.15-3.24(2H, m); 3.09-3.15 (1H, m, H-10a); 2.75(2H, t, J=6.6); 2.48(2H, t, J=7.8, ArCH$_2$); 2.20-2.32(1H, m); 2.09-2.18(2H, m); 1.48-1.94(21H, m); 1.42(3H, s, 6β-Me); 1.23-1.42 (5H, m); 1.09(3H, s, 6α-Me); 0.87 (3H, t, J=7.0, CH$_2$CH$_3$).

4.9 Synthesis of ALL00125 ($\Delta^9$-Tetrahydrocannabinol prolylester)

N-(2-Nitrophenylsulfenyl)-L-proline was set free from its dicyclohexylammonium salt (150 mg) by extraction from pH 3.5 citrate buffer with dichloromethane.

The same procedure as for ALL00117 (reaction time 1 h), starting from N-(2-Nitrophenylsulfenyl)-L-proline, THC (76.8 mg, 0.244 mmol), N,N'-dicyclohexylcarbodiimide (70.4 mg, 0.34 mmol), 4-dimethylaminopyridine (3 mg, 0.024 mmol) in dichloromethane afforded 102.7 mg (74.5%) of THC N-Fmoc-prolyl ester as a yellow oil.

THC N-Fmoc-prolyl ester (99.7 mg) was dissolved in dry dichloromethane containing 10% (v/v) of thiophenol and 1.5% (v/v) of TFA. After 15 min the mixture was poured into cold saturated sodium bicarbonate and extracted with dichloromethane (2×30 mL). The combined organic layers were washed with cold water (30 mL), dried over anhydrous sodium sulfate, and concentrated to approximately 2 mL.

The solution of the crude product was chromatographed on silica gel with dichloromethane-methanol (gradient 100:0, 100:1, 50:1, 40:1, 30:1). The combined fractions containing the product were diluted with chloroform, concentrated at 25° C. to about 10 mL, diluted with chloroform and concentrated again to about 1 mL. The solution of the product was diluted with chloroform again (about 20 mL) and concentrated to dryness. The remaining oil was immediately dissolved in 1 mL of chloroform, concentrated to dryness, and immediately dissolved in 2 mL of chloroform to afford a stock solution of ALL00125 (about 30 mg/mL) that was stored at −20° C. Samples required for data collection were prepared by concentrating the stock solution immediately before the experiments.

For ALL00125, the $^1$H NMR (400 MHz, CDCl$_3$) was as follows: δ=6.56(1H, d, J=1.6, H-4); 6.41(1H, d, J=1.6, H-2); 5.92-5.95 (1H, m, H-10); 4.03(1H, br t, J=6.7); 3.10-3.21 (1H, m, H-10a); 2.93-3.09(2H, m); 2.49(2H, t, J=7.6, ArCH$_2$); 2.20-2.32(1H, m); 2.04-2.18(3H, m); 1.75-1.95 (6H, m); 1.63-1.71(4H, m); 1.52-1.62(2H, m); 1.41(3H, s, 6β-Me); 1.23-1.41(5H, m); 1.09(3H, s, 6α-Me); 0.88 (3H, t, J=7.0, CH$_2$CH).

5.0 Plasma Stability Studies

Approximately 1 mg/mL of stock solution of each prodrug was prepared in 100 μL of ethanol and 900 μL of acetonitrile. Next, 10 μL of stock was spiked into 1 mL of plasma and vortexed. The samples were kept sealed in an amber vial and samples were obtained to analyze for bioconversion to parent drug.

6.0 In Vitro Skin Permeation Studies 6.1 Preparation of Receiver Fluid

Initially 25% aqueous ethanol was used for the receiver fluid but the profiles were not typical and did not have enough time points to obtain a linear drug profile. A comparison between the 25% aqueous ethanol and 40% aqueous PEG 400 receiver fluids was examined. The 40% PEG 400 gave the typical profile and had higher concentrations of the respective drug so it was the receiver fluid used for the remainder of the diffusion studies. The receiver fluid was prepared by measuring 900 mL of nanopure H$_2$O into a graduated cylinder. The H$_2$O was filtered through a 0.2μ filter (Millipore, Billerica, Mass.). In addition, 75 mg of gentamicin was added to the filtered H$_2$O and 600 mL of PEG 400 was added.

6.2 Preparation of Drug Formulations

Four different formulations were used for charging the donor compartment. Drugs were made up in either 100%

PG, 1:1:1 PG:ethanol:H$_2$O, 2.36:1.18:1 PG:ethanol:H$_2$O, or a gel formulation. For the solutions, the appropriate amount of drug was weighed into a glass silanized culture tube and ethanol was added to get the drug into solution, then PG was added and water was added last. The gel formulation was comprised of absolute ethanol, H$_2$O, isopropyl myristate, Carbopol® 980, 0.1 N sodium hydroxide solution and respective drug.

6.3 Permeation Experiments (i) Dermatomed skin harvested from abdominoplasty and stored at −20° C. was used for the experiments. A PermeGear flow-through (In-Line, Hellertown, Pa.) diffusion cell system was used for the skin permeation studies.

(ii) Diffusion cells were kept at 32° C. with a circulating water bath. Human epidermal skin was arranged in the diffusion cell with stratum corneum (upper layer of skin) facing the donor compartment. Permeation area of the skin was 0.95 cm$^2$. Data was collected from a human skin donor with three diffusion cells per treatment.

(iii) Receiver solution was 25% aqueous ethanol or 40% aqueous PEG 400 and flow rate was adjusted to 0.8 mL/h. Each cell was charged with 50 or 100 μL of the respective drug formulation (donor solution) or with 35 μL of gel formulation which was rubbed into the skin for 15 sec with a Teflon coated rod. The formulation was applied to ensure complete coverage. Diffusion cells were covered with a stopper for the duration of the study.

(iv) Samples were collected into scintillation vials in 3 h increments for 24 h. All the samples were stored at 4° C. until extracted. A 1 mL aliquot of the 25% aqueous ethanol diffusion samples was placed into silanized HPLC vials or an aliquot (500 μL) of the 40% PEG 400 diffusion sample was placed into a silanized HPLC vial and 500 μL of acetonitrile was added to the sample, capped and vortexed.

(v) At the end of the experiment, the skin tissue was removed from the diffusion cell, rinsed with nanopure water, and blotted dry with a paper towel. The skin was tape stripped twice using book tape (Scotch™, 3M, St. Paul, Minn.) to remove drug formulation adhering to the tissue surface. The area of skin in contact with the drug was excised, chopped up and placed in a pre-weighed scintillation vial. Ten mL of acetonitrile was added to the vial and drug was extracted from the skin by shaking at room temperature overnight. The samples were analyzed by HPLC.

(vi) At the end of the experiment, a 10 μL aliquot of donor solution was removed and added to a scintillation vial containing 10 mL of acetonitrile. The vials were vortexed and then sonicated for 15 min. An aliquot of 1 mL was removed and transferred into a silanized HPLC vial for analysis.

7.0 Analytical Method

| | |
|---|---|
| Column | Brownlee® C$_8$ reversed phase Spheri 5 μm, (4.6 × 220 mm) column with a Brownlee® C$_8$ reversed phase 7 μm (3.2 × 150 mm) guard column or Symmetry® C$_{18}$ 5 μm (2.1 × 150 mm) column |
| Mobile phase | 70:30 acetonitrile:0.05% trifluroacetic acid with 5% acetonitrile, 82:18 acetonitrile:0.05% trifluroacetic acid with 5% acetonitrile or 95:5 (74:21:5 methanol:H$_2$O:THF):(95:5 H$_2$O:acetonitrile) |
| Flow rate | 0.5 mL/min or 1.5 mL/min |
| Wavelength | 210 nm |
| Injection volume | 50 μL or 100 μL (diffusion samples and respective standards) 10 μL or 20 μL (skin samples, donor samples, and respective standards) |
| Run time | 7-21 min |
| Retention times | Δ$^9$-tetrahydrocannabinol = 6.2-6.4, 11.4-12.4 min |
| | ALL00117 = 8.4-8.9 min |
| | ALL00118 = 12.7-13.2 min |
| | ALL00119 = 8.3-8.4, 14 min |
| | ALL00120 = 5.1 min |
| | ALL00121 = 9.7-10.2 min |
| | ALL00122 = 9.5 min |
| | ALL00123 = 10.7 min |
| | ALL00124 = 9.7-9.8, 19.8 min |
| | ALL00125 = 15.0 min |

8.0 Data Analysis

The cumulative quantity of drug collected in the receiver compartment was plotted as a function of time. The flux value for a given experiment was obtained from the slope of a steady state portion of the cumulative amount of drug permeated versus time plot. Lag time was obtained from the x-intercept of the steady state portion of the cumulative amount of drug permeated vs. time plot. The combined results of the delivered prodrug and Δ$^9$-tetrahydrocannabinol from the prodrug are listed as "total Δ$^9$-tetrahydrocannabinol." These values represent the data as total Δ$^9$-tetrahydrocannabinol equivalents delivered in the form of Δ$^9$-tetrahydrocannabinol and/or prodrug.

Section III. Tables

TABLE 1

Δ$^9$-Tetrahydrocannabinol and Δ$^9$-tetrahydrocannabinol prodrugs

| Compound | Molecular formula | Molecular weight |
|---|---|---|
| Δ$^9$-tetrahydrocannabinol | C$_{21}$H$_{30}$O$_2$ | 314.46 |
| ALL00117 | C$_{30}$H$_{46}$O$_7$ | 518.68 |
| ALL00118 | C$_{25}$H$_{37}$NO$_3$ | 399.57 |
| ALL00119 | C$_{31}$H$_{48}$O$_8$ | 548.71 |
| ALL00120 | C$_{24}$H$_{33}$NO$_4$ | 399.50 |
| ALL00121 | C$_{25}$H$_{35}$NO$_4$ | 413.55 |
| ALL00122 | C$_{32}$H$_{48}$O$_9$ | 576.72 |
| ALL00123 | C$_{25}$H$_{34}$O$_5$ | 414.53 |
| ALL00124 | C$_{26}$H$_{40}$N$_2$O$_3$ | 428.61 |
| ALL00125 | C$_{26}$H$_{37}$NO$_3$ | 411.58 |

TABLE 2

Permeation data of Δ⁹-tetrahydrocannabinol (n = 2) and ALL00117 (n = 3) with 100% PG donor solution

| Compound | 24 h skin conc (μmol/g) | 24 h cumulative amt (nmol) | Flux (nmol/cm²/h) | Lag time (h) |
|---|---|---|---|---|
| $\Delta^9$-tetrahydrocannabinol | 74.8 ± 15.5 | 6.9 ± 2.1 | — | — |
| ALL00117 | 8.9 ± 7.1 (PD) 1.1 ± 0.0 (THC) | — | — | — |

TABLE 3

Permeation data of Δ⁹-tetrahydrocannabinol (n = 3) and ALL00118 (n = 3) with 1:1:1 PG:ethanol:H₂O donor solution

| Compound | 24 h skin conc (μmol/g) | 24 h cumulative amt (nmol) | Flux (nmol/cm²/h) | Lag time (h) |
|---|---|---|---|---|
| $\Delta^9$-tetrahydrocannabinol | 59.4 ± 30.5 | 9.0 ± 5.9 | 0.93 ± 0.58 | 13.0 ± 1.8 |
| ALL00118 | 37.3 ± 23.2 (PD) 7.1 ± 2.4 (THC) | — | — | — |

TABLE 4

Permeation data of Δ⁹-tetrahydrocannabinol (n = 2), ALL00117 (n = 1), and ALL00118 (n = 3) with gel formulation

| Compound | 24 h skin conc (μmol/g) | 24 h cumulative amt (nmol) | Flux (nmol/cm²/h) | Lag time (h) |
|---|---|---|---|---|
| $\Delta^9$-tetrahydrocannabinol | 100.4 ± 5.8 | 1.5 ± 0.3 | 0.14 ± 0.03 | 11.2 ± 2.7 |
| ALL00117 | 13.8 ± 4.1 (PD) 0.7 ± 0.1 (THC) | 1.7 ± 0.0 | 0.07 ± 0.00 | — |
| ALL00118 | 48.8 ± 30.2 (PD) 65.9 ± 24.7 (THC) | — | — | — |

TABLE 5

Permeation data of Δ⁹-tetrahydrocannabinol (n = 2) with 1:1:1 PG:ethanol:H₂O donor solution and higher flow rate

| Compound | 24 h skin conc (μmol/g) | 24 h cumulative amt (nmol) | Flux (nmol/cm²/h) | Lag time (h) |
|---|---|---|---|---|
| $\Delta^9$-tetrahydrocannabinol | 133.8 ± 52.3 | 6.0 ± 2.1 | 0.67 ± 0.15 | 8.9 ± 7.2 |

TABLE 6

Permeation data of Δ⁹-tetrahydrocannabinol (n = 2) with 1:1:1 PG:ethanol:H₂O donor solution and comparison of two different receiver fluids

| Compound | 24 h skin conc (μmol/g) | 24 h cumulative amt (nmol) | Flux (nmol/cm²/h) | Lag time (h) |
|---|---|---|---|---|
| $\Delta^9$-tetrahydrocannabinol (25% aqueous ethanol) | 24.1 ± 5.2 | 9.4 ± 0.2 | 0.70 ± 0.01 | 6.9 ± 0.2 |
| $\Delta^9$-tetrahydrocannabinol (40% aqueous PEG 400) | 17.4 ± 11.6 | 28.6 ± 3.2 | 1.79 ± 0.39 | 6.4 ± 1.6 |

TABLE 7

Permeation data of Δ⁹-tetrahydrocannabinol (n = 2), ALL00120 (n = 3), ALL00121 (n = 2) and ALL00123 (n = 3) with 2.36:1.18:1 PG:ethanol:$H_2O$ donor solution

| Compound | 24 h skin conc (μmol/g) | 24 h cumulative amt (nmol) | Flux (nmol/cm²/h) | Flux enhancement | Lag time (h) |
|---|---|---|---|---|---|
| $\Delta^9$-tetrahydrocannabinol (THC) | 75.2 ± 33.1 | 43.1 ± 4.8 | 3.1 ± 0.2 | — | 9.0 ± 2.9 |
| total $\Delta^9$-tetrahydrocannabinol * | 50.2 ± 7.1 | 39.3 ± 6.6 | 2.7 ± 0.5 | 0.87 | 8.4 ± 1.3 |
| ALL00120 | 47.1 ± 6.3 | 30.5 ± 7.0 | 2.0 ± 0.5 | | 8.1 ± 1.6 |
| THC from ALL00120 | 3.1 ± 1.1 | 8.8 ± 1.2 | 0.6 ± 0.1 | | 9.2 ± 0.8 |
| total $\Delta^9$-tetrahydrocannabinol * | 72.3 ± 54.0 | 22.4 ± 6.5 | 1.5 ± 0.4 | 0.66 | 8.5 ± 0.8 |
| ALL00121 | 72.3 ± 54.0 | 18.5 ± 5.6 | 1.2 ± 0.3 | | 8.3 ± 0.5 |
| THC from ALL00121 | ND | 3.9 ± 1.0 | 0.3 ± 0.0 | | 8.8 ± 1.2 |
| total $\Delta^9$-tetrahydrocannabinol * | 60.7 ± 15.9 | 48.7 ± 7.4 | 3.1 ± 0.6 | 1.03 | 7.6 ± 1.5 |
| ALL00123 | ND | ND | — | | — |
| THC from ALL00123 | 60.7 ± 15.9 | 48.7 ± 7.4 | 3.1 ± 0.6 | | 7.6 ± 1.5 |

* total THC = total $\Delta^9$-tetrahydrocannabinol equivalents delivered in the form of $\Delta^9$-tetrahydrocannabinol and/or prodrug

TABLE 8

Permeation data of Δ⁹-tetrahydrocannabinol (n = 2), ALL00120 (n = 3), ALL00121 (n = 2) and ALL00123 (n = 3) with gel formulation

| Compound | 24 h skin conc (μmol/g) | 24 h cumulative amt (nmol) | Flux (nmol/cm²/h) | Flux enhancement | Lag time (h) |
|---|---|---|---|---|---|
| $\Delta^9$-tetrahydrocannabinol (THC) | 40.9 ± 14.7 | 10.7 ± 2.1 | 0.62 ± 0.23 | — | 5.3 ± 3.3 |
| total $\Delta^9$-tetrahydrocannabinol * | 47.9 ± 2.8 | — | — | — | — |
| ALL00120 | 44.8 ± 1.6 | — | — | | — |
| THC from ALL00120 | 3.1 ± 2.1 | — | — | | — |
| total $\Delta^9$-tetrahydrocannabinol * | 33.2 ± 7.2 | 10.5 ± 0.5 | 0.53 ± 0.05 | 0.85 | 3.0 ± 2.8 |
| ALL00121 | 33.2 ± 7.2 | 8.8 ± 0.1 | 0.38 ± 0.03 | | 1.4 ± 0.0 |
| THC from ALL00121 | ND | 1.7 ± 0.4 | 0.15 ± 0.01 | | 11.6 ± 4.1 |
| total $\Delta^9$-tetrahydrocannabinol * | 110.4 ± 22.2 | 17.5 ± 4.0 | 0.67 ± 0.18 | 1.08 | — |
| ALL00123 | 110.4 ± 22.2 | 2.3 ± 1.5 | 0.15 ± 0.07 | | — |
| THC from ALL00123 | ND | 15.2 ± 2.5 | 0.52 ± 0.13 | | 5.6 ± 4.3 |

* total THC = total $\Delta^9$-tetrahydrocannabinol equivalents delivered in the form of $\Delta^9$-tetrahydrocannabinol and/or prodrug

TABLE 9

Permeation data of Δ⁹-tetrahydrocannabinol (n = 2), ALL00119 (n = 3), ALL00122 (n = 2) and ALL00124 (n = 2) with 2.36:1.18:1 pH = 5.5 PG:ethanol:$H_2O$ donor solution

| Compound | 24 h skin conc (μmol/g) | 24 h cumulative amt (nmol) | Flux (nmol/cm²/h) | Flux enhancement | Lag time (h) |
|---|---|---|---|---|---|
| $\Delta^9$-tetrahydrocannabinol (THC) | 16.1 ± 0.5 | 16.3 ± 7.3 | 1.3 ± 0.5 | — | 11.4 ± 0.6 |
| total $\Delta^9$-tetrahydrocannabinol * | 13.6 ± 7.5 | ND | — | — | — |
| ALL00119 | 13.6 ± 7.5 | ND | — | | — |
| THC from ALL00119 | ND | ND | — | | — |
| total $\Delta^9$-tetrahydrocannabinol * | 56.5 ± 3.8 | 6.0 ± 0.7 | 0.5 ± 0.03 | 0.36 | 11.0 ± 0.8 |
| ALL00122 | 52.7 ± 3.2 | ND | — | | — |
| THC from ALL00122 | 3.8 ± 0.6 | 6.0 ± 0.7 | 0.3 ± 0.0 | | 11.0 ± 0.8 |
| total $\Delta^9$-tetrahydrocannabinol * | 67.4 ± 11.3 | 145.2 ± 105.2 | 9.9 ± 6.2 | 7.35 | 9.1 ± 1.8 |

TABLE 9-continued

Permeation data of Δ⁹-tetrahydrocannabinol (n = 2), ALL00119 (n = 3), ALL00122 (n = 2) and ALL00124 (n = 2) with 2.36:1.18:1 pH = 5.5 PG:ethanol:$H_2O$ donor solution

| Compound | 24 h skin conc (μmol/g) | 24 h cumulative amt (nmol) | Flux (nmol/cm²/h) | Flux enhancement | Lag time (h) |
|---|---|---|---|---|---|
| ALL00124 | 17.3 ± 0.4 | 138.7 ± 101.2 | 9.4 ± 5.9 | | 9.1 ± 2.0 |
| THC from ALL00124 | 50.1 ± 11.0 | 6.5 ± 4.0 | 0.5 ± 0.4 | | 7.6 ± 3.3 |

\* total THC = total Δ⁹-tetrahydrocannabinol equivalents delivered in the form of Δ⁹-tetrahydrocannabinol and/or prodrug

TABLE 10

Permeation data of Δ⁹-tetrahydrocannabinol (n = 3), ALL00124 (n = 2), and ALL00125 (n = 3) with 2.36:1.18:1 pH = 5.5 PG:ethanol:$H_2O$ donor solution

| Compound | 24 h skin conc (μmol/g) | 24 h cumulative amt (nmol) | Flux (nmol/cm²/h) | Flux enhancement | Lag time (h) |
|---|---|---|---|---|---|
| Δ⁹-tetrahydrocannabinol (THC) | 7.4 ± 0.6 | 33.6 ± 11.2 | 2.7 ± 1.1 | — | 10.8 ± 1.4 |
| total Δ⁹-tetrahydrocannabinol* | 4.8 ± 0.4 | 253.3 ± 56.9 | 16.7 ± 0.4 | 6.13 | 1.3 ± 0.0 |
| ALL00124 | 4.3 ± 0.3 | 245.2 ± 54.1 | 16.1 ± 0.1 | | 1.4 ± 0.0 |
| THC from ALL00124 | 0.5 ± 0.1 | 9.3 ± 2.9 | 0.6 ± 0.2 | | 1.1 ± 0.0 |
| total Δ⁹-tetrahydrocannabinol * | 1.4 ± 1.0 | 17.4 ± 8.8 | 1.3 ± 0.6 | 0.49 | 10.7 ± 1.7 |
| ALL00125 | ND | ND | — | | — |
| THC from ALL00125 | 1.4 ± 1.0 | 17.4 ± 8.8 | 1.3 ± 0.6 | | 10.7 ± 1.7 |

\* total THC = total Δ⁹-tetrahydrocannabinol equivalents delivered in the form of Δ⁹-tetrahydrocannabinol and/or prodrug

TABLE 11

Plasma stability of Δ⁹-tetrahydrocannabinol prodrugs
% Prodrug at time (h)

| Prodrug | 0.1 | 1 | 2 | 3 | 5 | 22 | 24 | 42 |
|---|---|---|---|---|---|---|---|---|
| ALL00118 | 100 | 94 | — | — | — | 86 | 81 | 15 |
| ALL00119 | 100 | 82 | — | — | — | 64 | 51 | 0 |
| ALL00120 | 70 | 8 | — | — | — | 0 | 0 | 0 |
| ALL00121 | 100 | 50 | — | — | — | 10 | 14 | 0 |
| ALL00122 | 0 | 0 | — | — | — | 0 | 0 | 0 |
| ALL00123 | 0 | 0 | — | — | — | 0 | 0 | 0 |
| ALL00124 | 97 | 97 | 97 | 96 | 94 | — | 71 | — |
| ALL00125 | 100 | — | 77 | — | 55 | 0 | 0 | 0 |

Example 2

Section I. Summary

The objective was to synthesize additional Δ⁹-tetrahydrocannabinol prodrugs and assess the permeation of Δ⁹-tetrahydrocannabinol and its prodrugs through human abdominal skin in vitro. Four additional Δ⁹-tetrahydrocannabinol prodrugs were synthesized, three of which were tested. Synthesized prodrugs of Δ⁹-tetrahydrocannabinol were analyzed for plasma stability to monitor the rate of conversion to Δ⁹-tetrahydrocannabinol. Potential candidates would convert readily to Δ⁹-tetrahydrocannabinol in plasma whereas there would only be minimal conversion of stable prodrugs. Flow through diffusion cells were used for the permeation studies. The receiver used for the permeation studies was 40% aqueous PEG (polyethylene glycol) 400. Donor solution was comprised of a rubbed in gel formulation. The flux and lag time values of Δ⁹-tetrahydrocannabinol and Δ⁹-tetrahydrocannabinol prodrugs were obtained from the permeation profiles. Drug accumulation in the skin after a 24 h diffusion experiment was determined as μmol/g wet tissue weight.

Section II. Methodology 1.0 Purpose: Synthesize Δ⁹-tetrahydrocannabinol prodrugs and assess the human skin permeation of Δ⁹-tetrahydrocannabinol and Δ⁹-tetrahydrocannabinol prodrugs in vitro. The following compounds were synthesized:

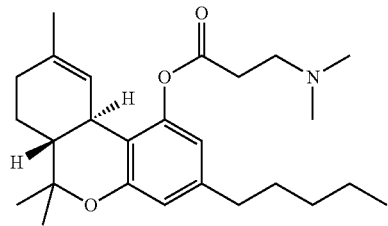

ALL00153
MW: 413.59
Formula $C_{26}H_{39}NO_3$

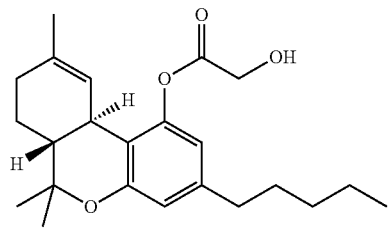

ALL00154
MW: 372.50
Formula $C_{23}H_{32}O_4$

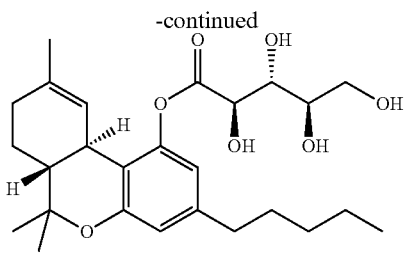

ALL00155
MW: 462.58
Formula C<sub>26</sub>H<sub>38</sub>O<sub>7</sub>

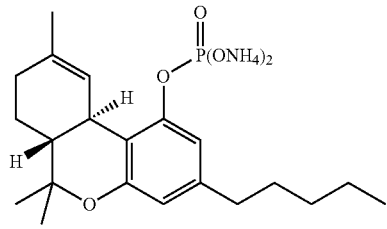

ALL00156
$C_{21}H_{37}N_2O_5P$
Mol. Wt.: 428.50

2.0 Skin Details

The skin samples used in the following experiments were obtained from abdominal reduction surgery and dermatomed to a thickness of approximately 200 μm. The skin samples used herein were frozen at −20° C. for less than six months.

3.0 Chemicals

Trifluoroacetic acid, triethylamine, gentamicin sulfate, acetone, (t-butyldimethylsilyloxy)acetic acid, dichloromethane (DCM), 4-dimethylaminopyridine (DMAP), and sodium bicarbonate were purchased through Fisher Scientific (Fairlawn, N.J.). Methanol (HPLC grade), acetonitrile (HPLC grade), ethyl acetate, hexane, N,N'-dicyclohexylcarbodiimide, 3-dimethylaminopropionic acid hydrochloride and polyethylene glycol 400 (PEG 400) were purchased through VWR (West Chester, Pa.). Absolute ethanol USP, triethylamine trihydrofluoride, ribonic acid diacetonide, and Δ⁹-tetrahydrocannabinol were purchased from Sigma-Aldrich (St. Louis, Mo.) Anhydrous sodium sulfate was purchased from UK Stores (Lexington, Ky.). Argon and pre-purified nitrogen were purchased from Scott Gross Company (Lexington, Ky.). Carbopol® 980 was obtained from Noveon, Inc. (Cleveland, Ohio). Nanopure water was obtained from a Barnstead NANOpure® DIamond™ Ultrapure water filtration system (Dubuque, Iowa).

4.0 Synthesis of Δ⁹-tetrahydrocannabinol prodrugs 4.1 Synthesis of ALL00153 (Δ⁹-Tetrahydrocannabinol 3-(dimethylamino)propionate)

THC (46 mg, 0.00015 mol), 3-dimethylaminopropionic acid hydrochloride (28 mg, 0.00018 mol), and DMAP (27 mg, 0.00022 mol) were combined in 1 mL dry dichloromethane. The solution was stirred for 5 min at ambient temperature. DCC (45 mg, 0.00022 mol) was added to the mixture. The mixture was allowed to stir for 3 h at ambient temperature. Dichloromethane was removed from the reaction mixture under a stream of nitrogen. The sample was reconstituted in acetonitrile and the solids removed by filtration. The solution was reduced to a small volume under nitrogen. ALL00153 was isolated using a semi-preparatory C8 HPLC column with ACN:pH 3 buffer (80:20) as mobile phase. The ACN was removed from the eluent fraction containing ALL00153 by rotary evaporation under reduced pressure. The pH of the remaining aqueous layer was adjusted to pH 8 using 1% sodium bicarbonate. The aqueous layer was partitioned with three times with DCM and the combined DCM fractions dried over sodium sulfate. DCM was removed by rotary evaporation. The purified product appeared as transparent, viscous oil with light amber color.

ALL00153 was analyzed by LC/MS in electrospray positive ion mode. The mass of the compound was confirmed by the observation of the molecular ion at 414.342 (M+1, 100%).

For ALL00153, the 1H NMR (400 MHz, CDCl<sub>3</sub>) was as follows: δ=6.55(1H, d, J=1.8, H-4); 6.41(1H, d, J=1.8, H-2); 5.93-5.97(1H, m, H-10); 3.02-3.09(1H, m, H-10a); 2.70-2.84 (4H, m, COCH<sub>2</sub>CH<sub>2</sub>); 2.45-2.53(2H, m, benzylic CH<sub>2</sub>); 2.32(6H, s, N(CH<sub>3</sub>)<sub>2</sub>); 2.10-2.17(2H, m); 1.86-1.95(1H, m); 1.64-1.73(4H, m); 1.52-1.64(2H, m); 1.41(3H, s, 6β-Me); 1.23-1.40(5H, m); 1.08(3H, s, 6α-Me); 0.88(3H, t, J=7.0, CH<sub>2</sub>CH<sub>3</sub>).

4.2 Synthesis of ALL00154 (Δ⁹-Tetrahydrocannabinol glycolate)

To a stirred solution of THC (78.6 mg, 0.25 mmol) and (t-butyldimethylsilyloxy)acetic acid (71.4 mg, 0.375 mmol) in dichloromethane (0.5 mL), 4-dimethylaminopyridine was added (6.1 mg, 0.05 mmol) followed by N,N'-dicyclohexylcarbodiimide (103.2 mg, 0.5 mmol). The mixture was stirred at ambient temperature for 2 h. Additional amounts of (t-butyldimethylsilyloxy)acetic acid (80 mg, 0.42 mmol) and N,N'-dicyclohexylcarbodiimide (110 mg, 0.53 mmol) were added and stirring was continued for 1 h. The mixture was diluted with hexane (1.5 mL), filtered, concentrated under a reduced pressure and chromatographed on silica gel with hexane-ethyl acetate (gradient 50:1, 40:1) to afford Δ⁹-tetrahydrocannabinol (t-butyldimethylsilyloxy)acetate (69.9 mg, 57.4%) as an oil.

Next, Δ⁹-tetrahydrocannabinol (t-butyldimethylsilyloxy) acetate (67.8 mg) was dissolved in dichloromethane (0.25 mL), cooled to −15° C. and treated with 0.25 mL of cold 2N solution of triethylamine trihydrofluoride in dichloromethane. The reaction mixture was left at 5° C. for 48 h. The mixture was poured to an excess of aqueous saturated sodium bicarbonate/ethyl acetate cooled to 0° C. with vigorous stirring. The aqueous layer was extracted twice with ethyl acetate. The combined organic extracts were dried over anhydrous sodium sulfate and concentrated. The residue was chromatographed on silica gel with hexane-ethyl acetate (gradient 30:1, 20:1, 10:1) to afford 38.5 mg (74%) of Δ 9-tetrahydrocannabinol glycolate (ALL00154) as an oil.

For ALL00154, the 1H NMR (400 MHz, CDCl<sub>3</sub>) was as follows: δ=6.58(1H, d, J=1.6, H-4); 6.43(1H, d, J=2.0, H-2); 5.82-5.87(1H, m, H-10); 4.36-4.50(2H, AB part of ABX, 8 lines, COCH<sub>2</sub>); 3.01-3.09(1H, m, H-10a); 2.46-2.54(2H, m, benzylic CH<sub>2</sub>); 2.40(1H, t(X part of ABX), J=5.6, OH); 2.10-2.20(2H, m); 1.86-1.95(1H, m); 1.62-1.72(4H, m); 1.52-1.62(2H, m); 1.41(3H, s, 6β-Me); 1.23-1.40(5H, m); 1.09(3H, s, 6α-Me); 0.88(3H, t, J=7.0, CH<sub>2</sub>CH<sub>3</sub>).

4.3 Synthesis of ALL00155 (Δ⁹-Tetrahydrocannabinol D-ribonate)

THC (63.8 mg, 0.00018 m) and ribonic acid diacetonide ((2R,3R,4R)-2,3:4,5-di-O-isopropylidene-2,3,4,5-tetrahydroxypentanoic acid) (63.8 mg, 0.00026 m) were combined in 0.5 mL DCM. DMAP (2.1 mg, 0.00002 m) was added and the solution stirred briefly. DCC (535.5 mg, 0.00026 m) was added and the mixture stirred for 2 h. Hexane (1.5 mL) was added and the mixture filtered. The filtrate was reduced to a small volume under nitrogen. The product (62.5 mg) was isolated using silica column chromatography and a 80:20 hexane:ethyl acetate.

For Δ$^9$-tetrahydrocannabinol D-ribonate diacetonide, the 1H NMR (400 MHz, CDCl$_3$) was as follows: δ=6.56(1H, d, J$_{AB}$=2.0, H-4); 6.54(1H, d, J$_{AB}$=1.6, H-2); 5.99-6.03(1H, m, H-10); 4.94(1H, d, J=6.4); 4.39(1H, dd, J$_1$=9.2, J$_2$=6.4); 4.21-4.27(1H, m); 4.14(1H, dd, J$_1$=8.8, J$_2$=6.4); 4.01(1H, dd, J$_1$=8.8, J$_2$=5.2); 3.10-3.18(1H, m, H-10a); 2.44-2.52(2H, m, benzylic CH$_2$); 2.08-2.17(2H, m); 1.84-1.92(1H, m); 1.62-1.70(4H, m); 1.51-1.60(2H, m); 1.50(3H, s, acetonide CH$_3$); 1.42(3H, s, acetonide CH$_3$); 1.41(3H, s, 6β-Me); 1.38(3H, s, acetonide CH$_3$); 1.23-1.38(5H, m); 1.09(3H, s, 6α-Me); 0.87 (3H, t, J=7.0, CH$_2$CH$_3$).

It is understood that a person of ordinary skill in the art would be able to deprotect Δ$^9$-tetrahydrocannabinol D-ribonate diacetonide to form ALL00155, using one of many available acetonide deprotection methods.

4.4 Synthesis of ALL00156 (Δ$^9$-Tetrahydrocannabinol phosphate ammonium salt)

To a stirred solution of solution of THC (10.9 mg, 0.0347 mmol) in anhydrous THF (0.2 mL) at 0° C. under an argon atmosphere was added triethylamine (0.0314 mL, 0.2253 mmol) followed by phosphorus oxychloride (0.00635 mL, 0.0693 mmol). After stirring for 2 hr at 0° C., triethylamine (0.020 mL) was added followed by water (0.030 mL). The mixture was stirred at ambient temperature for 24h and the product was purified using a Waters SymmetryPrep® C8 column (7.8×300 mm, 7 μm particle size) and mobile phase consisting of 70:30 (0.5% Ammonium carbonate:ACN) and UV detection at 230 nm (RT 15 min).

For ALL00156, the $^1$H NMR (400 MHz, CDCl$_3$-CD$_3$OD~10:1) was as follows: δ=6.80(1H, br s, H-4); 6.41 (1H, br s, H-10); 6.38(1H, br s, H-2); 4.02(8H, br s, NH$_4$); 3.30-3.35(1H, m); 2.45(2H, t, J=7.8, ArCH$_2$); 2.09-2.18(2H, m); 1.86-1.94(1H, m); 1.50-1.71(6H, m); 1.40(3H, s, 6β-Me); 1.23-1.40(5H, m); 1.07(3H, s, 6α-Me); 0.87 (3H, t, J=6.8, CH$_2$CH$_3$).

ALL00156 was analyzed by LC/MS in electrospray negative ion mode. The mass of the compound confirmed by the observation of the THC-P(O)(OH)O$^-$ ion at 393.090 (M−1, 100%) and the dimmer at 787.709 (13.5%).

5.0 Plasma Stability Studies

An approximated 1 mg/mL stock solution of each prodrug was prepared in 100 μL of ethanol and 900 μL of acetonitrile. Next, 10 μL of stock was spiked into 1 mL of plasma and vortexed. The samples were kept sealed in an amber vial and samples were obtained to analyze for bioconversion to parent drug.

6.0 In Vitro Skin Permeation Studies 6.1 Preparation of Receiver Fluid

The receiver fluid was prepared by measuring 600 mL of nanopure H$_2$O into a graduated cylinder. The H$_2$O was filtered through a 0.2μ filter (Millipore, Billerica, Mass.). Next, 50 mg of gentamicin was added to the filtered H$_2$O and 400 mL of PEG 400 was added.

6.2 Preparation of Drug Formulations

Drugs were made up in a gel formulation. The gel formulation was comprised of absolute ethanol, H$_2$O, Carbopol® 980, 0.1 N sodium hydroxide solution and respective drug.

6.3 Permeation Experiments

Dermatomed skin harvested from abdominoplasty and stored at −20° C. was used for the experiments. A PermeGear flow-through (In-Line, Hellertown, Pa.) diffusion cell system was used for the skin permeation studies.

Diffusion cells were kept at 32° C. with a circulating water bath. Human epidermal skin was arranged in the diffusion cell with stratum corneum (upper layer of skin) facing the donor compartment. Permeation area of the skin was 0.95 cm$^2$. Data was collected from a human skin donor with three diffusion cells per treatment.

Receiver solution was 40% aqueous PEG 400 and flow rate was adjusted to 0.8 mL/h. Each cell was charged with 50 μL of gel formulation which was rubbed into the skin for 15 sec with a Teflon coated rod. The formulation was applied to ensure complete coverage. Diffusion cells were covered with a cap for the duration of the study.

Samples were collected into scintillation vials in 3 h increments for 24 h. All the samples were stored at 4° C. until extracted. An aliquot (500 μL) of the 40% PEG 400 diffusion sample was placed into a silanized HPLC vial and 500 μL of acetonitrile was added to the sample, capped and vortexed.

At the end of the experiment, the skin was washed with 700 μL of acetonitrile and from the 700 μL of acetonitrile an aliquot of 10 μL was diluted in a scintillation vial containing 10 mL of acetonitrile. The vials were vortexed and then sonicated for 15 min. An aliquot of 1 mL was removed and transferred into a silanized HPLC vial for analysis.

At the end of the experiment, the skin tissue was removed from the diffusion cell, rinsed with nanopure water for 30 sec, and wiped off twice with an alcohol pad. The skin was tape stripped twice using book tape (Scotch™, 3M, St. Paul, Minn.) to remove drug formulation adhering to the tissue surface. The area of skin in contact with the drug was excised, chopped up and placed in a pre-weighed scintillation vial. Ten mL of acetonitrile was added to the vial and drug was extracted from the skin by shaking at room temperature overnight. The samples were analyzed by HPLC.

7.0 Analytical Method

| | |
|---|---|
| Column | Brownlee ® C8 reversed phase Spheri 5 μm, (4.6 × 220 mm) column with a |
| | Brownlee ® C8 reversed phase 7 μm (3.2 × 150 mm) guard column |
| Mobile phase | 90:10 acetonitrile: 0.05% trifluroacetic acid with 5% acetonitrile or |
| | 65:35 acetonitrile: 0.05% trifluroacetic acid with 5% acetonitrile |
| Flow rate | 1.5 mL/min |
| Wavelength | 210 nm |
| Injection volume | 100 μL (diffusion samples and respective standards) |
| | 20 μL (skin samples, donor samples, and respective standards) |
| Run time | 20-23 min |
| Retention times | Δ9-tetrahydrocannabinol = 3.9, 21.2 min |
| | ALL00153 = 17.9 min |
| | ALL00154 = 20.0 min |

8.0 Data Analysis

The cumulative quantity of drug collected in the receiver compartment was plotted as a function of time. The flux value for a given experiment was obtained from the slope of a steady state portion of the cumulative amount of drug permeated versus time plot. Lag time was obtained from the x-intercept of the steady state portion of the cumulative amount of drug permeated versus time plot. The combined results of the delivered prodrug and $\Delta^9$-tetrahydrocannabinol from the prodrug are listed as "total $\Delta^9$-tetrahydrocannabinol." These values represent the data as total $\Delta^9$-tetrahydrocannabinol equivalents delivered in the form of $\Delta^9$-tetrahydrocannabinol and/or prodrug.

Section III. Tables

TABLE 12

$\Delta^9$-Tetrahydrocannabinol and $\Delta^9$-tetrahydrocannabinol prodrugs

| Compound | Molecular formula | Molecular weight |
|---|---|---|
| $\Delta^9$-tetrahydrocannabinol | $C_{21}H_{30}O_2$ | 314.46 |
| ALL00153 | $C_{26}H_{39}NO_3$ | 413.59 |
| ALL00154 | $C_{23}H_{32}O_4$ | 372.50 |
| ALL00155 | $C_{26}H_{38}O_7$ | 462.58 |

TABLE 13

Permeation data of THC (n = 3), ALL00153 (n = 3), and ALL00154 (n = 1) in gel formulation with 40% aqueous PEG 400 receiver fluid

| Compound | 24 h skin conc (μmol/g) | 24 h cumulative amt (nmol) | Flux (nmol/cm²/h) | Flux enhancement | Lag time (h) |
|---|---|---|---|---|---|
| tetrahydrocannabinol (THC) | 3.6 ± 1.7 | 3.1 ± 0.8 | 0.17 ± 0.02 | — | 4.6 ± 3.2 |
| total tetrahydrocannabinol* | 2.9 ± 0.2 | 3.1 ± 1.3 | 0.18 ± 0.002 | 1.06 | 8.7 ± 6.7 |
| ALL00153 | 1.6 ± 0.03 | ND | — | | — |
| THC from ALL00153 | 1.3 ± 0.1 | 3.1 ± 1.3 | 0.18 ± 0.002 | | 8.7 ± 6.7 |
| total tetrahydrocannabinol* | 2.6 ± 1.5 | 40.7± | 3.37± | 19.82 | 12.4± |
| ALL00154 | 2.6 ± 1.5 | 39.2± | 3.23± | | 12.2± |
| THC from ALL00154 | ND | 1.6± | — | | — |

*total THC = total tetrahydrocannabinol equivalents delivered in the form of tetrahydrocannabinol and/or prodrug

TABLE 14

Plasma stability of Δ9-tetrahydrocannabinol prodrugs
% Prodrug at time (h)

| | Prodrug | | | |
|---|---|---|---|---|
| | 0 | 1 | 21 | 24 |
| ALL00153 | 98 | 72 | 48 | 41 |
| ALL00154 | 95 | 0 | 0 | 0 |

Example 3

Section I. Summary

The objective was to synthesize additional $\Delta^9$-tetrahydrocannabinol prodrugs and assess the permeation of $\Delta^9$-tetrahydrocannabinol and its prodrugs through human abdominal skin in vitro. Ten $\Delta^9$-tetrahydrocannabinol prodrugs were synthesized and eight were tested. Synthesized prodrugs of $\Delta^9$-tetrahydrocannabinol were analyzed for plasma stability to monitor the rate of conversion to $\Delta^9$-tetrahydrocannabinol. Potential candidates would convert readily to $\Delta^9$-tetrahydrocannabinol in plasma whereas stable prodrugs would convert very little. The procedure was performed to screen out compounds with no bioconversion to the parent drug. Flow through diffusion cells were used for the permeation studies. The receiver fluid used for the permeation studies was 40% aqueous PEG (polyethylene glycol) 400. Donor solution was comprised of 90:8:2 propylene glycol (PG):$H_2O$:isopropyl myristate (IPM). The flux and lag time values of $\Delta^9$-tetrahydrocannabinol and $\Delta^9$-tetrahydrocannabinol prodrugs were obtained from the permeation profiles. Drug accumulation in the skin after a 24 h diffusion experiment was determined as μmol/g wet tissue weight.

Section II. Methodology 1.0 Purpose: Synthesize $\Delta^9$-tetrahydrocannabinol prodrugs and assess the human skin permeation of $\Delta^9$-tetrahydrocannabinol and $\Delta^9$-tetrahydrocannabinol prodrugs in vitro. The following compounds were synthesized:

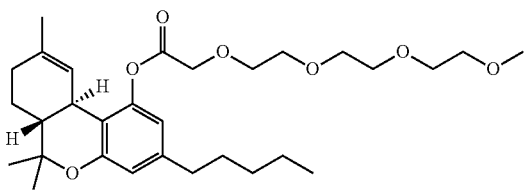

ALL00117
MW: 518.68
Formula: $C_{30}H_{46}O_7$

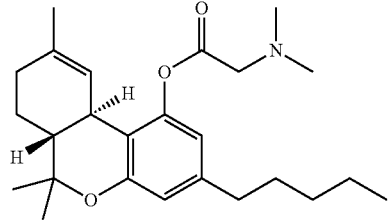

ALL00118
MW: 399.57
Formula: $C_{25}H_{37}NO_3$

-continued

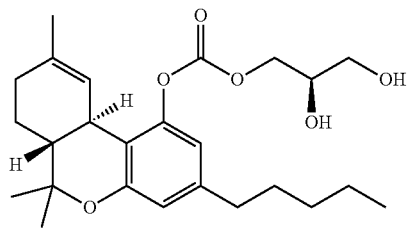

ALL00126
MW: 432.55
Formula: $C_{25}H_{36}O_6$

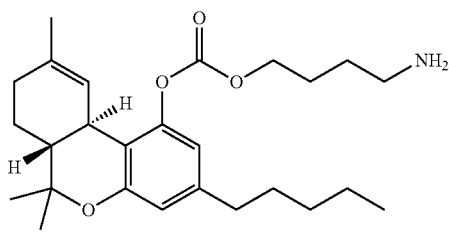

ALL00127
MW: 429.59
Formula: $C_{26}H_{39}NO_4$

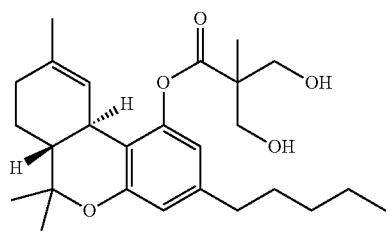

ALL00129
MW: 430.58
Formula: $C_{26}H_{38}O_5$

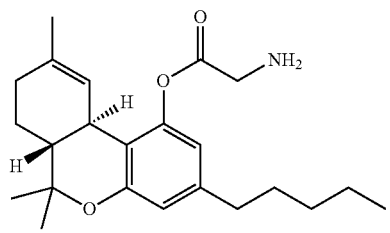

ALL00130
MW: 371.51
Formula: $C_{23}H_{33}NO_3$

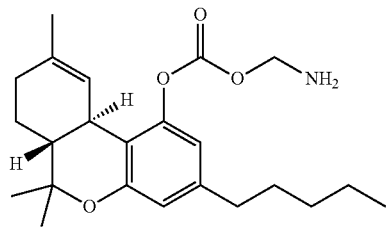

ALL00133
MW: 385.54
Formula: $C_{24}H_{35}NO_3$

-continued

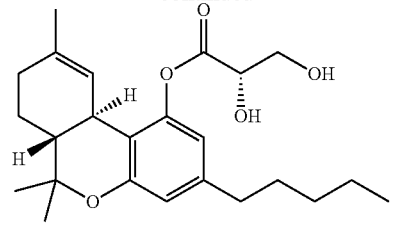

ALL00134
MW: 402.52
Formula: $C_{24}H_{34}O_5$

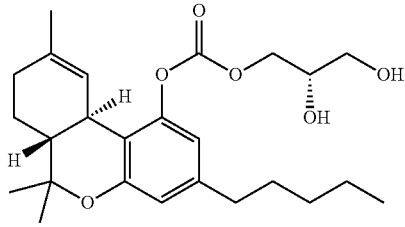

ALL00138
MW: 432.55
Formula: $C_{25}H_{36}O_6$

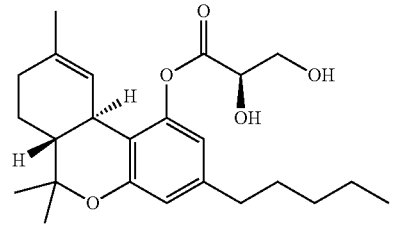

ALL00144
MW: 402.52
Formula: $C_{24}H_{34}O_5$ 2.0 Skin Details

The skin samples used in the following experiments were obtained from abdominal reduction surgery and dermatomed to a thickness of approximately 200 μm. The skin samples used herein were frozen at −20° C. for less than six months.

3.0 Chemicals

Trifluoroacetic acid, triethylamine, gentamicin sulfate, isopropyl myristate (IPM), dichloromethane, sodium bicarbonate, 4-dimethylaminopyridine, t-butyldimethylsilyl chloride, 1-octanethiol, R-(+)-1-benzylglycerol, and Fmoc-N-(4-hydroxybutyl)carbamate were purchased through Fisher Scientific (Fairlawn, N.J.). Methanol (HPLC grade), acetonitrile (HPLC grade), N,N'-dicyclohexylcarbodiimide, 1,8-diazabicyclo[5.4.0]undec-7-ene (DBU), imidazole, zinc trifluoromethanesulfanate, N,N-dimethylglycine, and polyethylene glycol 400 (PEG 400) were purchased through VWR (West Chester, Pa.). Delta-9-Tetrahydrocannabinol, propylene glycol (PG), triethylene glycol, methyl (S)-(−)-2,2-dimethyl-1,3-dioxolane-4-carboxylate, methyl (R)-(+)-2,2-dimethyl-1,3-dioxolane-4-carboxylate, (R)-(−)-Solketal, N-(2-nitrophenylsulfenyl)glycine dicyclohexylammonium salt, triphosgene, triethylamine trihydrofluroride, and thiophenol were purchased from Sigma-Aldrich (St. Louis, Mo.). Chloroform and anhydrous sodium sulfate were obtained from the University of Kentucky Chemical Stores (Lexington, Ky.). Argon and pre-purified nitrogen were purchased from Scott Gross Company (Lexington, Ky.). Nanopure water was obtained from a Barnstead NANOpure® DIamond™ Ultrapure water filtration system (Dubuque, Iowa). The following compounds were synthesized according to literature procedures: 5-carboxy-2,2,5-trimethyl-1,3-dioxane (Macromolecules, 31, 4061, 1998), 3,6,9,12-tetraoxatridecanoic acid (Macromolecules, 39 (12), 3978-3979, 2006.), and N-(2-nitrophenylsulfenyl)-β-alanine (JACS, 85, 3660, 1963).

4.0 Synthesis of $\Delta^9$-Tetrahydrocannabinol ($\Delta^9$-THC) prodrugs 4.1 Synthesis of ALL00117 ($\Delta^9$-Tetrahydrocannabinol 3,6,9,12-tetraoxatridecanoyl ester)

THC (200 mg, 0.0004 mol) was dissolved in about 10 mL of dichloromethane. The mixture was stirred at ambient temperature for 5 min. Next, 3,6,9,12-tetraoxatridecanoic acid (43.3 mg, 0.195 mmol) in dichloromethane (1.75 mL) was added followed by 4-dimethylaminopyridine (1.8 mg, 0.015 mmol) and N,N'-dicyclohexylcarbodiimide (49.5 mg, 0.24 mmol). The mixture was stirred at ambient temperature overnight. The mixture was filtered, concentrated under a reduced pressure and chromatographed on silica gel with hexane-ethyl acetate (gradient 4:1, 2:1, 1:1, 0:1). Fractions containing the product were concentrated under a reduced pressure, dissolved in hexane with a few drops of ethyl acetate, filtered and concentrated again to afford ALL00117 (65.5 mg, 65%) as an oil.

For ALL00117, the $^1$H NMR (400 MHz, CDCl$_3$) was as follows: δ=6.57 (1H, d, J=1.8, H-4); 6.42(1H, d, J=1.8, H-2); 5.86-6.90 (1H, m, H-10); 4.42(2H, s, OCH$_2$CO$_2$); 3.88-3.76 (2H, m, PEG); 3.75-3.64(8H, m, PEG); 3.58-3.54(2H, m, PEG); 3.39(s, 3H, CH$_2$OCH$_3$); 3.11-3.03(1H, m, H-10a); 2.49(2H, t, J=8.3, ArCH$_2$); 2.09-2.17(2H, m); 1.85-1.94 (1H, m); 1.62-1.70(4H, m); 1.52-1.62(2H, m); 1.41(3H, s, 6β-Me); 1.24-1.41(5H, m); 1.09(3H, s, 6α-Me); 0.88 (3H, t, J=7.0, CH$_2$CH$_3$).

4.2 Synthesis of ALL00118 ($\Delta^9$-Tetrahydrocannabinol N,N-dimethylglycyl ester)

The same procedure as for ALL00117 (reaction time), starting from N,N-dimethylglycine, THC (150 mg, 0.3 mmol), N,N'-dicyclohexylcarbodiimide (49.5 mg, 0.24 mmol), 4-dimethylaminopyridine (1.8 mg, 0.015 mmol) in dichloromethane (1.75 mL) afforded 8 mg (4%) of ALL00118 as an oil.

For ALL00118, the $^1$H NMR (400 MHz, CDCl$_3$) was as follows: δ=6.55(1H, d, J=1.8, H-4); 6.41(1H, d, J=1.8, H-2); 5.89-5.92 (1H, m, H-10); 3.43(2H, s, COCH$_2$); 3.04-3.12 (1H, m, H-10a); 2.49(2H, t, J=7.8, ArCH$_2$); 2.44(6H, s, N(CH$_3$)$_2$); 2.09-2.16(2H, m); 1.85-1.93 (1H, m); 1.62-1.70 (4H, m); 1.52-1.61(2H, m); 1.40(3H, s, 6β-Me); 1.23-1.40 (5H, m); 1.08(3H, s, 6α-Me); 0.88 (3H, t, J=7.0, CH$_2$CH$_3$).

4.3 Synthesis of ALL00126 ($\Delta^9$-Tetrahydrocannabinol (R)-2,3-dihydroxypropyl carbonate)

The (S)-2,3-Bis(t-butyldimethylsilyloxy)propan-1-ol was prepared from (R)-(+)-1-benzylglycerol via reaction with t-butyldimethylsilyl chloride in the presence of imidazole and subsequent catalytic debenzylation (10% Pd/C, ethyl acetate).

To a stirred solution of (S)-2,3-bis(t-butyldimethylsilyloxy)propan-1-ol (129 mg, 0.3836 mmol) in dichloromethane (0.6 mL) at 0° C. under an argon atmosphere triethylamine (38.8 mg, 53.5 μL, 0.3836 mmol) was added, followed by triphosgene (37.9 mg, 0.1279 mmol) and stirring was continued at 0° C. for 3 h. The mixture was subsequently transferred to a solution of THC (88.0 mg, 0.28 mmol) and triethylamine (38.8 mg, 53.5 μL, 0.3836 mmol) in dichloromethane (0.6 mL) at 0° C. under an argon atmosphere with stirring. Stirring continued at ambient temperature for 3 h. The mixture was diluted with ethyl acetate (3 mL) and filtered. The filtrate was concentrated, dissolved in ethyl acetate (1 mL) and concentrated again. The residue was chromatographed on silica gel with hexane-ethyl acetate (gradient 40:1, 30:1, 20:1) to afford 120.1 mg (65%) of THC (S)-2,3-bis(t-butyldimethylsilyloxy)propyl carbonate as an oil.

THC (S)-2,3-bis(t-butyldimethylsilyloxy)propyl carbonate was dissolved in dichloromethane (200 μL), cooled to −15° C. and treated with 200 μL of cold 2N solution of triethylamine trihydrofluoride. The reaction mixture was left at 5° C. for 65 h. The mixture was poured to an excess of aqueous saturated sodium bicarbonate/ethyl acetate cooled to 0° C. with vigorous stirring. The aqueous layer was extracted twice with ethyl acetate. The combined organic extracts were dried over anhydrous sodium sulfate and concentrated. The residue was chromatographed on silica gel with hexane-ethyl acetate (gradient 3:1, 2:1, 1:1) to afford 60.5 mg (77%) of THC (R)-2,3-dihydroxypropyl carbonate (ALL00126) as an oil.

For ALL00126, the $^1$H NMR (400 MHz, CDCl$_3$) was as follows: δ=6.58 (1H, d, J=1.8, H-4); 6.50 (1H, d, J=1.6, H-2); 5.96-6.00 (1H, m, H-10); 4.30-4.39 (2H, m); 4.00-4.08 (1H, m); 3.64-3.81 (2H, m); 3.11-3.19 (1H, m, H-10a); 2.58 (1H, d, J=5.1); 2.46-2.53 (2H, m); 2.11-2.20 (2H, m); 2.07 (1H, t br, J=6.0); 1.86-1.95 (1H, m); 1.62-1.72 (4H, m); 1.52-1.62 (2H, m); 1.41 (3H, s, 6β-Me); 1.23-1.40 (5H, m); 1.09 (3H, s, 6α-Me); 0.88 (3H, t, J=7.0, CH$_2$CH$_3$).

4.4 Synthesis of ALL00127 ($\Delta^9$-Tetrahydrocannabinol 4-aminobutyl carbonate)

To a stirred solution of Fmoc-N-(4-hydroxybutyl)carbamate (40.2 mg, 0.129 mmol) in dry dichloromethane (0.5 mL) at 0° C. under an argon atmosphere triethylamine (13.05 mg, 18 μL, 0.129 mmol) was added, followed by triphosgene (13.4 mg, 0.04515 mmol) and stirring was continued at 0° C. for 2 h. Mixture was subsequently transferred to a solution of THC (47.2 mg, 0.15 mmol) and triethylamine (15.2 mg, 20.9 μL, 0.15 mmol) in dichloromethane (0.5 mL) at 0° C. under an argon atmosphere while stirring. Stirring was continued at ambient temperature for 2 h. Mixture was diluted with ethyl acetate (3 mL) and filtered. The filtrate was concentrated, dissolved in ethyl acetate (1 mL) and concentrated again to afford 87.3 mg of a crude product. The crude product was purified by preparative normal phase HPLC (ZORBAX RX-SIL, 9.4×250 mm, 5 μm) with hexane-ethyl acetate (3:1) to afford 41.8 mg (50%) of THC 4-(Fmoc-amino)butyl carbonate as an oil.

THC 4-(Fmoc-amino)butyl carbonate (65.7 mg, 0.10 mmol) was dissolved in 1.5 mL of 10% (v/v) solution of 1-octanethiol in acetonitrile. A solution of DBU (10% (v/v), 37.2 μL) was added and the mixture was stirred at ambient temperature for 5 min. The second portion of DBU solution (37.2 μL) was added and stirring was continued at ambient temperature for 15 min. Mixture was loaded directly on silica gel and chromatographed with dichloromethane-methanol (gradient 1:0, 30:1, 20:1, 10:1, 5:1). The combined fractions containing the product ($\Delta^9$-Tetrahydrocannabinol 4-aminobutyl carbonate) were diluted with chloroform, concentrated at 25° C. to ~0.3 mL, diluted with chloroform and concentrated. The remaining oil (29 mg, 67%) was immediately dissolved in chloroform and was stored at −20° C.

For ALL00127, the $^1$H NMR (400 MHz, CDCl$_3$) was as follows: δ=6.56 (1H, d, J=1.8, H-4); 6.50 (1H, d, J=1.8, H-2); 5.98-6.12 (1H, m, H-10); 4.20-4.32 (2H, m); 3.11-3.19 (1H, m, H-10a); 2.76 (2H, t, J=7.0); 2.49 (2H, t, J=7.8); 2.10-2.18 (2H, m); 1.87-1.94 (1H, m); 1.75-1.83 (2H, m);

1.63-1.72 (4H, m); 1.50-1.63 (6H, m); 1.41 (3H, s, 6β-Me); 1.23-1.40 (5H, m); 1.09 (3H, s, 6α-Me); 0.88 (3H, t, J=6.9, $CH_2CH_3$).

4.5 Synthesis of ALL00129 ($\Delta^9$-Tetrahydrocannabinol 3-hydroxy-2-(hydroxymethyl)-2-methylpropanoate)

To a stirred solution of THC (23.1 mg, 0.07346 mmol) and 5-carboxy-2,2,5-trimethyl-1,3-dioxane (15.4 mg, 0.08815 mmol) in dichloromethane (0.4 mL) was added to 4-dimethylaminopyridine (1.5 mg, 0.007346 mmol) followed by N,N'-dicyclohexylcarbodiimide (20.5 mg, 0.09917 mmol). The mixture was stirred at ambient temperature for 2 h. Additional portions of 5-carboxy-2,2,5-trimethyl-1,3-dioxane (15 mg, 0.08611 mmol), 4-dimethylaminopyridine (3 mg, 0.0145 mmol) and N,N'-dicyclohexylcarbodiimide (18 mg, 0.08724 mmol) were added and stirred for an additional 3.5 h. The mixture was diluted with hexane (0.4 mL), filtered, concentrated under a reduced pressure and chromatographed on silica gel with hexane-ethyl acetate (gradient 10:1, 8:1, 5:1) to afford THC 3-hydroxy-2-(hydroxymethyl)-2-methylpropanoate acetonide (25.7 mg, 55%) as an oil.

Zinc trifluoromethanesulfanate (25 mg) was added to a solution of THC 3-hydroxy-2-(hydroxymethyl)-2-methylpropanoate acetonide (20.56 mg, 0.04369 mmol) and 1-octanethiol (100 µL) in dichloromethane (1.4 mL). The mixture was stirred at ambient temperature for 3 h. The mixture was filtered, the filtrate was concentrated and the residue was purified by normal phase HPLC (ZORBAX RX-SIL, 5 µm, 9.4×250 mm, hexane-ethyl acetate (1:1)) to afford 8.36 mg (44%) of THC 3-hydroxy-2-(hydroxymethyl)-2-methylpropanoate (ALL00129) as an oil. LC-MS was as follows: 431.201 (M+H$^+$, 100%), 315.158 (92%).

4.6 Synthesis of ALL00130 ($\Delta^9$-Tetrahydrocannabinol glycinate)

N-(2-nitrophenylsulfenyl)glycine was released from dicyclohexylammonium salt by extraction from pH 3.5 citrate buffer with dichloromethane.

The same procedure as for ALL00134 (total reaction time 8 h), starting from THC (20.6 mg), N-(2-nitrophenylsulfenyl)glycine (18.1 mg), N,N'-dicyclohexylcarbodiimide (19 mg) and 4-dimethylaminopyridine (0.8 mg) in dichloromethane, with subsequent additions (in three portions) of N-(2-nitrophenylsulfenyl)glycine (25 mg) and N,N'-dicyclohexylcarbodiimide (26 mg) afforded, after normal phase HPLC (ZORBAX RX-SIL, 5 µm, 9.4×250 mm, hexane-ethyl acetate 70:30), 5.1 mg of THC N-(2-nitrophenylsulfenyl)glycinate as a yellow oil.

THC N-(2-nitrophenylsulfenyl)glycinate (6.1 mg, 0.0116 mmol) was dissolved at ambient temperature in dry dichloromethane containing 10% (v/v) of thiophenol and 1.5% (v/v) of TFA (100 µL). After 5 min the mixture was quenched by addition of 120 µL 3% triethylamine in DCM (at 0° C.). The solution of crude product was chromatographed directly on silica gel with dichloromethane-methanol (gradient 1:0, 20:1, 10:1, 5:1). The combined fractions containing the product were diluted with chloroform, concentrated at 25° C. to ~3 mL, diluted with chloroform and concentrated again to ~0.5 mL. The solution of product was diluted with chloroform again (~5 mL) and concentrated to dryness. Remaining oil was immediately dissolved in chloroform, concentrated to dryness (2.49 mg, 58%), and immediately dissolved in chloroform to afford a stock solution of THC glycinate (ALL00130) stored at –20° C.

For ALL00130, the $^1$H NMR (400 MHz, CDCl$_3$) was as follows: δ=6.56 (1H, d, J=1.7, H-4); 6.41 (1H, d, J=1.8, H-2); 5.88-5.92 (1H, m, H-10); 3.70 (2H, AB system, COCH$_2$); 3.00-3.09 (1H, m, H-10a); 2.46-2.55 (2H, m); 2.10-2.20 (2H, m); 1.85-1.98 (1H, m); 1.62-1.73 (4H, m); 1.50-1.62 (5H, m); 1.41 (3H, s, 6β-Me); 1.23-1.40 (5H, m); 1.09 (3H, s, 6α-Me); 0.88 (3H, t, J=7.0, CH$_2$CH$_3$).

4.7 Synthesis of ALL00133 ($\Delta$9-Tetrahydrocannabinol β-alaninate)

The same procedure as for ALL00134 (reaction time 3 h), starting from THC (31.4 mg, 0.10 mmol), N-(2-nitrophenylsulfenyl)-β-alanine (36.6 mg, 0.13 mmol), N,N'-dicyclohexylcarbodiimide (34 mg, 0.165 mmol) and 4-dimethylaminopyridine (5.1 mg, 0.025 mmol) in dichloromethane (0.5 mL) afforded, after silica gel chromatography with hexane-ethyl acetate (gradient 10:1, 6:1), 42.2 mg (78%) of THC N-(2-nitrophenylsulfenyl)-β-alaninate as a yellow oil.

THC N-(2-nitrophenylsulfenyl)-β-alaninate (35.8 mg, 0.0665 mmol) was dissolved at ambient temperature in dry dichloromethane containing 10% (v/v) of thiophenol and 1.5% (v/v) of TFA (150 µL). After 10 min the mixture was quenched by addition of 180 µL 3% triethylamine in DCM (at 0° C.). The solution of crude product was chromatographed directly on silica gel with dichloromethane-methanol (gradient 1:0, 30:1, 20:1, 10:1, 7:1). The combined fractions containing the product were diluted with chloroform, concentrated at 25° C. to ~3 mL, diluted with chloroform and concentrated again to ~0.5 mL. The solution of product was diluted with chloroform again (~5 mL) and concentrated to dryness. The remaining oil was immediately dissolved in chloroform, concentrated to dryness (11.47 mg, 45%), and immediately dissolved in chloroform to afford a stock solution of THC β-alaninate (ALL00133) stored at –20° C.

For ALL00133, the $^1$H NMR (400 MHz, CDCl$_3$) was as follows: δ=6.55 (1H, d, J=1.5, H-4); 6.41 (1H, d, J=1.5, H-2); 5.93-5.97 (1H, m, H-10); 2.98-3.16 (3H, m, H-10a and CH$_2$N); 2.66-2.84 (2H, m, COCH$_2$); 2.45-2.53 (2H, m); 2.10-2.20 (2H, m); 1.75-1.99 (3H, m); 1.62-1.73 (4H, m); 1.50-1.62 (2H, m); 1.41 (3H, s, 6β-Me); 1.23-1.40 (5H, m); 1.09 (3H, s, 6α-Me); 0.88 (3H, t, J=6.9, CH$_2$CH$_3$).

4.8 Synthesis of ALL00134 ($\Delta$9-Tetrahydrocannabinol (S)-2,3-dihydroxypropanoate)

To a stirred solution of THC (31.4 mg, 0.1 mmol) and (S)-4-carboxy-2,2-dimethyl-1,3-dioxolane (22.1 mg, 0.13 mmol) in dichloromethane (0.4 mL), 4-dimethylaminopyridine (5.2 mg, 0.025 mmol) was added followed by N,N'-dicyclohexylcarbodiimide (34.0 mg, 0.165 mmol). The mixture was stirred at ambient temperature for 2 h. The mixture was diluted with hexane (0.4 mL), filtered, concentrated under a reduced pressure and chromatographed on silica gel with hexane-ethyl acetate (gradient 30:1, 20:1) to afford THC (S)-2,3-dihydroxypropanoate acetonide (22.7 mg, 51%) as an oil.

Zinc trifluoromethanesulfanate (10 mg, 0.0275 mmol) was added to a solution of THC (S)-2,3-dihydroxypropanoate acetonide (26.9 mg, 0.0532 mmol) and 1-octanethiol (93.4 mg, 111 µL, 0.6385 mmol) in dichloromethane (1 mL) and the mixture was stirred at ambient temperature for 21 h. The mixture was filtered, the filtrate was concentrated and the residue was chromatographed on silica gel with hexane-ethyl acetate (gradient 4:1, 3:1, 2:1) to afford 18.1 mg (84%) of THC (S)-2,3-dihydroxypropanoate (ALL00134) as an oil.

For ALL00134, the $^1$H NMR (400 MHz, CDCl$_3$) was as follows: δ=6.59 (1H, d, J=1.7, H-4); 6.44 (1H, d, J=1.8, H-2); 5.85-5.89 (1H, m, H-10); 4.50-4.55 (1H, m); 4.00-4.14 (2H, m); 3.11 (1H, d, J=5.7); 3.02-3.10 (1H, m, H-10a); 2.47-2.54 (2H, m); 2.19 (1H, t, J=6.8); 2.11-2.19 (2H, m); 1.87-1.94 (1H, m); 1.62-1.71 (4H, m); 1.52-1.62 (2H, m); 1.41 (3H, s, 6β-Me); 1.23-1.39 (5H, m); 1.09 (3H, s, 6α-Me); 0.88 (3H, t, J=6.9, CH$_2$CH$_3$).

4.9 Synthesis of ALL00138 ($\Delta^9$-Tetrahydrocannabinol (S)-2,3-dihydroxypropyl carbonate)

To a stirred solution of (R)-(−)-Solketal (22.2 mg, 0.168 mmol) in dichloromethane (0.4 mL) at 0° C. under an argon atmosphere, triethylamine (17.7 mg, 24.4 μL, 0.175 mmol) was added, followed by triphosgene (16.6 mg, 0.056 mmol) as stirring continued at 0° C. for 4 h. The mixture was subsequently transferred to a solution of THC (44.0 mg, 0.14 mmol) and triethylamine (18.4 mg, 25.4 μL, 0.182 mmol) in dichloromethane (0.4 mL) under an argon atmosphere at 0° C. with stirring. Stirring continued at ambient temperature for 2 h. The mixture was diluted with ethyl acetate (2 mL) and filtered. The filtrate was concentrated, dissolved in ethyl acetate (1 mL) and concentrated again. The residue was chromatographed on silica gel with hexane-ethyl acetate (gradient 30:1, 20:1, 10:1) to afford 34.5 mg (52%) of THC (S)-2,3-dihydroxypropyl carbonate acetonide.

Zinc trifluoromethanesulfanate (12.1 mg, 0.0333 mmol) was added to a solution of THC (S)-2,3-dihydroxypropyl carbonate acetonide (30.5 mg, 0.06447 mmol) and 1-octanethiol (94.3 mg, 112 μL, 0.6447 mmol) in dichloromethane (1 mL) and the mixture was stirred at ambient temperature for 17 h. Mixture was filtered, filtrate was concentrated and the residue was chromatographed on silica gel with hexane-ethyl acetate (gradient 3:1, 2:1, 1:1) to afford 18.8 mg (67%) of THC (S)-2,3-dihydroxypropyl carbonate (ALL00138) as an oil.

For ALL00138, the $^1$H NMR (400 MHz, CDCl$_3$) was as follows: δ=6.58 (1H, d, J=1.7, H-4); 6.50 (1H, d, J=1.8, H-2); 5.96-6.00 (1H, m, H-10); 4.27-4.41 (2H, m); 4.00-4.08 (1H, m); 3.64-3.81 (2H, m); 3.11-3.19 (1H, m, H-10a); 2.46-2.52 (3H, m); 2.11-2.19 (2H, m); 1.85-1.98 (2H, m); 1.62-1.72 (4H, m); 1.52-1.62 (2H, m); 1.41 (3H, s, 6β-Me); 1.23-1.40 (5H, m); 1.09 (3H, s, 6α-Me); 0.88 (3H, t, J=7.0, CH$_2$CH$_3$).

4.10 Synthesis of ALL00144 ($\Delta^9$-Tetrahydrocannabinol (R)-2,3-dihydroxypropyl carbonate)

The same procedure as for ALL00134 starting from THC (42.79 mg, 0.136 mmol), (R)-4-carboxy-2,2-dimethyl-1,3-dioxolane (23.85 mg, 0.163 mmol), N,N'-dicyclohexylcarbodiimide (39.2 mg, 0.190 mmol) and 4-dimethylaminopyridine (3.3 mg, 0.027 mmol) in dichloromethane afforded, after silica gel chromatography with hexane-ethyl acetate 9:1, 46.96 mg (78%) of THC (R)-2,3-dihydroxypropanoate acetonide as an oil.

Zinc trifluoromethanesulfanate (25 mg) was added to a solution of THC (R)-2,3-dihydroxypropanoate acetonide (46.96 mg) and 1-octanethiol (100 μL) in dichloromethane (1.6 mL) and the mixture was stirred at ambient temperature overnight. Mixture was filtered, filtrate was concentrated and the residue was chromatographed using normal phase HPLC (ZORBAX RX-SIL, 5 μm, 9.4×250 mm, hexane-ethyl acetate 65:35) to afford 11.85 mg (28%) of THC (R)-2,3-dihydroxypropanoate (ALL00144) as an oil. LC-MS was as follows: 403.137 (M+H$^+$, 100%), 315.142 (61%).

5.0 Plasma Stability Studies

Approximately 1 mg/mL of stock solution of each prodrug was prepared in 100 μL of ethanol and 900 μL of acetonitrile. Ten μL of stock was spiked into 1 mL of plasma and vortexed. The samples were kept sealed in an amber vial and samples were obtained to analyze for bioconversion to parent drug.

6.0 Preparation of Drug Formulations 6.1 Preparation of Receiver Fluid

The receiver fluid was prepared by measuring 600 mL of nanopure H$_2$O into a graduated cylinder. The H$_2$O was filtered through a 0.2μ filter (Millipore, Billerica, Mass.). 50 mg of gentamicin was added to the filtered H$_2$O and 400 mL of PEG 400 was added.

6.2 Preparation of Drug Formulations

The prodrugs were made up in a solution of 90:8:2 PG:H$_2$O:IPM. For this solution, the appropriate amount of drug was weighed into a glass silanized culture tube and IPM was added, then 50 μL of PG to coat the drug, then an additional 247 μL PG was added and the donor solution was vortexed again. Finally 26 μL of water was added.

6.3 Permeation Experiments (i) Dermatomed skin harvested from abdominoplasty which was stored at −20° C. was used for the experiments. A PermeGear flow-through (In-Line, Hellertown, Pa.) diffusion cell system was used for the skin permeation studies.

(ii) Diffusion cells were kept at 32° C. with a circulating water bath. Human epidermal skin was arranged in the diffusion cell with stratum corneum (upper layer of skin) facing the donor compartment. Permeation area of the skin was 0.95 cm$^2$. Data was collected from a human skin donor with three diffusion cells per treatment.

(iii) Receiver solution was 40% aqueous PEG 400 and flow rate was adjusted to 0.8 mL/h. Each cell was charged with 90-100 μL of the respective drug formulation (donor solution). The formulation was applied to ensure complete coverage. Diffusion cells were covered with a stopper for the duration of the study.

(iv) Samples were collected into scintillation vials in 3 h increments for 24 h or 1.5 h for 12 h, then 3 h until 24 h. All the samples were stored at 4° C. until extracted. An aliquot (500 μL) of the 40% PEG 400 diffusion sample was placed into a silanized HPLC vial and 500 μL of acetonitrile was added to the sample, capped and vortexed.

(v) At the end of the experiment, the skin tissue was removed from the diffusion cell, rinsed with nanopure water, and blotted dry with a paper towel. The skin was tape stripped twice using book tape (Scotch™, 3M, St. Paul, Minn.) to remove drug formulation adhering to the tissue surface. The area of skin in contact with the drug was excised, chopped up and placed in a pre-weighed scintillation vial. Ten mL of acetonitrile was added to the vial and drug was extracted from the skin by shaking at room temperature overnight. The samples were either injected directly onto the HPLC or samples were diluted 10× with additional acetonitrile before analyzed by HPLC.

(vi) At the end of the experiment, a 10 μL aliquot of donor solution was removed and added to a scintillation vial containing 10 mL of acetonitrile. The vials were vortexed and then sonicated for 15 min. An aliquot of 1 mL was removed and transferred into a silanized HPLC vial for analysis.

7.0 Analytical Method

| | |
|---|---|
| Column | Brownlee ® C$_8$ reversed phase Spheri 5 μm, (4.6 × 220 mm) column with a |
| | Brownlee ® C$_8$ reversed phase 7 μm (3.2 × 150 mm) guard column or |
| | Symmetry ® C$_{18}$ 5 μm (2.1 × 150 mm) column with a Sentry |
| | Semmetry ® C$_{18}$ 3.5 μm (2.1 × 10 mm) guard column |

| | -continued |
|---|---|
| Mobile phase | 70:30 acetonitrile: 0.05% trifluroacetic acid with 5% acetonitrile, 80:20 acetonitrile: 0.05% trifluroacetic acid with 5% acetonitrile, 90:10 acetonitrile: 0.05% trifluroacetic acid with 5% acetonitrile, or 50:50→90:10→50:50 (gradient) acetonitrile: 0.05% trifluroacetic acid with 5% acetonitrile |
| Flow rate | 1.0 mL/min or 1.5 mL/min |
| Wavelength | 210 nm |
| Injection volume | 100 µL (diffusion samples and respective standards) 20 µL (skin samples, donor samples, and respective standards), skin samples were either injected directly onto the column or they were diluted 10x with additional acetonitrile before they were injected onto the column |
| Run time | 9-16 min |
| Retention times | $\Delta^9$-tetrahydrocannabinol = 6.0-6.1, 6.7, 7.9, 8.7 min<br>ALL00117 = 8.0 min<br>ALL00118 = 13.9 min<br>ALL00126 = 5.6 min<br>ALL00127 = 4.4 min<br>ALL00129 = 4.9, 6.6 min<br>ALL00134 = 4.2-4.3 min<br>ALL00138 = 4.3 min<br>ALL00144 = 4.3 min |

8.0 Data Analysis

The cumulative quantity of drug collected in the receiver compartment was plotted as a function of time. Flux value for a given experiment was obtained from the slope of a steady state portion of the cumulative amount of drug permeated versus time plot. Lag time was obtained from the x-intercept of the steady state portion of the cumulative amount of drug permeated vs. time plot. The combined results of the delivered prodrug and $\Delta^9$-tetrahydrocannabinol from the prodrug are listed as "total $\Delta^9$-tetrahydrocannabinol." These values represent the data as total $\Delta^9$-tetrahydrocannabinol equivalents delivered in the form of $\Delta^9$-tetrahydrocannabinol and/or prodrug.

Section III. Tables

TABLE 15

Plasma stability of $\Delta^9$-tetrahydrocannabinol prodrugs
% Prodrug at time (h)

| Prodrug | 0.1 | 0.5 | 1 | 2 | 2.5 | 3 | 3.5 | 5 | 24 |
|---|---|---|---|---|---|---|---|---|---|
| ALL00117 | 100 | — | 35 | — | 7 | — | 5 | — | — |
| ALL00118 | 100 | — | 94 | 86 | 81 | — | — | — | 15 |
| ALL00126 | 100 | — | 3 | — | 1 | — | 1 | — | — |
| ALL00127 | 100 | — | 100 | — | 91 | — | 85 | — | — |
| ALL00129 | 100 | — | 100 | — | — | 98 | — | — | 83 |

TABLE 15-continued

Plasma stability of $\Delta^9$-tetrahydrocannabinol prodrugs
% Prodrug at time (h)

| Prodrug | 0.1 | 0.5 | 1 | 2 | 2.5 | 3 | 3.5 | 5 | 24 |
|---|---|---|---|---|---|---|---|---|---|
| ALL00134 | 96 | 61 | — | 15 | — | — | — | 0.8 | 0 |
| ALL00138 | 30 | 0 | — | — | — | — | — | — | — |

TABLE 16

$\Delta^9$-Tetrahydrocannabinol and $\Delta^9$-tetrahydrocannabinol prodrugs

| Compound | Molecular formula | Molecular weight |
|---|---|---|
| $\Delta^9$-tetrahydrocannabinol | $C_{21}H_{30}O_2$ | 314.46 |
| ALL00117 | $C_{30}H_{46}O_7$ | 518.68 |
| ALL00118 | $C_{25}H_{37}NO_3$ | 399.57 |
| ALL00126 | $C_{25}H_{36}O_6$ | 432.55 |
| ALL00127 | $C_{26}H_{39}NO_4$ | 429.59 |
| ALL00129 | $C_{26}H_{38}O_5$ | 430.58 |
| ALL00130 | $C_{23}H_{33}NO_3$ | 371.51 |
| ALL00133 | $C_{24}H_{35}NO_3$ | 385.54 |
| ALL00134 | $C_{24}H_{34}O_5$ | 402.52 |
| ALL00138 | $C_{25}H_{36}O_6$ | 432.55 |
| ALL00144 | $C_{24}H_{34}O_5$ | 402.52 |

TABLE 17

Permeation data of $\Delta^9$-tetrahydrocannabinol (n = 2), ALL00117 (n = 3), ALL00118 (n = 3) and ALL00126 (n = 2) with 90:8:2 PG:H$_2$O:IPM donor solution

| Compound | 24 h skin conc (µmol/g) | 24 h cumulative amt (nmol) | Flux (nmol/cm$^2$/h) | Flux enhancement | Lag time (h) |
|---|---|---|---|---|---|
| $\Delta^9$-tetrahydrocannabinol (THC) | 6.1 ± 1.9 | 16.3 ± 0.3 | 1.0 ± 0.3 | — | 5.8 ± 5.9 |
| total $\Delta^9$-tetrahydrocannabinol * | 7.3 ± 1.8 | 3.7 ± 1.0 | 0.5 ± 0.1 | 0.45 | 15.4 ± 0.3 |
| ALL00117 | 7.3 ± 1.8 | 3.0 ± 0.3 | 0.4 ± 0.1 | | 15.1 ± 0.2 |
| THC from ALL00117 | ND | 0.7 ± 0.7 | — | | — |
| total $\Delta^9$-tetrahydrocannabinol * | 13.5 ± 5.8 | 11.4 ± 0.7 | 0.9 ± 0.1 | 0.90 | 11.6 ± 0.2 |
| ALL00118 | 9.8 ± 5.2 | 5.8 ± 0.4 | 0.5 ± 0.0 | | 12.8 ± 0.1 |
| THC from ALL00118 | 3.7 ± 0.6 | 5.6 ± 0.5 | 0.4 ± 0.0 | | 10.2 ± 0.3 |
| total $\Delta^9$-tetrahydrocannabinol * | 24.5 ± 5.8 | 89.4 ± 14.4 | 7.1 ± 0.2 | 7.13 | 10.6 ± 1.9 |
| ALL00126 | 17.8 ± 4.8 | 69.7 ± 10.7 | 5.7 ± 0.0 | | 10.8 ± 2.1 |
| THC from ALL00126 | 6.7 ± 1.0 | 19.7 ± 3.7 | 1.4 ± 0.2 | | 9.7 ± 1.1 |

TABLE 18

Permeation data of Δ9-tetrahydrocannabinol (n = 1), ALL00129 (n = 3), and ALL00138 (n = 3) with 90:8:2 PG:H₂O:IPM donor solution

| Compound | 24 h skin conc (μmol/g) | 24 h cumulative amt (nmol) | Flux nmol/cm²/h | Flux enhancement | Lag time (h) |
|---|---|---|---|---|---|
| Δ⁹-tetrahydrocannabinol (THC) | 17.4 ± 9.2 | 53.3 ± 0.0 | 3.2 ± 0.0 | — | 6.2 ± 0.0 |
| total Δ⁹-tetrahydrocannabinol * | 19.6 ± 12.6 | 74.2 ± 8.1 | 4.8 ± 0.7 | 1.53 | 7.8 ± 1.3 |
| ALL00129 | 19.6 ± 12.6 | 74.2 ± 8.1 | 4.8 ± 0.7 | | 7.8 ± 1.3 |
| THC from ALL00129 | ND | ND | — | | — |
| total Δ⁹-tetrahydrocannabinol * | 21.3 ± 7.3 | 37.6 ± 8.3 | 2.5 ± 0.5 | 0.79 | 8.1 ± 0.0 |
| ALL00138 | 7.2 ± 4.8 | 18.2 ± 1.4 | 1.0 ± 0.0 | | 5.9 ± 1.4 |
| THC from ALL00138 | 14.1 ± 2.8 | 19.4 ± 6.9 | 1.4 ± 0.5 | | 9.7 ± 0.4 |

TABLE 19

Permeation data of Δ⁹-tetrahydrocannabinol (n = 2), ALL00127 (n = 3), ALL00134 (n = 3) and ALL00144 (n = 2) with 90:8:2 PG:H₂O:IPM donor solution

| Compound | 24 h skin conc (μmol/g) | 24 h cumulative amt (nmol) | Flux (nmol/cm2/h) | Flux enhancement | Lag time (h) |
|---|---|---|---|---|---|
| Δ⁹-tetrahydrocannabinol(THC) | 23.3 ± 1.7 | 29.8 ± 3.3 | 2.0 ± 0.3 | — | 8.7 ± 0.3 |
| total Δ⁹-tetrahydrocannabinol * | 32.9 ± 27.7 | 15.6 ± 2.8 | 1.1 ± 0.3 | 0.53 | 8.6 ± 2.2 |
| ALL00127 | ND | ND | — | | — |
| THC from ALL00127 | 32.9 ± 27.7 | 15.6 ± 2.8 | 1.1 ± 0.3 | | 8.6 ± 2.2 |
| total Δ⁹-tetrahydrocannabinol * | 25.3 ± 12.6 | 137.2 ± 5.8 | 8.5 ± 0.3 | 4.16 | 7.0 ± 0.2 |
| ALL00134 | 24.5 ± 12.3 | 128.6 ± 5.1 | 8.0 ± 0.3 | | 7.0 ± 0.1 |
| THC from ALL00134 | 0.8 ± 0.2 | 8.6 ± 1.0 | 0.5 ± 0.0 | | 6.5 ± 2.3 |
| total Δ⁹-tetrahydrocannabinol * | 69.7 ± 37.3 | 149.0 ± 57.9 | 9.3 ± 3.5 | 4.56 | 7.2 ± 0.2 |
| ALL00144 | 65.5 ± 39.5 | 137.9 ± 55.2 | 8.6 ± 3.4 | | 7.2 ± 0.1 |
| THC from ALL00144 | 4.1 ± 2.2 | 11.1 ± 2.7 | 0.7 ± 0.1 | | 6.6 ± 1.8 |

Example 4

Section I. Summary

The objective was to synthesize Δ⁹-tetrahydrocannabinol prodrugs and assess the permeation of Δ⁹-tetrahydrocannabinol and its prodrugs through human abdominal skin in vitro. One Δ⁹-tetrahydrocannabinol prodrug was synthesized and tested. Flow through diffusion cells were used for the permeation studies. The receiver used for the permeation studies was a 40% aqueous PEG 400. The donor solution was comprised of 90:8:2 PG:H₂O:IPM. The flux and lag time values of Δ⁹-tetrahydrocannabinol and Δ⁹-tetrahydrocannabinol prodrugs were obtained from the permeation profiles. Drug accumulation in the skin after a 24 h diffusion experiment was determined as μmol/g wet tissue weight.

Section II. Methodology 1.0 Purpose: The purpose was to synthesize Δ⁹-tetrahydrocannabinol prodrugs and assess the human skin permeation of Δ⁹-tetrahydrocannabinol and Δ⁹-tetrahydrocannabinol prodrugs in vitro. The following compound was synthesized:

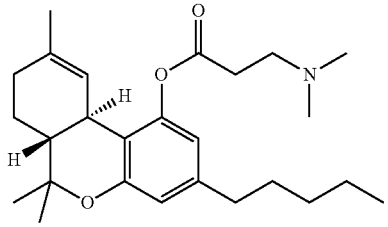

ALL00153
MW: 413.59
Formula C₂₆H₃₉NO₃

2.0 Skin Details

The skin samples used in the following experiments were supplied by Cooperative Human Tissue Network. The skin samples used herein were frozen at −20° C. for less than six months.

3.0 In Vitro Skin Permeation Studies 3.1 Preparation of Receiver Fluid

The receiver fluid was prepared by measuring 600 mL of nanopure H₂O into a graduated cylinder. The H₂O was filtered through a 0.2μ filter (Millipore, Billerica, Mass.) and 400 mL of PEG 400 was added.

3.2 Preparation of Drug Formulation

The drug formulation was made up in 90:8:2 PG:H₂O:IPM. For the solution, the appropriate amount of drug was weighed into a glass silanized culture tube and 7 μL of IPM was added. Next, 50 μL of PG was added and vortexed to get the drug into solution, then the remaining PG (247 μL) was added. Water was added last. Both donor solutions were saturated.

3.3 Permeation Experiments

Dermatomed skin harvested from abdominoplasty, stored at −20°, was used for the experiments. A PermeGear flow-through (In-Line, Hellertown, Pa.) diffusion cell system was used for the skin permeation studies.

Diffusion cells were kept at 32° C. with a circulating water bath. Human epidermal skin was arranged in the diffusion cell with stratum corneum (upper layer of skin) facing the donor compartment. Permeation area of the skin was 0.95 cm². Data was collected from a human skin donor with three diffusion cells per treatment.

The receiver solution was 40% aqueous PEG 400 and flow rate was adjusted to 0.8 mL/h. Each cell was charged with 100 μL of the respective drug formulation (donor solution). The formulation was applied to ensure complete coverage. Diffusion cells were covered with a stopper for the duration of the study.

Samples were collected into scintillation vials in 3 h increments for 24 h. All the samples were stored at 4° C. until extracted. An aliquot (500 µL) of the 40% PEG 400 diffusion sample was placed into a silanized HPLC vial and 500 µL of acetonitrile was added to the sample, capped and vortexed.

At the end of the experiment, the skin tissue was removed from the diffusion cell, rinsed with nanopure water, and blotted dry with a paper towel. The skin was tape stripped twice using book tape (Scotch™, 3M, St. Paul, Minn.) to remove drug formulation adhering to the tissue surface. The area of skin in contact with the drug was excised, chopped up and placed in a pre-weighed scintillation vial. Ten mL of acetonitrile was added to the vial and drug was extracted from the skin by shaking at room temperature overnight. The samples were analyzed by HPLC.

At the end of the experiment, a 10 µL aliquot of donor solution was removed and added to a scintillation vial containing 10 mL of acetonitrile. The vials were vortexed and then sonicated for 15 min. An aliquot of 1 mL was removed and transferred into a silanized HPLC vial for analysis.

4.0 Analytical Method

| | |
|---|---|
| Column | Brownlee ® $C_8$ reversed phase Spheri 5 µm, (4.6 × 220 mm) column with a Brownlee ® $C_8$ reversed phase 7 µm (3.2 × 150 mm) guard column |
| Mobile phase | 85:15 acetonitrile: 0.05% trifluroacetic acid with 5% acetonitrile |
| Flow rate | 1.5 mL/min |
| Wavelength | 210 nm |
| Injection volume | 100 µL (diffusion samples and respective standards) 20 µL (skin samples, donor samples, and respective standards) |
| Run time | 21 min |
| Retention times | $\Delta^9$-tetrahydrocannabinol = 5.1 min ALL00153 = 18.9 min |

5.0 Data Analysis

The cumulative quantity of drug collected in the receiver compartment was plotted as a function of time. The flux value for a given experiment was obtained from the slope of a steady state portion of the cumulative amount of drug permeated vs. time plot. Lag time was obtained from the x-intercept of the steady state portion of the cumulative amount of drug permeated vs. time plot. The combined results of the delivered prodrug and $\Delta^9$-tetrahydrocannabinol from the prodrug are listed as "total $\Delta^9$-tetrahydrocannabinol." These values represent the data as total $\Delta^9$-tetrahydrocannabinol equivalents delivered in the form of $\Delta^9$-tetrahydrocannabinol and/or prodrug.

Section III. Tables

TABLE 20

Permeation data of $\Delta^9$-tetrahydrocannabinol (n = 2) and ALL00153 (n = 3) in 90:8:2 PG:$H_2O$:IPM donor solution

| Compound | 24 h skin conc (µmol/g) | 24 h cumulative amt (nmol) | Flux (nmol/cm$^2$/h) | Flux enhancement | Lag time (h) |
|---|---|---|---|---|---|
| $\Delta^9$-tetrahydrocannabinol (THC) | 8.5 ± 3.5 | 15.7 ± 4.5 | 1.1 ± 0.3 | — | 9.0 ± 0.7 |
| total $\Delta^9$-tetrahydrocannabinol * | 11.3 ± 3.4 | 23.7 ± 6.1 | 1.9 ± 0.5 | 1.75 | 10.9 ± 0.3 |
| ALL00153 | 0.6 ± 0.1 | ND | — | — | — |
| THC from ALL00153 | 10.9 ± 3.1 | 23.7 ± 6.1 | 1.9 ± 0.5 | | 10.9 ± 0.3 |

* total THC = total $\Delta^9$-tetrahydrocannabinol equivalents delivered in the form of $\Delta^9$-tetrahydrocannabinol and/or prodrug All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar references in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the present disclosure.

Alternative embodiments of the claimed disclosure are described herein, including the best mode known to the inventors for practicing the claimed invention. Of these, variations of the disclosed embodiments will become apparent to those of ordinary skill in the art upon reading the foregoing disclosure. The inventors expect skilled artisans to employ such variations as appropriate (e.g., altering or combining features or embodiments), and the inventors intend for the invention to be practiced otherwise than as specifically described herein.

Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

The use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Thus, recitation of ranges of values herein are merely intended to serve as a shorthand method of referring individually to each separate value falling within the range, unless otherwise indicated herein, and each separate value is incorporated into the specification as if it were individually recited herein.

It is to be understood that any ranges, ratios and ranges of ratios that can be formed by, or derived from, any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art most closely related to a particular range, ratio or range of ratios will appreciate that such values are unambiguously derivable from the data presented herein.

We claim:
1. A compound having the formula:

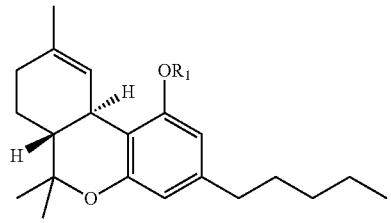

wherein $OR_1$ is selected from the group consisting of a diphosphate, a triphosphate, an alkali metal phosphate salt, an alkaline earth metal phosphate salt, and a phosphate salt of an organic base.

2. The compound of claim 1 wherein the organic base is selected from a group consisting of choline, betaine, caffeine, N, N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, hydrabamine, isopropylamine, methylglucamine, morpholine, piperidine, polyamine resins, procaine, purines, theobromine, triethylamine, trimethylamine, tripropylamine, tromethamine, tetramethylammonium hydroxide, benzyltrimethylammonium hydroxide, tris(hydroxymethyl) aminomethane (TRIS), N-(2-hydroxyethyl)pyrrolidine, piperazine, glucosamine, arginine, lysine and histidine.

3. The compound of claim 1 wherein $OR_1$ is selected from the group consisting of a diphosphate, a triphosphate, and salts thereof.

4. A compound having the formula:

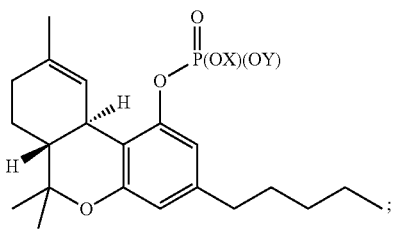

and
wherein X is selected from a group consisting of: hydrogen, alkali metals, alkaline earth metals, and cations of pharmaceutically acceptable organic bases and Y is selected from a group consisting of: alkali metals, alkaline earth metals, and cations of pharmaceutically acceptable organic bases.

5. The compound of claim 4, which is

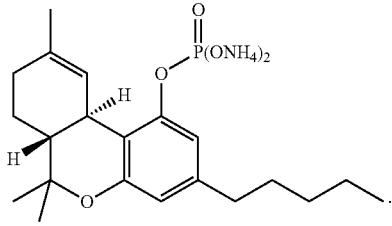

6. A pharmaceutical composition comprising:
(a) a compound as described in claim 1; and
(b) a pharmaceutically acceptable excipient.

7. A method of treating a medical condition in a mammal comprising the step of administering a compound as described in claim 1, wherein the administration is effective for the treatment of the condition;
wherein the medical condition is selected from the group consisting of: anorexia, nausea, emesis, pain, wasting syndrome, HIV-wasting, chemotherapy induced nausea and vomiting, alcohol use disorders, amyotrophic lateral sclerosis, increased intraocular pressure, glaucoma, cannabis use disorders, Tourette's syndrome, dystonia, multiple sclerosis, inflammatory bowel disorders, arthritis, dermatitis, Rheumatoid arthritis, systemic lupus erythematosus, anti-inflammatory, anti-convulsant, anti-psychotic, anti-oxidant, neuroprotective, immunomodulatory effects, peripheral neuropathic pain, post-herpetic neuralgia, diabetic neuropathy, shingles, burns, actinic keratosis, oral cavity sores and ulcers, post-episiotomy pain, psoriasis, pruritis, contact dermatitis, eczema, bullous dermatitis herpetiformis, exfoliative dermatitis, mycosis fungoides, pemphigus, severe erythema multiforme, Stevens-Johnson syndrome, seborrheic dermatitis, ankylosing spondylitis, psoriatic arthritis, Reiter's syndrome, gout, chondrocalcinosis, joint pain secondary to dysmenorrhea, fibromyalgia, musculoskeletal pain, neuropathic-postoperative complications, polymyositis, acute non-specific tenosynovitis, bursitis, epicondylitis, post-traumatic osteoarthritis, synovitis, and juvenile rheumatoid arthritis.

8. The method of claim 7 wherein the compound is administered by a route selected from the group consisting of: transdermal, topical, oral, buccal, sublingual, intra venous, intra muscular, vaginal, rectal, ocular, nasal and follicular.

9. A method of administering a compound to a mammal comprising the steps of:
(a) combining a compound of claim 1 with a pharmaceutical excipient to form a pharmaceutical composition;
(b) creating a dosage form suitable for administration to the mammal from the pharmaceutical composition; and
(c) administering the dosage form to the mammal.

10. The method of claim 9 wherein the pharmaceutical composition is administered by a route selected from the group consisting of: transdermal, topical, oral, buccal, sublingual, intra venous, intra muscular, vaginal, rectal, ocular, nasal and follicular.

* * * * *